(12) United States Patent
Dana et al.

(10) Patent No.: US 9,011,861 B2
(45) Date of Patent: Apr. 21, 2015

(54) THERAPEUTIC COMPOSITIONS FOR THE TREATMENT OF DRY EYE DISEASE

(75) Inventors: Reza Dana, Newton, MA (US); Sunil Chauhan, Somerville, MA (US)

(73) Assignee: Schepens Eye Research Institute, Boston, MA (US)

( * ) Notice: Subject to any disclaimer, the term of this patent is extended or adjusted under 35 U.S.C. 154(b) by 68 days.

(21) Appl. No.: 13/035,695

(22) Filed: Feb. 25, 2011

(65) Prior Publication Data

US 2011/0206620 A1 Aug. 25, 2011

Related U.S. Application Data

(60) Provisional application No. 61/308,091, filed on Feb. 25, 2010, provisional application No. 61/329,845, filed on Apr. 30, 2010, provisional application No. 61/331,278, filed on May 4, 2010.

(51) Int. Cl.
| | | |
|---|---|---|
| *A61K 39/395* | (2006.01) | |
| *C07K 16/22* | (2006.01) | |
| *A61K 38/17* | (2006.01) | |
| *A61K 9/00* | (2006.01) | |
| *A61K 39/00* | (2006.01) | |

(52) U.S. Cl.
CPC .......... *A61K 38/179* (2013.01); *A61K 2039/505* (2013.01); *C07K 16/22* (2013.01); *A61K 9/0048* (2013.01)

(58) Field of Classification Search
None
See application file for complete search history.

(56) References Cited

U.S. PATENT DOCUMENTS

| | | | |
|---|---|---|---|
| 5,225,539 A | 7/1993 | Winter | |
| 5,693,761 A | 12/1997 | Queen et al. | |
| 5,869,619 A | 2/1999 | Studnicka | |
| 6,107,046 A | 8/2000 | Alitalo et al. | |
| 6,403,088 B1 | 6/2002 | Alitalo et al. | |
| 6,706,487 B1* | 3/2004 | Abdel-Meguid et al. | 435/7.1 |
| 6,709,833 B2* | 3/2004 | Fukui et al. | 435/7.95 |
| 6,881,557 B2 | 4/2005 | Foote | |
| 7,122,654 B2 | 10/2006 | Achen et al. | |
| 7,208,582 B2* | 4/2007 | Rosen et al. | 530/387.1 |
| 7,410,639 B2 | 8/2008 | Achen et al. | |
| 7,422,741 B2 | 9/2008 | Alitalo et al. | |
| 7,423,125 B2 | 9/2008 | Alitalo et al. | |
| 7,611,711 B2 | 11/2009 | Alitalo et al. | |
| 7,892,081 B2 | 2/2011 | Glavich et al. | |
| 2006/0182783 A1* | 8/2006 | Hughes et al. | 424/427 |
| 2007/0078077 A1* | 4/2007 | Peyman | 514/2 |
| 2010/0278736 A1 | 11/2010 | Alitalo et al. | |
| 2013/0045927 A1 | 2/2013 | Dana et al. | |

FOREIGN PATENT DOCUMENTS

| | | |
|---|---|---|
| WO | WO 95/21868 A1 | 8/1995 |
| WO | WO-00/07601 A1 | 2/2000 |
| WO | WO 00/21560 A1 | 4/2000 |
| WO | WO 00/23565 A2 | 4/2000 |
| WO | WO 00/37025 A2 | 6/2000 |
| WO | WO 01/52875 A1 | 7/2001 |
| WO | WO 02/057299 A2 | 7/2002 |
| WO | WO 02/060950 A2 | 8/2002 |
| WO | WO 03/006104 A2 | 1/2003 |
| WO | WO 03/072029 A2 | 9/2003 |
| WO | WO 2005/087177 A2 | 9/2005 |
| WO | WO 2005/087812 A1 | 9/2005 |
| WO | WO 2005/112971 A1 | 12/2005 |
| WO | WO 2009/025763 A3 | 2/2009 |
| WO | WO 2009/060198 A1 | 5/2009 |
| WO | WO 2009/089036 A2 | 7/2009 |
| WO | WO 2010/027743 A1 | 3/2010 |
| WO | WO 2010/060768 A1 | 6/2010 |

OTHER PUBLICATIONS

Kinose et al., Molecular Vision 11: 366-73, 2005.*
Prescre Int 15(84): 127-9, Aug. 2006.*
Steffensmeier et al., Am J Ophthalmology 143(3): 512-513, Mar. 2007.*
Yu et al., Investigative Ophthalmology & Visual Science 49(2): 522-527, Feb. 2008.*
Witte et al., Cancer and Metastasis Reviews 17: 155-161, 1998.*
Cochran et al., J. Immunol. Meth. 287: 147-158, 2004.*
Riemer et al., Mol. Immunol. 42: 1121-1124, 2005.*
Tol et al., N. Engl J Med. 5;360(6):563-72, Feb. 2009.*
Semraro et al., Expert Opin. Drug Saf. 13(6): 785-802, 2014.*
Azar, "Corneal Angiogenic Privilege: Angiogenic and Antiangiogenic Factors in Corneal Avascularity, Vasculogenesis, and Wound Healing," *Trans Am Ophthalmol Soc*, 104:264-302 (2006).
Cursiefen et al., "Lymphatic Vessels in Vascularized Human Corneas: Immunohistochemical Investigation Using LYVE-1 and Podoplanin," *Investigative Ophthalmology & Visual Science*, 43(7):2127-2135 (2002).
Enriquez-de-Salamanca et al., "Tear cytokine and chemokine analysis and clinical correlations in evaporative-type dry eye disease," *Molecular Vision*, 16:862-873 (2010).
Goyal et al., "Blockade of Prolymphangiogenic VEGF-C Suppresses Dry Eye Disease," ARVO Abstract (2010).
Goyal et al., "Corneal Lymphangiogenesis in a Murine Model of Dry Eye Disease," ARVO Abstract (2009).
Van de Veire et al., "Further Pharmacological and Genetic Evidence for the Efficacy of PlGF Inhibition in Cancer and Eye Disease," *Cell*, 141:178-190 (2010).
Woolard et al., "VEGF$_{165}$b, an Inhibitory Vascular Endothelial Growth Factor Splice Variant: Mechanism of Action, In vivo Effect on Angiogenesis and Endogenous Protein Expression," *Cancer Research*, 64:7822-7835 (2004).
Bock et al., "Blockade of VEGFR3-signalling specifically inhibits lymphangiogenesis in inflammatory corneal neovascularisation," *Graefes Arch. Clin. Exp. Ophthalmol.*, 246: 115-119 (2008).
Rashid et al., "Topical Omega-3 and Omega-6 Fatty Acids for Treatment of Dry Eye," Arch Ophthalmol, 126(2):219-225 (2008).
Chauhan et al., "Role of Th 17 Cells in the Immunopathogenesis of Dry Eye Disease," Mucosal Immunol., 2(4):375-376 (2009).

(Continued)

*Primary Examiner* — Phuong Huynh
(74) *Attorney, Agent, or Firm* — Marshall, Gerstein & Borun LLP

(57) ABSTRACT

Described herein are materials and methods for treating dry eye disease in a subject.

22 Claims, 10 Drawing Sheets

(56) References Cited

OTHER PUBLICATIONS

Jones et al., "Replacing the complementarity determining regions in a human antibody with those from a mouse," Nature, 321:522-525 (1986).

Padlan, E., "A Possible Procedure for Reducing the Immunogenicity of Antibody Variable Domains While Preserving Their Ligand-Binding Properties," Molecular Immunology, 28(4):489-498 (1991).

Achen et al., Vascular endothelial growth factor D (VEGF-D) is a ligand for the tyrosine kinases VEGF receptor 2 (Flk1) and VEGF receptor 3 (Flt4), Proc. Natl. Acad. Sci. USA, 95:548-53 (1998).

Alitalo et al., Lymphangiogenesis in development and human disease, Nature, 438(7070):946-953 (2005).

Ambrosio et al., LASIK- associated dry eye and neurotrophic epitheliopathy: Pathophysiology and strategies for prevention and treatment, J. Refract. Surg., 24(4)396-407 (2008).—Abstract Only.

Chauhan et al., A novel pro-lymphangiogenic function for Th17/IL-17, Blood, 118(17):4630 (2011).

Chauhan et al., Autoimmunity in dry eye is due to resistance of the Th17 to Treg suppression, J. Immunol., 182:1247-52 (2009).

Dana, Corneal Antigen Presentation: Molecular Regulation and Functional Implications, Oculo. Surf., S169-72 (2005).

De Paiva et al., IL-17 disrupts corneal barrier following desiccating stress, Mucosal Immunol., 2(3):243 (2006).

De Paiva et al., Rationale for anti-inflammatory therapy in dry eye syndrome, Arq. Bras. Oftalmol., 71:89-95 (2008).

Enholm et al., Adenoviral expression of vascular endothelial growth factor—C induces lymphangiogenesis in the skin, Circ. Res., 88:623-9 (2001).

Huggenberger et al., An important role of lymphatic vessel activation in limiting acute inflammation, Blood, 117(17):4667-78 (2011).

Huggenberger et al., Stimulation of lymphangiogenesis via VEGFR-3 inhibits chronic skin inflammation, J. Exper. Med., 207(10):2255-69 (2007).

Jeltsch et al., Hyperplasia of lymphatic vessels in VEGF-C transgenic mice, Sci., 276:1423 (1997).

Joukov et al., A novel vascular endothelial growth factor, VEGF-C is a ligand for the Flt4 (VEGFR-3) and KDR (VEGFR-2) receptor tyrosine kinases, Embo J., 15(2):290-8 (1996).

Kajiya et al., Activation of the VEGFR-3 Pathway by VEGF-C attenuates UVB-induced edema formation and skin inflammation by promoting lymphangiogenesis, J. Invest. Dermatol., 129:1292 (2009).

Makinen et al., Inhibition of lymphangiogenesis with resulting lymphedema in transgenic mice expressing soluble VEGF receptor-3, Nature Med., 7(2):199-205 (2001).

Oh et al., VEGF and VEGF-C: Specific induction of angiogenesis and lymphangiogenesis in the differentiated avian chorioallantoic membrane, Devel. Biol., 188:96-109 (1997).

Pullinger et al., Proliferation of lymphatics in inflammation, J. Pathol., 157-70 (1937).

Suvajac et al., Soft-contact-lenses-induced complications, Vojnosanit Pregl., 65(1):15-20 (2008).—Abstract Only.

Veikkola et al., Signalling via vascular endothelial growth factor receptor-3 is sufficient for lymphangiogenesis in transgenic mice, Embo J., 20(6):1223-31 (2001).

Witmer et al., Vascular endothelial growth factors and angiogenesis in eye diseases, Progress in Retinal and Eye Research, 22:1-29 (2003).

* cited by examiner

SEQUENCE LISTING

<160> NUMBER OF SEQ ID NOS: 53

<210> SEQ ID NO 1
<211> LENGTH: 9
<212> TYPE: PRT
<213> ORGANISM: Artificial Sequence

```
<220> FEATURE:
<223> OTHER INFORMATION: Synthetic peptide

<400> SEQUENCE: 1

Ser Gly Tyr Trp Trp Asp Thr Trp Phe
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2

Ser Cys Tyr Trp Arg Asp Thr Trp Phe
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic peptide

<400> SEQUENCE: 3

Lys Val Gly Trp Ser Ser Pro Asp Trp
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Phe Val Gly Trp Thr Lys Val Leu Gly
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Tyr Ser Ser Ser Met Arg Trp Arg His
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Arg Trp Arg Gly Asn Ala Tyr Pro Gly
1               5

<210> SEQ ID NO 7
<211> LENGTH: 9
<212> TYPE: PRT
<213> ORGANISM: Artificial Sequence
<220> FEATURE:
```

```
<223> OTHER INFORMATION: Synthetic peptide

<400> SEQUENCE: 7

Ser Ala Val Phe Arg Gly Arg Trp Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide

<400> SEQUENCE: 8

Trp Phe Ser Ala Ser Leu Arg Phe Arg
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide

<400> SEQUENCE: 9

Trp Gln Leu Gly Arg Asn Trp Ile
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide

<400> SEQUENCE: 10

Val Glu Val Gln Ile Thr Gln Glu
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide

<400> SEQUENCE: 11

Ala Gly Lys Ala Ser Ser Leu Trp
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide

<400> SEQUENCE: 12

Arg Ala Leu Asp Ser Ala Leu Ala
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide
```

```
<400> SEQUENCE: 13

Tyr Gly Phe Glu Ala Ala Trp
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Tyr Gly Phe Leu Trp Gly Met
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Ser Arg Trp Arg Ile Leu Gly
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic peptide

<400> SEQUENCE: 16

His Lys Trp Gln Lys Arg Gln
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Met Asp Pro Trp Gly Gly Trp
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Arg Lys Val Trp Asp Ile Arg
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic peptide
```

```
<400> SEQUENCE: 19

Val Trp Asp His Gly Val
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic peptide

<400> SEQUENCE: 20

Cys Trp Gln Leu Gly Arg Asn Trp Ile Cys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic peptide

<400> SEQUENCE: 21

Cys Val Glu Val Gln Ile Thr Gln Glu Cys
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic peptide

<400> SEQUENCE: 22

Cys Ala Gly Lys Ala Ser Ser Leu Trp Cys
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic peptide

<400> SEQUENCE: 23

Cys Arg Ala Leu Asp Ser Ala Leu Ala Cys
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Synthetic peptide

<400> SEQUENCE: 24

Cys Tyr Gly Phe Glu Ala Ala Trp Cys
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide

<400> SEQUENCE: 25
```

```
Cys Tyr Gly Phe Leu Trp Gly Met Cys
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide

<400> SEQUENCE: 26

Cys Ser Arg Trp Arg Ile Leu Gly Cys
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide

<400> SEQUENCE: 27

Cys His Lys Trp Gln Lys Arg Gln Cys
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide

<400> SEQUENCE: 28

Cys Met Asp Pro Trp Gly Gly Trp Cys
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic peptide

<400> SEQUENCE: 29

Cys Arg Lys Val Trp Asp Ile Arg Cys
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic peptide

<400> SEQUENCE: 30

Cys Val Trp Asp His Gly Val Cys
1               5

<210> SEQ ID NO 31
<211> LENGTH: 13
<212> TYPE: PRT
<213> ORGANISM: Artificial Sequence
<220> FEATURE:
<223> OTHER INFORMATION: Synthetic peptide

<400> SEQUENCE: 31
```

```
Cys Gly Gln Met Cys Thr Val Trp Cys Ser Ser Gly Cys
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(6)
<223> OTHER INFORMATION: Xaa can be any naturally occurring amino acid

<400> SEQUENCE: 32

Gly Tyr Trp Xaa Xaa Xaa Trp
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 33

Gly Tyr Trp Xaa Xaa Xaa Trp Xaa
1               5

<210> SEQ ID NO 34
<211> LENGTH: 448
<212> TYPE: PRT
<213> ORGANISM: Homo sapiens

<400> SEQUENCE: 34

Glu Val Arg Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Pro Arg
                20                  25                  30

Ala Met Ala Trp Val Arg Gln Ala Pro Gly Lys Gly Leu Glu Trp Val
            35                  40                  45

Ser Ser Ile Ser Ala Gln Gly Ala Ser Ala Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Val Ser Gly Phe Gly Pro Trp Gly Arg Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160
```

```
Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 35
<211> LENGTH: 217
<212> TYPE: PRT
<213> ORGANISM: Homo sapiens

<400> SEQUENCE: 35

Ser Tyr Glu Leu Thr Gln Pro Pro Ser Ser Gly Thr Pro Gly Gln
1               5                   10                  15

Arg Val Thr Ile Ser Cys Ser Gly Ser Ser Asn Ile Gly Arg His
            20                  25                  30

Thr Val Ser Trp Tyr Gln Gln Val Pro Gly Thr Ala Pro Lys Leu Leu
        35                  40                  45

Ile Tyr Ser Asp Asp His Arg Pro Ser Gly Val Pro Asp Arg Phe Ser
    50                  55                  60

Ala Ser Lys Ser Gly Thr Ser Ala Ser Leu Thr Ile Thr Gly Leu Gln
65                  70                  75                  80

Ser Glu Asp Glu Ala Asp Tyr Tyr Cys Ala Ala Trp Asp Ser Leu
                85                  90                  95
```

```
Asn Gly Pro Trp Val Phe Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 36
<211> LENGTH: 2292
<212> TYPE: DNA
<213> ORGANISM: Homo sapiens
<220> FEATURE:
<221> NAME/KEY: CDS
<222> LOCATION: (1)..(2292)

<400> SEQUENCE: 36 atg gag agc aag gtg ctg ctg gcc gtc gcc ctg tgg ctc tgc gtg gag      48
Met Glu Ser Lys Val Leu Leu Ala Val Ala Leu Trp Leu Cys Val Glu
1               5                   10                  15 acc cgg gcc gcc tct gtg ggt ttg cct agt gtt tct ctt gat ctg ccc      96
Thr Arg Ala Ala Ser Val Gly Leu Pro Ser Val Ser Leu Asp Leu Pro
            20                  25                  30 agg ctc agc ata caa aaa gac ata ctt aca att aag gct aat aca act     144
Arg Leu Ser Ile Gln Lys Asp Ile Leu Thr Ile Lys Ala Asn Thr Thr
        35                  40                  45 ctt caa att act tgc agg gga cag agg gac ttg gac tgg ctt tgg ccc     192
Leu Gln Ile Thr Cys Arg Gly Gln Arg Asp Leu Asp Trp Leu Trp Pro
    50                  55                  60 aat aat cag agt ggc agt gag caa agg gtg gag gtg act gag tgc agc     240
Asn Asn Gln Ser Gly Ser Glu Gln Arg Val Glu Val Thr Glu Cys Ser
65                  70                  75                  80 gat ggc ctc ttc tgt aag aca ctc aca att cca aaa gtg atc gga aat     288
Asp Gly Leu Phe Cys Lys Thr Leu Thr Ile Pro Lys Val Ile Gly Asn
                85                  90                  95 gac act gga gcc tac aag tgc ttc tac cgg gaa act gac ttg gcc tcg     336
Asp Thr Gly Ala Tyr Lys Cys Phe Tyr Arg Glu Thr Asp Leu Ala Ser
            100                 105                 110 gtc att tat gtc tat gtt caa gat tac aga tct cca ttt att gct tct     384
Val Ile Tyr Val Tyr Val Gln Asp Tyr Arg Ser Pro Phe Ile Ala Ser
        115                 120                 125 gtt agt gac caa cat gga gtc gtg tac att act gag aac aaa aac aaa     432
Val Ser Asp Gln His Gly Val Val Tyr Ile Thr Glu Asn Lys Asn Lys
130                 135                 140 act gtg gtg att cca tgt ctc ggg tcc att tca aat ctc aac gtg tca     480
Thr Val Val Ile Pro Cys Leu Gly Ser Ile Ser Asn Leu Asn Val Ser
145                 150                 155                 160 ctt tgt gca aga tac cca gaa aag aga ttt gtt cct gat ggt aac aga     528
Leu Cys Ala Arg Tyr Pro Glu Lys Arg Phe Val Pro Asp Gly Asn Arg
                165                 170                 175
```

```
att tcc tgg gac agc aag aag ggc ttt act att ccc agc tac atg atc    576
Ile Ser Trp Asp Ser Lys Lys Gly Phe Thr Ile Pro Ser Tyr Met Ile
        180                 185                 190 agc tat gct ggc atg gtc ttc tgt gaa gca aaa att aat gat gaa agt    624
Ser Tyr Ala Gly Met Val Phe Cys Glu Ala Lys Ile Asn Asp Glu Ser
            195                 200                 205 tac cag tct att atg tac ata gtt gtc gtt gta ggg tat agg att tat    672
Tyr Gln Ser Ile Met Tyr Ile Val Val Val Val Gly Tyr Arg Ile Tyr
        210                 215                 220 gat gtg gtt ctg agt ccg tct cat gga att gaa cta tct gtt gga gaa    720
Asp Val Val Leu Ser Pro Ser His Gly Ile Glu Leu Ser Val Gly Glu
225                 230                 235                 240 aag ctt gtc tta aat tgt aca gca aga act gaa cta aat gtg ggg att    768
Lys Leu Val Leu Asn Cys Thr Ala Arg Thr Glu Leu Asn Val Gly Ile
            245                 250                 255 gac ttc aac tgg gaa tac cct tct tcg aag cat cag cat aag aaa ctt    816
Asp Phe Asn Trp Glu Tyr Pro Ser Ser Lys His Gln His Lys Lys Leu
        260                 265                 270 gta aac cga gac cta aaa acc cag tct ggg agt gag atg aag aaa ttt    864
Val Asn Arg Asp Leu Lys Thr Gln Ser Gly Ser Glu Met Lys Lys Phe
            275                 280                 285 ttg agc acc tta act ata gat ggt gta acc cgg agt gac caa gga ttg    912
Leu Ser Thr Leu Thr Ile Asp Gly Val Thr Arg Ser Asp Gln Gly Leu
        290                 295                 300 tac acc tgt gca gca tcc agt ggg ctg atg acc aag aag aac agc aca    960
Tyr Thr Cys Ala Ala Ser Ser Gly Leu Met Thr Lys Lys Asn Ser Thr
305                 310                 315                 320 ttt gtc agg gtc cat gaa aaa cct ttt gtt gct ttt gga agt ggc atg   1008
Phe Val Arg Val His Glu Lys Pro Phe Val Ala Phe Gly Ser Gly Met
            325                 330                 335 gaa tct ctg gtg gaa gcc acg gtg ggg gag cgt gtc aga atc cct gcg   1056
Glu Ser Leu Val Glu Ala Thr Val Gly Glu Arg Val Arg Ile Pro Ala
        340                 345                 350 aag tac ctt ggt tac cca ccc cca gaa ata aaa tgg tat aaa aat gga   1104
Lys Tyr Leu Gly Tyr Pro Pro Pro Glu Ile Lys Trp Tyr Lys Asn Gly
            355                 360                 365 ata ccc ctt gag tcc aat cac aca att aaa gcg ggg cat gta ctg acg   1152
Ile Pro Leu Glu Ser Asn His Thr Ile Lys Ala Gly His Val Leu Thr
        370                 375                 380 att atg gaa gtg agt gaa aga gac aca gga aat tac act gtc atc ctt   1200
Ile Met Glu Val Ser Glu Arg Asp Thr Gly Asn Tyr Thr Val Ile Leu
385                 390                 395                 400 acc aat ccc att tca aag gag aag cag agc cat gtg gtc tct ctg gtt   1248
Thr Asn Pro Ile Ser Lys Glu Lys Gln Ser His Val Val Ser Leu Val
            405                 410                 415 gtg tat gtc cca ccc cag att ggt gag aaa tct cta atc tct cct gtg   1296
Val Tyr Val Pro Pro Gln Ile Gly Glu Lys Ser Leu Ile Ser Pro Val
        420                 425                 430 gat tcc tac cag tac ggc acc act caa acg ctg aca tgt acg gtc tat   1344
Asp Ser Tyr Gln Tyr Gly Thr Thr Gln Thr Leu Thr Cys Thr Val Tyr
            435                 440                 445 gcc att cct ccc ccg cat cac atc cac tgg tat tgg cag ttg gag gaa   1392
Ala Ile Pro Pro Pro His His Ile His Trp Tyr Trp Gln Leu Glu Glu
450                 455                 460 gag tgc gcc aac gag ccc agc caa gct gtc tca gtg aca aac cca tac   1440
Glu Cys Ala Asn Glu Pro Ser Gln Ala Val Ser Val Thr Asn Pro Tyr
            465                 470                 475                 480 cct tgt gaa gaa tgg aga agt gtg gag gac ttc cag gga gga aat aaa   1488
Pro Cys Glu Glu Trp Arg Ser Val Glu Asp Phe Gln Gly Gly Asn Lys
```

```
                        485                 490                 495
att gaa gtt aat aaa aat caa ttt gct cta att gaa gga aaa aac aaa      1536
Ile Glu Val Asn Lys Asn Gln Phe Ala Leu Ile Glu Gly Lys Asn Lys
            500                 505                 510 act gta agt acc ctt gtt atc caa gcg gca aat gtg tca gct ttg tac      1584
Thr Val Ser Thr Leu Val Ile Gln Ala Ala Asn Val Ser Ala Leu Tyr
        515                 520                 525 aaa tgt gaa gcg gtc aac aaa gtc ggg aga gga gag agg gtg atc tcc      1632
Lys Cys Glu Ala Val Asn Lys Val Gly Arg Gly Glu Arg Val Ile Ser
    530                 535                 540 ttc cac gtg acc agg ggt cct gaa att act ttg caa cct gac atg cag      1680
Phe His Val Thr Arg Gly Pro Glu Ile Thr Leu Gln Pro Asp Met Gln
545                 550                 555                 560 ccc act gag cag gag agc gtg tct ttg tgg tgc act gca gac aga tct      1728
Pro Thr Glu Gln Glu Ser Val Ser Leu Trp Cys Thr Ala Asp Arg Ser
                565                 570                 575 acg ttt gag aac ctc aca tgg tac aag ctt ggc cca cag cct ctg cca      1776
Thr Phe Glu Asn Leu Thr Trp Tyr Lys Leu Gly Pro Gln Pro Leu Pro
            580                 585                 590 atc cat gtg gga gag ttg ccc aca cct gtt tgc aag aac ttg gat act      1824
Ile His Val Gly Glu Leu Pro Thr Pro Val Cys Lys Asn Leu Asp Thr
        595                 600                 605 ctt tgg aaa ttg aat gcc acc atg ttc tct aat agc aca aat gac att      1872
Leu Trp Lys Leu Asn Ala Thr Met Phe Ser Asn Ser Thr Asn Asp Ile
    610                 615                 620 ttg atc atg gag ctt aag aat gca tcc ttg cag gac caa gga gac tat      1920
Leu Ile Met Glu Leu Lys Asn Ala Ser Leu Gln Asp Gln Gly Asp Tyr
625                 630                 635                 640 gtc tgc ctt gct caa gac agg aag acc aag aaa aga cat tgc gtg gtc      1968
Val Cys Leu Ala Gln Asp Arg Lys Thr Lys Lys Arg His Cys Val Val
                645                 650                 655 agg cag ctc aca gtc cta gag cgt gtg gca ccc acg atc aca gga aac      2016
Arg Gln Leu Thr Val Leu Glu Arg Val Ala Pro Thr Ile Thr Gly Asn
            660                 665                 670 ctg gag aat cag acg aca agt att ggg gaa agc atc gaa gtc tca tgc      2064
Leu Glu Asn Gln Thr Thr Ser Ile Gly Glu Ser Ile Glu Val Ser Cys
        675                 680                 685 acg gca tct ggg aat ccc cct cca cag atc atg tgg ttt aaa gat aat      2112
Thr Ala Ser Gly Asn Pro Pro Pro Gln Ile Met Trp Phe Lys Asp Asn
    690                 695                 700 gag acc ctt gta gaa gac tca ggc att gta ttg aag gat ggg aac cgg      2160
Glu Thr Leu Val Glu Asp Ser Gly Ile Val Leu Lys Asp Gly Asn Arg
705                 710                 715                 720 aac ctc act atc cgc aga gtg agg aag gag gac gaa ggc ctc tac acc      2208
Asn Leu Thr Ile Arg Arg Val Arg Lys Glu Asp Glu Gly Leu Tyr Thr
                725                 730                 735 tgc cag gca tgc agt gtt ctt ggc tgt gca aaa gtg gag gca ttt ttc      2256
Cys Gln Ala Cys Ser Val Leu Gly Cys Ala Lys Val Glu Ala Phe Phe
            740                 745                 750 ata ata gaa ggt gcc cag gaa aag acg aac ttg gaa                      2292
Ile Ile Glu Gly Ala Gln Glu Lys Thr Asn Leu Glu
        755                 760

<210> SEQ ID NO 37
<211> LENGTH: 764
<212> TYPE: PRT
<213> ORGANISM: Homo sapiens

<400> SEQUENCE: 37

Met Glu Ser Lys Val Leu Leu Ala Val Ala Leu Trp Leu Cys Val Glu
```

-continued

```
1               5                   10                  15
Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
            35                  40                  45

Leu Gln Ile Thr Cys Arg Gly Gln Arg Asp Leu Asp Trp Leu Trp Pro
 50                  55                  60

Asn Asn Gln Ser Gly Ser Glu Gln Arg Val Glu Val Thr Glu Cys Ser
 65                  70                  75                  80

Asp Gly Leu Phe Cys Lys Thr Leu Thr Ile Pro Lys Val Ile Gly Asn
                 85                  90                  95

Asp Thr Gly Ala Tyr Lys Cys Phe Tyr Arg Glu Thr Asp Leu Ala Ser
                100                 105                 110

Val Ile Tyr Val Tyr Val Gln Asp Tyr Arg Ser Pro Phe Ile Ala Ser
            115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
                180                 185                 190

Ser Tyr Ala Gly Met Val Phe Cys Glu Ala Lys Ile Asn Asp Glu Ser
            195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
                260                 265                 270

Val Asn Arg Asp Leu Lys Thr Gln Ser Gly Ser Glu Met Lys Lys Phe
            275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Glu Ile Lys Trp Tyr Lys Asn Gly
    355                 360                 365

Ile Pro Leu Glu Ser Asn His Thr Ile Lys Ala Gly His Val Leu Thr
            370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430
```

```
Asp Ser Tyr Gln Tyr Gly Thr Thr Gln Thr Leu Thr Cys Thr Val Tyr
        435                 440                 445

Ala Ile Pro Pro His His Ile His Trp Tyr Trp Gln Leu Glu Glu
    450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Asp Phe Gln Gly Gly Asn Lys
            485                 490                 495

Ile Glu Val Asn Lys Asn Gln Phe Ala Leu Ile Glu Gly Lys Asn Lys
                500                 505                 510

Thr Val Ser Thr Leu Val Ile Gln Ala Ala Asn Val Ser Ala Leu Tyr
                515                 520                 525

Lys Cys Glu Ala Val Asn Lys Val Gly Arg Gly Glu Arg Val Ile Ser
    530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
                580                 585                 590

Ile His Val Gly Glu Leu Pro Thr Pro Val Cys Lys Asn Leu Asp Thr
    595                 600                 605

Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
                660                 665                 670

Leu Glu Asn Gln Thr Thr Ser Ile Gly Glu Ser Ile Glu Val Ser Cys
                675                 680                 685

Thr Ala Ser Gly Asn Pro Pro Pro Gln Ile Met Trp Phe Lys Asp Asn
    690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
                740                 745                 750

Ile Ile Glu Gly Ala Gln Glu Lys Thr Asn Leu Glu
        755                 760

<210> SEQ ID NO 38
<211> LENGTH: 4195
<212> TYPE: DNA
<213> ORGANISM: Homo sapiens
<220> FEATURE:
<221> NAME/KEY: CDS
<222> LOCATION: (20)..(3913)

<400> SEQUENCE: 38
ccacgcgcag cggccggag atg cag cgg ggc gcc gcg ctg tgc ctg cga ctg      52
                     Met Gln Arg Gly Ala Ala Leu Cys Leu Arg Leu
                      1               5                  10
```

-continued

| | |
|---|---:|
| tgg ctc tgc ctg gga ctc ctg gac ggc ctg gtg agt ggc tac tcc atg<br>Trp Leu Cys Leu Gly Leu Leu Asp Gly Leu Val Ser Gly Tyr Ser Met<br>15            20             25 | 100 |
| acc ccc ccg acc ttg aac atc acg gag gag tca cac gtc atc gac acc<br>Thr Pro Pro Thr Leu Asn Ile Thr Glu Glu Ser His Val Ile Asp Thr<br>    30              35              40 | 148 |
| ggt gac agc ctg tcc atc tcc tgc agg gga cag cac ccc ctc gag tgg<br>Gly Asp Ser Leu Ser Ile Ser Cys Arg Gly Gln His Pro Leu Glu Trp<br>45              50              55 | 196 |
| gct tgg cca gga gct cag gag gcg cca gcc acc gga gac aag gac agc<br>Ala Trp Pro Gly Ala Gln Glu Ala Pro Ala Thr Gly Asp Lys Asp Ser<br>60              65              70              75 | 244 |
| gag gac acg ggg gtg gtg cga gac tgc gag ggc aca gac gcc agg ccc<br>Glu Asp Thr Gly Val Val Arg Asp Cys Glu Gly Thr Asp Ala Arg Pro<br>    80              85              90 | 292 |
| tac tgc aag gtg ttg ctg ctg cac gag gta cat gcc aac gac aca ggc<br>Tyr Cys Lys Val Leu Leu Leu His Glu Val His Ala Asn Asp Thr Gly<br>95              100             105 | 340 |
| agc tac gtc tgc tac tac aag tac atc aag gca cgc atc gag ggc acc<br>Ser Tyr Val Cys Tyr Tyr Lys Tyr Ile Lys Ala Arg Ile Glu Gly Thr<br>    110             115             120 | 388 |
| acg gcc gcc agc tcc tac gtg ttc gtg aga gac ttt gag cag cca ttc<br>Thr Ala Ala Ser Ser Tyr Val Phe Val Arg Asp Phe Glu Gln Pro Phe<br>125             130             135 | 436 |
| atc aac aag cct gac acg ctc ttg gtc aac agg aag gac gcc atg tgg<br>Ile Asn Lys Pro Asp Thr Leu Leu Val Asn Arg Lys Asp Ala Met Trp<br>140             145             150             155 | 484 |
| gtg ccc tgt ctg gtg tcc atc ccc ggc ctc aat gtc acg ctg cgc tcg<br>Val Pro Cys Leu Val Ser Ile Pro Gly Leu Asn Val Thr Leu Arg Ser<br>    160             165             170 | 532 |
| caa agc tcg gtg ctg tgg cca gac ggg cag gag gtg gtg tgg gat gac<br>Gln Ser Ser Val Leu Trp Pro Asp Gly Gln Glu Val Val Trp Asp Asp<br>175             180             185 | 580 |
| cgg cgg ggc atg ctc gtg tcc acg cca ctg ctg cac gat gcc ctg tac<br>Arg Arg Gly Met Leu Val Ser Thr Pro Leu Leu His Asp Ala Leu Tyr<br>    190             195             200 | 628 |
| ctg cag tgc gag acc acc tgg gga gac cag gac ttc ctt tcc aac ccc<br>Leu Gln Cys Glu Thr Thr Trp Gly Asp Gln Asp Phe Leu Ser Asn Pro<br>205             210             215 | 676 |
| ttc ctg gtg cac atc aca ggc aac gag ctc tat gac atc cag ctg ttg<br>Phe Leu Val His Ile Thr Gly Asn Glu Leu Tyr Asp Ile Gln Leu Leu<br>220             225             230             235 | 724 |
| ccc agg aag tcg ctg gag ctg ctg gta ggg gag aag ctg gtc ctg aac<br>Pro Arg Lys Ser Leu Glu Leu Leu Val Gly Glu Lys Leu Val Leu Asn<br>    240             245             250 | 772 |
| tgc acc gtg tgg gct gag ttt aac tca ggt gtc acc ttt gac tgg gac<br>Cys Thr Val Trp Ala Glu Phe Asn Ser Gly Val Thr Phe Asp Trp Asp<br>255             260             265 | 820 |
| tac cca ggg aag cag gca gag cgg ggt aag tgg gtg ccc gag cga cgc<br>Tyr Pro Gly Lys Gln Ala Glu Arg Gly Lys Trp Val Pro Glu Arg Arg<br>    270             275             280 | 868 |
| tcc cag cag acc cac aca gaa ctc tcc agc atc ctg acc atc cac aac<br>Ser Gln Gln Thr His Thr Glu Leu Ser Ser Ile Leu Thr Ile His Asn<br>285             290             295 | 916 |
| gtc agc cag cac gac ctg ggc tcg tat gtg tgc aag gcc aac aac ggc<br>Val Ser Gln His Asp Leu Gly Ser Tyr Val Cys Lys Ala Asn Asn Gly<br>300             305             310             315 | 964 |
| atc cag cga ttt cgg gag agc acc gag gtc att gtg cat gaa aat ccc<br>Ile Gln Arg Phe Arg Glu Ser Thr Glu Val Ile Val His Glu Asn Pro<br>    320             325             330 | 1012 |

-continued

```
ttc atc agc gtc gag tgg ctc aaa gga ccc atc ctg gag gcc acg gca        1060
Phe Ile Ser Val Glu Trp Leu Lys Gly Pro Ile Leu Glu Ala Thr Ala
            335                 340                 345 gga gac gag ctg gtg aag ctg ccc gtg aag ctg gcg tac ccc ccg            1108
Gly Asp Glu Leu Val Lys Leu Pro Val Lys Leu Ala Ala Tyr Pro Pro
        350                 355                 360 ccc gag ttc cag tgg tac aag gat gga aag gca ctg tcc ggg cgc cac        1156
Pro Glu Phe Gln Trp Tyr Lys Asp Gly Lys Ala Leu Ser Gly Arg His
    365                 370                 375 agt cca cat gcc ctg gtg ctc aag gag gtg aca gag gcc agc aca ggc        1204
Ser Pro His Ala Leu Val Leu Lys Glu Val Thr Glu Ala Ser Thr Gly
380                 385                 390                 395 acc tac acc ctc gcc ctg tgg aac tcc gct gct ggc ctg agg cgc aac        1252
Thr Tyr Thr Leu Ala Leu Trp Asn Ser Ala Ala Gly Leu Arg Arg Asn
            400                 405                 410 atc agc ctg gag ctg gtg gtg aat gtg ccc ccc cag ata cat gag aag        1300
Ile Ser Leu Glu Leu Val Val Asn Val Pro Pro Gln Ile His Glu Lys
        415                 420                 425 gag gcc tcc tcc ccc agc atc tac tcg cgt cac agc cgc cag gcc ctc        1348
Glu Ala Ser Ser Pro Ser Ile Tyr Ser Arg His Ser Arg Gln Ala Leu
    430                 435                 440 acc tgc acg gcc tac ggg gtg ccc ctg cct ctc agc atc cag tgg cac        1396
Thr Cys Thr Ala Tyr Gly Val Pro Leu Pro Leu Ser Ile Gln Trp His
445                 450                 455 tgg cgg ccc tgg aca ccc tgc aag atg ttt gcc cag cgt agt ctc cgg        1444
Trp Arg Pro Trp Thr Pro Cys Lys Met Phe Ala Gln Arg Ser Leu Arg
460                 465                 470                 475 cgg cgg cag cag caa gac ctc atg cca cag tgc cgt gac tgg agg gcg        1492
Arg Arg Gln Gln Gln Asp Leu Met Pro Gln Cys Arg Asp Trp Arg Ala
            480                 485                 490 gtg acc acg cag gat gcc gtg aac ccc atc gag agc ctg gac acc tgg        1540
Val Thr Thr Gln Asp Ala Val Asn Pro Ile Glu Ser Leu Asp Thr Trp
        495                 500                 505 acc gag ttt gtg gag gga aag aat aag act gtg agc aag ctg gtg atc        1588
Thr Glu Phe Val Glu Gly Lys Asn Lys Thr Val Ser Lys Leu Val Ile
    510                 515                 520 cag aat gcc aac gtg tct gcc atg tac aag tgt gtg gtc tcc aac aag        1636
Gln Asn Ala Asn Val Ser Ala Met Tyr Lys Cys Val Val Ser Asn Lys
525                 530                 535 gtg ggc cag gat gag cgg ctc atc tac ttc tat gtg acc acc atc ccc        1684
Val Gly Gln Asp Glu Arg Leu Ile Tyr Phe Tyr Val Thr Thr Ile Pro
540                 545                 550                 555 gac ggc ttc acc atc gaa tcc aag cca tcc gag gag cta cta gag ggc        1732
Asp Gly Phe Thr Ile Glu Ser Lys Pro Ser Glu Glu Leu Leu Glu Gly
            560                 565                 570 cag ccg gtg ctc ctg agc tgc caa gcc gac agc tac aag tac gag cat        1780
Gln Pro Val Leu Leu Ser Cys Gln Ala Asp Ser Tyr Lys Tyr Glu His
        575                 580                 585 ctg cgc tgg tac cgc ctc aac ctg tcc acg ctg cac gat gcg cac ggg        1828
Leu Arg Trp Tyr Arg Leu Asn Leu Ser Thr Leu His Asp Ala His Gly
    590                 595                 600 aac ccg ctt ctg ctc gac tgc aag aac gtg cat ctg ttc gcc acc cct        1876
Asn Pro Leu Leu Leu Asp Cys Lys Asn Val His Leu Phe Ala Thr Pro
605                 610                 615 ctg gcc gcc agc ctg gag gag gtg gca cct ggg gcg cgc cac gcc acg        1924
Leu Ala Ala Ser Leu Glu Glu Val Ala Pro Gly Ala Arg His Ala Thr
620                 625                 630                 635 ctc agc ctg agt atc ccc cgc gtc gcg ccc gag cac gag ggc cac tat        1972
Leu Ser Leu Ser Ile Pro Arg Val Ala Pro Glu His Glu Gly His Tyr
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 640 |     |     |     |     | 645 |     |     |     |     | 650 |     |      |
| gtg | tgc | gaa | gtg | caa | gac | cgg | cgc | agc | cat | gac | aag | cac | tgc | cac | aag | 2020 |
| Val | Cys | Glu | Val | Gln | Asp | Arg | Arg | Ser | His | Asp | Lys | His | Cys | His | Lys |      |
|     |     |     |     | 655 |     |     |     |     | 660 |     |     |     |     | 665 |     |      |
| aag | tac | ctg | tcg | gtg | cag | gcc | ctg | gaa | gcc | cct | cgg | ctc | acg | cag | aac | 2068 |
| Lys | Tyr | Leu | Ser | Val | Gln | Ala | Leu | Glu | Ala | Pro | Arg | Leu | Thr | Gln | Asn |      |
|     |     |     |     | 670 |     |     |     |     | 675 |     |     |     |     | 680 |     |      |
| ttg | acc | gac | ctc | ctg | gtg | aac | gtg | agc | gac | tcg | ctg | gag | atg | cag | tgc | 2116 |
| Leu | Thr | Asp | Leu | Leu | Val | Asn | Val | Ser | Asp | Ser | Leu | Glu | Met | Gln | Cys |      |
|     |     |     | 685 |     |     |     |     | 690 |     |     |     |     | 695 |     |     |      |
| ttg | gtg | gcc | gga | gcg | cac | gcg | ccc | agc | atc | gtg | tgg | tac | aaa | gac | gag | 2164 |
| Leu | Val | Ala | Gly | Ala | His | Ala | Pro | Ser | Ile | Val | Trp | Tyr | Lys | Asp | Glu |      |
| 700 |     |     |     |     | 705 |     |     |     |     | 710 |     |     |     |     | 715 |      |
| agg | ctg | ctg | gag | gaa | aag | tct | gga | gtc | gac | ttg | gcg | gac | tcc | aac | cag | 2212 |
| Arg | Leu | Leu | Glu | Glu | Lys | Ser | Gly | Val | Asp | Leu | Ala | Asp | Ser | Asn | Gln |      |
|     |     |     |     | 720 |     |     |     |     | 725 |     |     |     |     | 730 |     |      |
| aag | ctg | agc | atc | cag | cgc | gtg | cgc | gag | gag | gat | gcg | gga | cgc | tat | ctg | 2260 |
| Lys | Leu | Ser | Ile | Gln | Arg | Val | Arg | Glu | Glu | Asp | Ala | Gly | Arg | Tyr | Leu |      |
|     |     |     | 735 |     |     |     |     | 740 |     |     |     |     | 745 |     |     |      |
| tgc | agc | gtg | tgc | aac | gcc | aag | ggc | tgc | gtc | aac | tcc | tcc | gcc | agc | gtg | 2308 |
| Cys | Ser | Val | Cys | Asn | Ala | Lys | Gly | Cys | Val | Asn | Ser | Ser | Ala | Ser | Val |      |
|     |     | 750 |     |     |     |     | 755 |     |     |     |     | 760 |     |     |     |      |
| gcc | gtg | gaa | ggc | tcc | gag | gat | aag | ggc | agc | atg | gag | atc | gtg | atc | ctt | 2356 |
| Ala | Val | Glu | Gly | Ser | Glu | Asp | Lys | Gly | Ser | Met | Glu | Ile | Val | Ile | Leu |      |
|     | 765 |     |     |     |     | 770 |     |     |     |     | 775 |     |     |     |     |      |
| gtc | ggt | acc | ggc | gtc | atc | gct | gtc | ttc | ttc | tgg | gtc | ctc | ctc | ctc | ctc | 2404 |
| Val | Gly | Thr | Gly | Val | Ile | Ala | Val | Phe | Phe | Trp | Val | Leu | Leu | Leu | Leu |      |
| 780 |     |     |     |     | 785 |     |     |     |     | 790 |     |     |     |     | 795 |      |
| atc | ttc | tgt | aac | atg | agg | agg | ccg | gcc | cac | gca | gac | atc | aag | acg | ggc | 2452 |
| Ile | Phe | Cys | Asn | Met | Arg | Arg | Pro | Ala | His | Ala | Asp | Ile | Lys | Thr | Gly |      |
|     |     |     |     | 800 |     |     |     |     | 805 |     |     |     |     | 810 |     |      |
| tac | ctg | tcc | atc | atc | atg | gac | ccc | ggg | gag | gtg | cct | ctg | gag | gag | caa | 2500 |
| Tyr | Leu | Ser | Ile | Ile | Met | Asp | Pro | Gly | Glu | Val | Pro | Leu | Glu | Glu | Gln |      |
|     |     |     | 815 |     |     |     |     | 820 |     |     |     |     | 825 |     |     |      |
| tgc | gaa | tac | ctg | tcc | tac | gat | gcc | agc | cag | tgg | gaa | ttc | ccc | cga | gag | 2548 |
| Cys | Glu | Tyr | Leu | Ser | Tyr | Asp | Ala | Ser | Gln | Trp | Glu | Phe | Pro | Arg | Glu |      |
|     |     | 830 |     |     |     |     | 835 |     |     |     |     | 840 |     |     |     |      |
| cgg | ctg | cac | ctg | ggg | aga | gtg | ctc | ggc | tac | ggc | gcc | ttc | ggg | aag | gtg | 2596 |
| Arg | Leu | His | Leu | Gly | Arg | Val | Leu | Gly | Tyr | Gly | Ala | Phe | Gly | Lys | Val |      |
|     | 845 |     |     |     |     | 850 |     |     |     |     | 855 |     |     |     |     |      |
| gtg | gaa | gcc | tcc | gct | ttc | ggc | atc | cac | aag | ggc | agc | agc | tgt | gac | acc | 2644 |
| Val | Glu | Ala | Ser | Ala | Phe | Gly | Ile | His | Lys | Gly | Ser | Ser | Cys | Asp | Thr |      |
| 860 |     |     |     |     | 865 |     |     |     |     | 870 |     |     |     |     | 875 |      |
| gtg | gcc | gtg | aaa | atg | ctg | aaa | gag | ggc | gcc | acg | gcc | agc | gag | cac | cgc | 2692 |
| Val | Ala | Val | Lys | Met | Leu | Lys | Glu | Gly | Ala | Thr | Ala | Ser | Glu | His | Arg |      |
|     |     |     |     | 880 |     |     |     |     | 885 |     |     |     |     | 890 |     |      |
| gcg | ctg | atg | tcg | gag | ctc | aag | atc | ctc | att | cac | atc | ggc | aac | cac | ctc | 2740 |
| Ala | Leu | Met | Ser | Glu | Leu | Lys | Ile | Leu | Ile | His | Ile | Gly | Asn | His | Leu |      |
|     |     |     | 895 |     |     |     |     | 900 |     |     |     |     | 905 |     |     |      |
| aac | gtg | gtc | aac | ctc | ctc | ggg | gcg | tgc | acc | aag | ccg | cag | ggc | ccc | ctc | 2788 |
| Asn | Val | Val | Asn | Leu | Leu | Gly | Ala | Cys | Thr | Lys | Pro | Gln | Gly | Pro | Leu |      |
|     |     | 910 |     |     |     |     | 915 |     |     |     |     | 920 |     |     |     |      |
| atg | gtg | atc | gtg | gag | ttc | tgc | aag | tac | ggc | aac | ctc | tcc | aac | ttc | ctg | 2836 |
| Met | Val | Ile | Val | Glu | Phe | Cys | Lys | Tyr | Gly | Asn | Leu | Ser | Asn | Phe | Leu |      |
|     | 925 |     |     |     |     | 930 |     |     |     |     | 935 |     |     |     |     |      |
| cgc | gcc | aag | cgg | gac | gcc | ttc | agc | ccc | tgc | gcg | gag | aag | tct | ccc | gag | 2884 |
| Arg | Ala | Lys | Arg | Asp | Ala | Phe | Ser | Pro | Cys | Ala | Glu | Lys | Ser | Pro | Glu |      |
| 940 |     |     |     |     | 945 |     |     |     |     | 950 |     |     |     |     | 955 |      |
| cag | cgc | gga | cgc | ttc | cgc | gcc | atg | gtg | gag | ctc | gcc | agg | ctg | gat | cgg | 2932 |
| Gln | Arg | Gly | Arg | Phe | Arg | Ala | Met | Val | Glu | Leu | Ala | Arg | Leu | Asp | Arg |      |

-continued

| | | | | | | | | | | | | | | |
|---|---|---|---|---|---|---|---|---|---|---|---|---|---|---|
| Gln | Arg | Gly | Arg | Phe | Arg | Ala | Met | Val | Glu | Leu | Ala | Arg | Leu | Asp | Arg |
| | | | | 960 | | | | 965 | | | | | 970 | | |

```
agg  cgg  ccg  ggg  agc  agc  gac  agg  gtc  ctc  ttc  gcg  cgg  ttc  tcg  aag       2980
Arg  Arg  Pro  Gly  Ser  Ser  Asp  Arg  Val  Leu  Phe  Ala  Arg  Phe  Ser  Lys
               975                     980                     985 acc  gag  ggc  gga  gcg  agg  cgg  gct  tct  cca  gac  caa  gaa  gct  gag  gac       3028
Thr  Glu  Gly  Gly  Ala  Arg  Arg  Ala  Ser  Pro  Asp  Gln  Glu  Ala  Glu  Asp
               990                     995                    1000 ctg  tgg  ctg  agc  ccg  ctg  acc  atg  gaa  gat  ctt  gtc  tgc  tac  agc            3073
Leu  Trp  Leu  Ser  Pro  Leu  Thr  Met  Glu  Asp  Leu  Val  Cys  Tyr  Ser
              1005                    1010                   1015 ttc  cag  gtg  gcc  aga  ggg  atg  gag  ttc  ctg  gct  tcc  cga  aag  tgc            3118
Phe  Gln  Val  Ala  Arg  Gly  Met  Glu  Phe  Leu  Ala  Ser  Arg  Lys  Cys
        1020                    1025                    1030 atc  cac  aga  gac  ctg  gct  gct  cgg  aac  att  ctg  ctg  tcg  gaa  agc            3163
Ile  His  Arg  Asp  Leu  Ala  Ala  Arg  Asn  Ile  Leu  Leu  Ser  Glu  Ser
        1035                    1040                    1045 gac  gtg  gtg  aag  atc  tgt  gac  ttt  ggc  ctt  gcc  cgg  gac  atc  tac            3208
Asp  Val  Val  Lys  Ile  Cys  Asp  Phe  Gly  Leu  Ala  Arg  Asp  Ile  Tyr
        1050                    1055                    1060 aaa  gac  cct  gac  tac  gtc  cgc  aag  ggc  agt  gcc  cgg  ctg  ccc  ctg            3253
Lys  Asp  Pro  Asp  Tyr  Val  Arg  Lys  Gly  Ser  Ala  Arg  Leu  Pro  Leu
        1065                    1070                    1075 aag  tgg  atg  gcc  cct  gaa  agc  atc  ttc  gac  aag  gtg  tac  acc  acg            3298
Lys  Trp  Met  Ala  Pro  Glu  Ser  Ile  Phe  Asp  Lys  Val  Tyr  Thr  Thr
        1080                    1085                    1090 cag  agt  gac  gtg  tgg  tcc  ttt  ggg  gtg  ctt  ctc  tgg  gag  atc  ttc            3343
Gln  Ser  Asp  Val  Trp  Ser  Phe  Gly  Val  Leu  Leu  Trp  Glu  Ile  Phe
        1095                    1100                    1105 tct  ctg  ggg  gcc  tcc  ccg  tac  cct  ggg  gtg  cag  atc  aat  gag  gag            3388
Ser  Leu  Gly  Ala  Ser  Pro  Tyr  Pro  Gly  Val  Gln  Ile  Asn  Glu  Glu
        1110                    1115                    1120 ttc  tgc  cag  cgg  ctg  aga  gac  ggc  aca  agg  atg  agg  gcc  ccg  gag            3433
Phe  Cys  Gln  Arg  Leu  Arg  Asp  Gly  Thr  Arg  Met  Arg  Ala  Pro  Glu
        1125                    1130                    1135 ctg  gcc  act  ccc  gcc  ata  cgc  cgc  atc  atg  ctg  aac  tgc  tgg  tcc            3478
Leu  Ala  Thr  Pro  Ala  Ile  Arg  Arg  Ile  Met  Leu  Asn  Cys  Trp  Ser
        1140                    1145                    1150 gga  gac  ccc  aag  gcg  aga  cct  gca  ttc  tcg  gag  ctg  gtg  gag  atc            3523
Gly  Asp  Pro  Lys  Ala  Arg  Pro  Ala  Phe  Ser  Glu  Leu  Val  Glu  Ile
        1155                    1160                    1165 ctg  ggg  gac  ctg  ctc  cag  ggc  agg  ggc  ctg  caa  gag  gaa  gag  gag            3568
Leu  Gly  Asp  Leu  Leu  Gln  Gly  Arg  Gly  Leu  Gln  Glu  Glu  Glu  Glu
        1170                    1175                    1180 gtc  tgc  atg  gcc  ccg  cgc  agc  tct  cag  agc  tca  gaa  gag  ggc  agc            3613
Val  Cys  Met  Ala  Pro  Arg  Ser  Ser  Gln  Ser  Ser  Glu  Glu  Gly  Ser
        1185                    1190                    1195 ttc  tcg  cag  gtg  tcc  acc  atg  gcc  cta  cac  atc  gcc  cag  gct  gac            3658
Phe  Ser  Gln  Val  Ser  Thr  Met  Ala  Leu  His  Ile  Ala  Gln  Ala  Asp
        1200                    1205                    1210 gct  gag  gac  agc  ccg  cca  agc  ctg  cag  cgc  cac  agc  ctg  gcc  gcc            3703
Ala  Glu  Asp  Ser  Pro  Pro  Ser  Leu  Gln  Arg  His  Ser  Leu  Ala  Ala
        1215                    1220                    1225 agg  tat  tac  aac  tgg  gtg  tcc  ttt  ccc  ggg  tgc  ctg  gcc  aga  ggg            3748
Arg  Tyr  Tyr  Asn  Trp  Val  Ser  Phe  Pro  Gly  Cys  Leu  Ala  Arg  Gly
        1230                    1235                    1240 gct  gag  acc  cgt  ggt  tcc  tcc  agg  atg  aag  aca  ttt  gag  gaa  ttc            3793
Ala  Glu  Thr  Arg  Gly  Ser  Ser  Arg  Met  Lys  Thr  Phe  Glu  Glu  Phe
        1245                    1250                    1255
```

```
ccc atg acc cca acg acc tac aaa ggc tct gtg gac aac cag aca      3838
Pro Met Thr Pro Thr Thr Tyr Lys Gly Ser Val Asp Asn Gln Thr
    1260            1265                1270 gac agt ggg atg gtg ctg gcc tcg gag gag ttt gag cag ata gag      3883
Asp Ser Gly Met Val Leu Ala Ser Glu Glu Phe Glu Gln Ile Glu
1275            1280                1285 agc agg cat aga caa gaa agc ggc ttc agg tagctgaagc agagagagag    3933
Ser Arg His Arg Gln Glu Ser Gly Phe Arg
1290            1295 aaggcagcat acgtcagcat tttcttctct gcacttataa gaaagatcaa agactttaag   3993
actttcgcta tttcttctac tgctatctac tacaaacttc aaagaggaac caggaggaca   4053
agaggagcat gaaagtggac aaggagtgtg accactgaag caccacaggg aaggggttag   4113
gcctccggat gactgcgggc aggcctggat aatatccagc ctcccacaag aagctggtgg   4173
agcagagtgt tccctgactc ct                                           4195
```

<210> SEQ ID NO 39
<211> LENGTH: 1298
<212> TYPE: PRT
<213> ORGANISM: Homo sapiens

<400> SEQUENCE: 39

```
Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
    210                 215                 220

Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
                245                 250                 255

Glu Phe Asn Ser Gly Val Thr Phe Asp Trp Asp Tyr Pro Gly Lys Gln
```

```
                260             265             270
Ala Glu Arg Gly Lys Trp Val Pro Glu Arg Ser Gln Gln Thr His
            275             280             285

Thr Glu Leu Ser Ser Ile Leu Thr Ile His Asn Val Ser Gln His Asp
        290             295             300

Leu Gly Ser Tyr Val Cys Lys Ala Asn Asn Gly Ile Gln Arg Phe Arg
305             310             315             320

Glu Ser Thr Glu Val Ile Val His Glu Asn Pro Phe Ile Ser Val Glu
                325             330             335

Trp Leu Lys Gly Pro Ile Leu Glu Ala Thr Ala Gly Asp Glu Leu Val
            340             345             350

Lys Leu Pro Val Lys Leu Ala Ala Tyr Pro Pro Glu Phe Gln Trp
        355             360             365

Tyr Lys Asp Gly Lys Ala Leu Ser Gly Arg His Ser Pro His Ala Leu
        370             375             380

Val Leu Lys Glu Val Thr Glu Ala Ser Thr Gly Thr Tyr Thr Leu Ala
385             390             395             400

Leu Trp Asn Ser Ala Ala Gly Leu Arg Arg Asn Ile Ser Leu Glu Leu
            405             410             415

Val Val Asn Val Pro Pro Gln Ile His Glu Lys Glu Ala Ser Ser Pro
        420             425             430

Ser Ile Tyr Ser Arg His Ser Arg Gln Ala Leu Thr Cys Thr Ala Tyr
        435             440             445

Gly Val Pro Leu Pro Leu Ser Ile Gln Trp His Trp Arg Pro Trp Thr
    450             455             460

Pro Cys Lys Met Phe Ala Gln Arg Ser Leu Arg Arg Arg Gln Gln Gln
465             470             475             480

Asp Leu Met Pro Gln Cys Arg Asp Trp Arg Ala Val Thr Thr Gln Asp
            485             490             495

Ala Val Asn Pro Ile Glu Ser Leu Asp Thr Trp Thr Glu Phe Val Glu
        500             505             510

Gly Lys Asn Lys Thr Val Ser Lys Leu Val Ile Gln Asn Ala Asn Val
        515             520             525

Ser Ala Met Tyr Lys Cys Val Val Ser Asn Lys Val Gly Gln Asp Glu
    530             535             540

Arg Leu Ile Tyr Phe Tyr Val Thr Thr Ile Pro Asp Gly Phe Thr Ile
545             550             555             560

Glu Ser Lys Pro Ser Glu Glu Leu Leu Glu Gly Gln Pro Val Leu Leu
            565             570             575

Ser Cys Gln Ala Asp Ser Tyr Lys Tyr Glu His Leu Arg Trp Tyr Arg
        580             585             590

Leu Asn Leu Ser Thr Leu His Asp Ala His Gly Asn Pro Leu Leu Leu
        595             600             605

Asp Cys Lys Asn Val His Leu Phe Ala Thr Pro Leu Ala Ala Ser Leu
    610             615             620

Glu Glu Val Ala Pro Gly Ala Arg His Ala Thr Leu Ser Leu Ser Ile
625             630             635             640

Pro Arg Val Ala Pro Glu His Glu Gly His Tyr Val Cys Glu Val Gln
            645             650             655

Asp Arg Arg Ser His Asp Lys His Cys His Lys Lys Tyr Leu Ser Val
        660             665             670

Gln Ala Leu Glu Ala Pro Arg Leu Thr Gln Asn Leu Thr Asp Leu Leu
        675             680             685
```

```
Val Asn Val Ser Asp Ser Leu Glu Met Gln Cys Leu Val Ala Gly Ala
    690             695                 700
His Ala Pro Ser Ile Val Trp Tyr Lys Asp Glu Arg Leu Leu Glu Glu
705                 710                 715                 720
Lys Ser Gly Val Asp Leu Ala Asp Ser Asn Gln Lys Leu Ser Ile Gln
                725                 730                 735
Arg Val Arg Glu Glu Asp Ala Gly Arg Tyr Leu Cys Ser Val Cys Asn
            740                 745                 750
Ala Lys Gly Cys Val Asn Ser Ser Ala Ser Val Ala Val Glu Gly Ser
        755                 760                 765
Glu Asp Lys Gly Ser Met Glu Ile Val Ile Leu Val Gly Thr Gly Val
    770                 775                 780
Ile Ala Val Phe Phe Trp Val Leu Leu Leu Leu Ile Phe Cys Asn Met
785                 790                 795                 800
Arg Arg Pro Ala His Ala Asp Ile Lys Thr Gly Tyr Leu Ser Ile Ile
                805                 810                 815
Met Asp Pro Gly Glu Val Pro Leu Glu Glu Gln Cys Glu Tyr Leu Ser
            820                 825                 830
Tyr Asp Ala Ser Gln Trp Glu Phe Pro Arg Glu Arg Leu His Leu Gly
        835                 840                 845
Arg Val Leu Gly Tyr Gly Ala Phe Gly Lys Val Val Glu Ala Ser Ala
    850                 855                 860
Phe Gly Ile His Lys Gly Ser Ser Cys Asp Thr Val Ala Val Lys Met
865                 870                 875                 880
Leu Lys Glu Gly Ala Thr Ala Ser Glu His Arg Ala Leu Met Ser Glu
                885                 890                 895
Leu Lys Ile Leu Ile His Ile Gly Asn His Leu Asn Val Asn Leu
            900                 905                 910
Leu Gly Ala Cys Thr Lys Pro Gln Gly Pro Leu Met Val Ile Val Glu
        915                 920                 925
Phe Cys Lys Tyr Gly Asn Leu Ser Asn Phe Leu Arg Ala Lys Arg Asp
    930                 935                 940
Ala Phe Ser Pro Cys Ala Glu Lys Ser Pro Gln Arg Gly Arg Phe
945                 950                 955                 960
Arg Ala Met Val Glu Leu Ala Arg Leu Asp Arg Arg Pro Gly Ser
                965                 970                 975
Ser Asp Arg Val Leu Phe Ala Arg Phe Ser Lys Thr Glu Gly Gly Ala
            980                 985                 990
Arg Arg Ala Ser Pro Asp Gln Glu  Ala Glu Asp Leu Trp  Leu Ser Pro
        995                 1000                1005
Leu Thr Met Glu Asp Leu Val  Cys Tyr Ser Phe Gln  Val Ala Arg
    1010                1015                1020
Gly Met  Glu Phe Leu Ala Ser  Arg Lys Cys Ile His  Arg Asp Leu
    1025                1030                1035
Ala Ala  Arg Asn Ile Leu Leu  Ser Glu Ser Asp Val  Val Lys Ile
        1040                1045                1050
Cys Asp  Phe Gly Leu Ala Arg  Asp Ile Tyr Lys Asp  Pro Asp Tyr
    1055                1060                1065
Val Arg  Lys Gly Ser Ala Arg  Leu Pro Leu Lys Trp  Met Ala Pro
    1070                1075                1080
Glu Ser  Ile Phe Asp Lys Val  Tyr Thr Thr Gln Ser  Asp Val Trp
    1085                1090                1095
```

-continued

```
Ser Phe Gly Val Leu Leu Trp Glu Ile Phe Ser Leu Gly Ala Ser
    1100                1105                1110

Pro Tyr Pro Gly Val Gln Ile Asn Glu Glu Phe Cys Gln Arg Leu
    1115                1120                1125

Arg Asp Gly Thr Arg Met Arg Ala Pro Glu Leu Ala Thr Pro Ala
    1130                1135                1140

Ile Arg Arg Ile Met Leu Asn Cys Trp Ser Gly Asp Pro Lys Ala
    1145                1150                1155

Arg Pro Ala Phe Ser Glu Leu Val Glu Ile Leu Gly Asp Leu Leu
    1160                1165                1170

Gln Gly Arg Gly Leu Gln Glu Glu Glu Val Cys Met Ala Pro
    1175                1180                1185

Arg Ser Ser Gln Ser Ser Glu Gly Ser Phe Ser Gln Val Ser
    1190                1195                1200

Thr Met Ala Leu His Ile Ala Gln Ala Asp Ala Glu Asp Ser Pro
    1205                1210                1215

Pro Ser Leu Gln Arg His Ser Leu Ala Ala Arg Tyr Tyr Asn Trp
    1220                1225                1230

Val Ser Phe Pro Gly Cys Leu Ala Arg Gly Ala Glu Thr Arg Gly
    1235                1240                1245

Ser Ser Arg Met Lys Thr Phe Glu Glu Phe Pro Met Thr Pro Thr
    1250                1255                1260

Thr Tyr Lys Gly Ser Val Asp Asn Gln Thr Asp Ser Gly Met Val
    1265                1270                1275

Leu Ala Ser Glu Glu Phe Glu Gln Ile Glu Ser Arg His Arg Gln
    1280                1285                1290

Glu Ser Gly Phe Arg
    1295

<210> SEQ ID NO 40
<211> LENGTH: 4795
<212> TYPE: DNA
<213> ORGANISM: Homo sapiens
<220> FEATURE:
<221> NAME/KEY: CDS
<222> LOCATION: (20)..(4111)

<400> SEQUENCE: 40
ccacgcgcag cggccggag atg cag cgg ggc gcc gcg ctg tgc ctg cga ctg       52
                    Met Gln Arg Gly Ala Ala Leu Cys Leu Arg Leu
                     1               5                  10 tgg ctc tgc ctg gga ctc ctg gac ggc ctg gtg agt ggc tac tcc atg      100
Trp Leu Cys Leu Gly Leu Leu Asp Gly Leu Val Ser Gly Tyr Ser Met
         15                  20                  25 acc ccc ccg acc ttg aac atc acg gag gag tca cac gtc atc gac acc      148
Thr Pro Pro Thr Leu Asn Ile Thr Glu Glu Ser His Val Ile Asp Thr
             30                  35                  40 ggt gac agc ctg tcc atc tcc tgc agg gga cag cac ccc ctc gag tgg      196
Gly Asp Ser Leu Ser Ile Ser Cys Arg Gly Gln His Pro Leu Glu Trp
         45                  50                  55 gct tgg cca gga gct cag gag gcg cca gcc acc gga gac aag gac agc      244
Ala Trp Pro Gly Ala Gln Glu Ala Pro Ala Thr Gly Asp Lys Asp Ser
60                  65                  70                  75 gag gac acg ggg gtg gtg cga gac tgc gag ggc aca gac gcc agg ccc      292
Glu Asp Thr Gly Val Val Arg Asp Cys Glu Gly Thr Asp Ala Arg Pro
                 80                  85                  90 tac tgc aag gtg ttg ctg ctg cac gag gta cat gcc aac gac aca ggc      340
Tyr Cys Lys Val Leu Leu Leu His Glu Val His Ala Asn Asp Thr Gly
```

-continued

```
                       95                  100                      105
agc tac gtc tgc tac tac aag tac atc aag gca cgc atc gag ggc acc         388
Ser Tyr Val Cys Tyr Tyr Lys Tyr Ile Lys Ala Arg Ile Glu Gly Thr
        110                 115                 120 acg gcc gcc agc tcc tac gtg ttc gtg aga gac ttt gag cag cca ttc         436
Thr Ala Ala Ser Ser Tyr Val Phe Val Arg Asp Phe Glu Gln Pro Phe
    125                 130                 135 atc aac aag cct gac acg ctc ttg gtc aac agg aag gac gcc atg tgg         484
Ile Asn Lys Pro Asp Thr Leu Leu Val Asn Arg Lys Asp Ala Met Trp
140                 145                 150                 155 gtg ccc tgt ctg gtg tcc atc ccc ggc ctc aat gtc acg ctg cgc tcg         532
Val Pro Cys Leu Val Ser Ile Pro Gly Leu Asn Val Thr Leu Arg Ser
                160                 165                 170 caa agc tcg gtg ctg tgg cca gac ggg cag gag gtg gtg tgg gat gac         580
Gln Ser Ser Val Leu Trp Pro Asp Gly Gln Glu Val Val Trp Asp Asp
            175                 180                 185 cgg cgg ggc atg ctc gtg tcc acg cca ctg ctg cac gat gcc ctg tac         628
Arg Arg Gly Met Leu Val Ser Thr Pro Leu Leu His Asp Ala Leu Tyr
        190                 195                 200 ctg cag tgc gag acc acc tgg gga gac cag gac ttc ctt tcc aac ccc         676
Leu Gln Cys Glu Thr Thr Trp Gly Asp Gln Asp Phe Leu Ser Asn Pro
    205                 210                 215 ttc ctg gtg cac atc aca ggc aac gag ctc tat gac atc cag ctg ttg         724
Phe Leu Val His Ile Thr Gly Asn Glu Leu Tyr Asp Ile Gln Leu Leu
220                 225                 230                 235 ccc agg aag tcg ctg gag ctg ctg gta ggg gag aag ctg gtc ctg aac         772
Pro Arg Lys Ser Leu Glu Leu Leu Val Gly Glu Lys Leu Val Leu Asn
                240                 245                 250 tgc acc gtg tgg gct gag ttt aac tca ggt gtc acc ttt gac tgg gac         820
Cys Thr Val Trp Ala Glu Phe Asn Ser Gly Val Thr Phe Asp Trp Asp
            255                 260                 265 tac cca ggg aag cag gca gag cgg ggt aag tgg gtg ccc gag cga cgc         868
Tyr Pro Gly Lys Gln Ala Glu Arg Gly Lys Trp Val Pro Glu Arg Arg
        270                 275                 280 tcc cag cag acc cac aca gaa ctc tcc agc atc ctg acc atc cac aac         916
Ser Gln Gln Thr His Thr Glu Leu Ser Ser Ile Leu Thr Ile His Asn
    285                 290                 295 gtc agc cag cac gac ctg ggc tcg tat gtg tgc aag gcc aac aac ggc         964
Val Ser Gln His Asp Leu Gly Ser Tyr Val Cys Lys Ala Asn Asn Gly
300                 305                 310                 315 atc cag cga ttt cgg gag agc acc gag gtc att gtg cat gaa aat ccc        1012
Ile Gln Arg Phe Arg Glu Ser Thr Glu Val Ile Val His Glu Asn Pro
                320                 325                 330 ttc atc agc gtc gag tgg ctc aaa gga ccc atc ctg gag gcc acg gca        1060
Phe Ile Ser Val Glu Trp Leu Lys Gly Pro Ile Leu Glu Ala Thr Ala
            335                 340                 345 gga gac gag ctg gtg aag ctg ccc gtg aag ctg gca gcg tac ccc ccg        1108
Gly Asp Glu Leu Val Lys Leu Pro Val Lys Leu Ala Ala Tyr Pro Pro
        350                 355                 360 ccc gag ttc cag tgg tac aag gat gga aag gca ctg tcc ggg cgc cac        1156
Pro Glu Phe Gln Trp Tyr Lys Asp Gly Lys Ala Leu Ser Gly Arg His
    365                 370                 375 agt cca cat gcc ctg gtg ctc aag gag gtg aca gag gcc agc aca ggc        1204
Ser Pro His Ala Leu Val Leu Lys Glu Val Thr Glu Ala Ser Thr Gly
380                 385                 390                 395 acc tac acc ctc gcc ctg tgg aac tcc gct gct ggc ctg agg cgc aac        1252
Thr Tyr Thr Leu Ala Leu Trp Asn Ser Ala Ala Gly Leu Arg Arg Asn
                400                 405                 410 atc agc ctg gag ctg gtg gtg aat gtg ccc ccc cag ata cat gag aag        1300
Ile Ser Leu Glu Leu Val Val Asn Val Pro Pro Gln Ile His Glu Lys
```

```
                Ile Ser Leu Glu Leu Val Val Asn Val Pro Pro Gln Ile His Glu Lys
                            415                 420                 425 gag gcc tcc tcc ccc agc atc tac tcg cgt cac agc cgc cag gcc ctc          1348
Glu Ala Ser Ser Pro Ser Ile Tyr Ser Arg His Ser Arg Gln Ala Leu
                430                 435                 440 acc tgc acg gcc tac ggg gtg ccc ctg cct ctc agc atc cag tgg cac          1396
Thr Cys Thr Ala Tyr Gly Val Pro Leu Pro Leu Ser Ile Gln Trp His
        445                 450                 455 tgg cgg ccc tgg aca ccc tgc aag atg ttt gcc cag cgt agt ctc cgg          1444
Trp Arg Pro Trp Thr Pro Cys Lys Met Phe Ala Gln Arg Ser Leu Arg
460                 465                 470                 475 cgg cgg cag cag caa gac ctc atg cca cag tgc cgt gac tgg agg gcg          1492
Arg Arg Gln Gln Gln Asp Leu Met Pro Gln Cys Arg Asp Trp Arg Ala
                480                 485                 490 gtg acc acg cag gat gcc gtg aac ccc atc gag agc ctg gac acc tgg          1540
Val Thr Thr Gln Asp Ala Val Asn Pro Ile Glu Ser Leu Asp Thr Trp
                495                 500                 505 acc gag ttt gtg gag gga aag aat aag act gtg agc aag ctg gtg atc          1588
Thr Glu Phe Val Glu Gly Lys Asn Lys Thr Val Ser Lys Leu Val Ile
            510                 515                 520 cag aat gcc aac gtg tct gcc atg tac aag tgt gtg gtc tcc aac aag          1636
Gln Asn Ala Asn Val Ser Ala Met Tyr Lys Cys Val Val Ser Asn Lys
525                 530                 535 gtg ggc cag gat gag cgg ctc atc tac ttc tat gtg acc acc atc ccc          1684
Val Gly Gln Asp Glu Arg Leu Ile Tyr Phe Tyr Val Thr Thr Ile Pro
540                 545                 550                 555 gac ggc ttc acc atc gaa tcc aag cca tcc gag gag cta cta gag ggc          1732
Asp Gly Phe Thr Ile Glu Ser Lys Pro Ser Glu Glu Leu Leu Glu Gly
                560                 565                 570 cag ccg gtg ctc ctg agc tgc caa gcc gac agc tac aag tac gag cat          1780
Gln Pro Val Leu Leu Ser Cys Gln Ala Asp Ser Tyr Lys Tyr Glu His
            575                 580                 585 ctg cgc tgg tac cgc ctc aac ctg tcc acg ctg cac gat gcg cac ggg          1828
Leu Arg Trp Tyr Arg Leu Asn Leu Ser Thr Leu His Asp Ala His Gly
        590                 595                 600 aac ccg ctt ctg ctc gac tgc aag aac gtg cat ctg ttc gcc acc cct          1876
Asn Pro Leu Leu Leu Asp Cys Lys Asn Val His Leu Phe Ala Thr Pro
605                 610                 615 ctg gcc gcc agc ctg gag gag gtg gca cct ggg gcg cgc cac gcc acg          1924
Leu Ala Ala Ser Leu Glu Glu Val Ala Pro Gly Ala Arg His Ala Thr
620                 625                 630                 635 ctc agc ctg agt atc ccc cgc gtc gcg ccc gag cac gag ggc cac tat          1972
Leu Ser Leu Ser Ile Pro Arg Val Ala Pro Glu His Glu Gly His Tyr
                640                 645                 650 gtg tgc gaa gtg caa gac cgg cgc agc cat gac aag cac tgc cac aag          2020
Val Cys Glu Val Gln Asp Arg Arg Ser His Asp Lys His Cys His Lys
            655                 660                 665 aag tac ctg tcg gtg cag gcc ctg gaa gcc cct cgg ctc acg cag aac          2068
Lys Tyr Leu Ser Val Gln Ala Leu Glu Ala Pro Arg Leu Thr Gln Asn
        670                 675                 680 ttg acc gac ctc ctg gtg aac gtg agc gac tcg ctg gag atg cag tgc          2116
Leu Thr Asp Leu Leu Val Asn Val Ser Asp Ser Leu Glu Met Gln Cys
685                 690                 695 ttg gtg gcc gga gcg cac gcg ccc agc atc gtg tgg tac aaa gac gag          2164
Leu Val Ala Gly Ala His Ala Pro Ser Ile Val Trp Tyr Lys Asp Glu
700                 705                 710                 715 agg ctg ctg gag gaa aag tct gga gtc gac ttg gcg gac tcc aac cag          2212
Arg Leu Leu Glu Glu Lys Ser Gly Val Asp Leu Ala Asp Ser Asn Gln
                720                 725                 730
```

| | | |
|---|---|---|
| aag ctg agc atc cag cgc gtg cgc gag gag gat gcg gga cgc tat ctg<br>Lys Leu Ser Ile Gln Arg Val Arg Glu Glu Asp Ala Gly Arg Tyr Leu<br>735　　　　　　　　740　　　　　　　　745 | | 2260 |
| tgc agc gtg tgc aac gcc aag ggc tgc gtc aac tcc tcc gcc agc gtg<br>Cys Ser Val Cys Asn Ala Lys Gly Cys Val Asn Ser Ser Ala Ser Val<br>　　750　　　　　　　　755　　　　　　　　760 | | 2308 |
| gcc gtg gaa ggc tcc gag gat aag ggc agc atg gag atc gtg atc ctt<br>Ala Val Glu Gly Ser Glu Asp Lys Gly Ser Met Glu Ile Val Ile Leu<br>765　　　　　　　　770　　　　　　　　775 | | 2356 |
| gtc ggt acc ggc gtc atc gct gtc ttc ttc tgg gtc ctc ctc ctc ctc<br>Val Gly Thr Gly Val Ile Ala Val Phe Phe Trp Val Leu Leu Leu Leu<br>780　　　　　　　　785　　　　　　　　　　　795 | | 2404 |
| atc ttc tgt aac atg agg agg ccg gcc cac gca gac atc aag acg ggc<br>Ile Phe Cys Asn Met Arg Arg Pro Ala His Ala Asp Ile Lys Thr Gly<br>　　　　800　　　　　　　　805　　　　　　　　810 | | 2452 |
| tac ctg tcc atc atc atg gac ccc ggg gag gtg cct ctg gag gag caa<br>Tyr Leu Ser Ile Ile Met Asp Pro Gly Glu Val Pro Leu Glu Glu Gln<br>　　　　　815　　　　　　　　820　　　　　　　　825 | | 2500 |
| tgc gaa tac ctg tcc tac gat gcc agc cag tgg gaa ttc ccc cga gag<br>Cys Glu Tyr Leu Ser Tyr Asp Ala Ser Gln Trp Glu Phe Pro Arg Glu<br>　　　　　　830　　　　　　　　835　　　　　　　　840 | | 2548 |
| cgg ctg cac ctg ggg aga gtg ctc ggc tac ggc gcc ttc ggg aag gtg<br>Arg Leu His Leu Gly Arg Val Leu Gly Tyr Gly Ala Phe Gly Lys Val<br>845　　　　　　　　850　　　　　　　　855 | | 2596 |
| gtg gaa gcc tcc gct ttc ggc atc cac aag ggc agc agc tgt gac acc<br>Val Glu Ala Ser Ala Phe Gly Ile His Lys Gly Ser Ser Cys Asp Thr<br>860　　　　　　　　865　　　　　　　　870　　　　　　　　875 | | 2644 |
| gtg gcc gtg aaa atg ctg aaa gag ggc gcc acg gcc agc gag cac cgc<br>Val Ala Val Lys Met Leu Lys Glu Gly Ala Thr Ala Ser Glu His Arg<br>　　　　　　　　880　　　　　　　　885　　　　　　　　890 | | 2692 |
| gcg ctg atg tcg gag ctc aag atc ctc att cac atc ggc aac cac ctc<br>Ala Leu Met Ser Glu Leu Lys Ile Leu Ile His Ile Gly Asn His Leu<br>　　　　　　　　895　　　　　　　　900　　　　　　　　905 | | 2740 |
| aac gtg gtc aac ctc ctc ggg gcg tgc acc aag ccg cag ggc ccc ctc<br>Asn Val Val Asn Leu Leu Gly Ala Cys Thr Lys Pro Gln Gly Pro Leu<br>　　　　　　　　910　　　　　　　　915　　　　　　　　920 | | 2788 |
| atg gtg atc gtg gag ttc tgc aag tac ggc aac ctc tcc aac ttc ctg<br>Met Val Ile Val Glu Phe Cys Lys Tyr Gly Asn Leu Ser Asn Phe Leu<br>925　　　　　　　　930　　　　　　　　935 | | 2836 |
| cgc gcc aag cgg gac gcc ttc agc ccc tgc gcg gag aag tct ccc gag<br>Arg Ala Lys Arg Asp Ala Phe Ser Pro Cys Ala Glu Lys Ser Pro Glu<br>940　　　　　　　　945　　　　　　　　950　　　　　　　　955 | | 2884 |
| cag cgc gga cgc ttc cgc gcc atg gtg gag ctc gcc agg ctg gat cgg<br>Gln Arg Gly Arg Phe Arg Ala Met Val Glu Leu Ala Arg Leu Asp Arg<br>　　　　　　　　960　　　　　　　　965　　　　　　　　970 | | 2932 |
| agg cgg ccg ggg agc agc gac agg gtc ctc ttc gcg cgg ttc tcg aag<br>Arg Arg Pro Gly Ser Ser Asp Arg Val Leu Phe Ala Arg Phe Ser Lys<br>　　　　　　　　975　　　　　　　　980　　　　　　　　985 | | 2980 |
| acc gag ggc gga gcg agg cgg gct tct cca gac caa gaa　gct gag gac<br>Thr Glu Gly Gly Ala Arg Arg Ala Ser Pro Asp Gln Glu　Ala Glu Asp<br>　　　　　　　　990　　　　　　　　995　　　　　　　　　1000 | | 3028 |
| ctg tgg ctg agc ccg ctg acc　atg gaa gat ctt gtc　tgc tac agc<br>Leu Trp Leu Ser Pro Leu Thr Met Glu Asp Leu Val　Cys Tyr Ser<br>　1005　　　　　　　　1010　　　　　　　　　1015 | | 3073 |
| ttc cag gtg gcc aga ggg atg　gag ttc ctg gct tcc　cga aag tgc<br>Phe Gln Val Ala Arg Gly Met Glu Phe Leu Ala Ser　Arg Lys Cys<br>　1020　　　　　　　　1025　　　　　　　　　1030 | | 3118 |
| atc cac aga gac ctg gct gct　cgg aac att ctg ctg　tcg gaa agc<br>Ile His Arg Asp Leu Ala Ala Arg Asn Ile Leu Leu　Ser Glu Ser<br>　1035　　　　　　　　1040　　　　　　　　　1045 | | 3163 |

-continued

| | |
|---|---|
| gac gtg gtg aag atc tgt gac ttt ggc ctt gcc cgg gac atc tac<br>Asp Val Val Lys Ile Cys Asp Phe Gly Leu Ala Arg Asp Ile Tyr<br>1050                     1055                     1060 | 3208 |
| aaa gac cct gac tac gtc cgc aag ggc agt gcc cgg ctg ccc ctg<br>Lys Asp Pro Asp Tyr Val Arg Lys Gly Ser Ala Arg Leu Pro Leu<br>1065                     1070                     1075 | 3253 |
| aag tgg atg gcc cct gaa agc atc ttc gac aag gtg tac acc acg<br>Lys Trp Met Ala Pro Glu Ser Ile Phe Asp Lys Val Tyr Thr Thr<br>1080                     1085                     1090 | 3298 |
| cag agt gac gtg tgg tcc ttt ggg gtg ctt ctc tgg gag atc ttc<br>Gln Ser Asp Val Trp Ser Phe Gly Val Leu Leu Trp Glu Ile Phe<br>1095                     1100                     1105 | 3343 |
| tct ctg ggg gcc tcc ccg tac cct ggg gtg cag atc aat gag gag<br>Ser Leu Gly Ala Ser Pro Tyr Pro Gly Val Gln Ile Asn Glu Glu<br>1110                     1115                     1120 | 3388 |
| ttc tgc cag cgg ctg aga gac ggc aca agg atg agg gcc ccg gag<br>Phe Cys Gln Arg Leu Arg Asp Gly Thr Arg Met Arg Ala Pro Glu<br>1125                     1130                     1135 | 3433 |
| ctg gcc act ccc gcc ata cgc cgc atc atg ctg aac tgc tgg tcc<br>Leu Ala Thr Pro Ala Ile Arg Arg Ile Met Leu Asn Cys Trp Ser<br>1140                     1145                     1150 | 3478 |
| gga gac ccc aag gcg aga cct gca ttc tcg gag ctg gtg gag atc<br>Gly Asp Pro Lys Ala Arg Pro Ala Phe Ser Glu Leu Val Glu Ile<br>1155                     1160                     1165 | 3523 |
| ctg ggg gac ctg ctc cag ggc agg ggc ctg caa gag gaa gag gag<br>Leu Gly Asp Leu Leu Gln Gly Arg Gly Leu Gln Glu Glu Glu Glu<br>1170                     1175                     1180 | 3568 |
| gtc tgc atg gcc ccg cgc agc tct cag agc tca gaa gag ggc agc<br>Val Cys Met Ala Pro Arg Ser Ser Gln Ser Ser Glu Glu Gly Ser<br>1185                     1190                     1195 | 3613 |
| ttc tcg cag gtg tcc acc atg gcc cta cac atc gcc cag gct gac<br>Phe Ser Gln Val Ser Thr Met Ala Leu His Ile Ala Gln Ala Asp<br>1200                     1205                     1210 | 3658 |
| gct gag gac agc ccg cca agc ctg cag cgc cac agc ctg gcc gcc<br>Ala Glu Asp Ser Pro Pro Ser Leu Gln Arg His Ser Leu Ala Ala<br>1215                     1220                     1225 | 3703 |
| agg tat tac aac tgg gtg tcc ttt ccc ggg tgc ctg gcc aga ggg<br>Arg Tyr Tyr Asn Trp Val Ser Phe Pro Gly Cys Leu Ala Arg Gly<br>1230                     1235                     1240 | 3748 |
| gct gag acc cgt ggt tcc tcc agg atg aag aca ttt gag gaa ttc<br>Ala Glu Thr Arg Gly Ser Ser Arg Met Lys Thr Phe Glu Glu Phe<br>1245                     1250                     1255 | 3793 |
| ccc atg acc cca acg acc tac aaa ggc tct gtg gac aac cag aca<br>Pro Met Thr Pro Thr Thr Tyr Lys Gly Ser Val Asp Asn Gln Thr<br>1260                     1265                     1270 | 3838 |
| gac agt ggg atg gtg ctg gcc tcg gag gag ttt gag cag ata gag<br>Asp Ser Gly Met Val Leu Ala Ser Glu Glu Phe Glu Gln Ile Glu<br>1275                     1280                     1285 | 3883 |
| agc agg cat aga caa gaa agc ggc ttc agc tgt aaa gga cct ggc<br>Ser Arg His Arg Gln Glu Ser Gly Phe Ser Cys Lys Gly Pro Gly<br>1290                     1295                     1300 | 3928 |
| cag aat gtg gct gtg acc agg gca cac cct gac tcc caa ggg agg<br>Gln Asn Val Ala Val Thr Arg Ala His Pro Asp Ser Gln Gly Arg<br>1305                     1310                     1315 | 3973 |
| cgg cgg cgg cct gag cgg ggg gcc cga gga ggc cag gtg ttt tac<br>Arg Arg Arg Pro Glu Arg Gly Ala Arg Gly Gly Gln Val Phe Tyr<br>1320                     1325                     1330 | 4018 |
| aac agc gag tat ggg gag ctg tcg gag cca agc gag gag gac cac<br>Asn Ser Glu Tyr Gly Glu Leu Ser Glu Pro Ser Glu Glu Asp His | 4063 |

-continued

```
                1335                1340                1345
tgc tcc  ccg tct gcc cgc gtg  act ttc ttc aca gac  aac agc tac         4108
Cys Ser  Pro Ser Ala Arg Val  Thr Phe Phe Thr Asp  Asn Ser Tyr
     1350                1355                1360 taa gcagcatcgg acaagacccc cagcacttgg gggttcaggc ccggcagggc              4161
gggcagaggg ctggaggccc aggctgggaa ctcatctggt tgaactctgg tggcacagga      4221
gtgtcctctt ccctctctgc agacttccca gctaggaaga gcaggactcc aggcccaagg      4281
ctcccggaat tccgtcacca cgactggcca gggcacgctc cagctgcccc ggcccctccc      4341
cctgagattc agatgtcatt tagttcagca tccgcaggtg ctggtcccgg gccagcact       4401 tccatgggaa tgtctctttg gcgacctcct ttcatcacac tgggtggtgg cctggtccct      4461
gttttcccac gaggaatctg tgggtctggg agtcacacag tgttggaggt taaggcatac      4521
gagagcagag gtctcccaaa cgccctttcc tcctcaggca cacagctact ctccccacga      4581
gggctggctg gcctcaccca cccctgcaca gttgaaggga ggggctgtgt ttccatctca      4641
aagaaggcat ttgcagggtc ctcttctggg cctgaccaaa cagccaacta gcccctgggg      4701
tggccaccag tatgacagta ttatacgctg gcaacacaga ggcagcccgc acacctgcgc      4761
ctgggtgttg agagccatcc tgcaagtctt tttc                                  4795

<210> SEQ ID NO 41
<211> LENGTH: 1363
<212> TYPE: PRT
<213> ORGANISM: Homo sapiens

<400> SEQUENCE: 41

Met Gln Arg Gly Ala Ala Leu Cys Leu Arg Leu Trp Leu Cys Leu Gly
1               5                   10                  15

Leu Leu Asp Gly Leu Val Ser Gly Tyr Ser Met Thr Pro Pro Thr Leu
            20                  25                  30

Asn Ile Thr Glu Glu Ser His Val Ile Asp Thr Gly Asp Ser Leu Ser
        35                  40                  45

Ile Ser Cys Arg Gly Gln His Pro Leu Glu Trp Ala Trp Pro Gly Ala
    50                  55                  60

Gln Glu Ala Pro Ala Thr Gly Asp Lys Asp Ser Glu Asp Thr Gly Val
65                  70                  75                  80

Val Arg Asp Cys Glu Gly Thr Asp Ala Arg Pro Tyr Cys Lys Val Leu
                85                  90                  95

Leu Leu His Glu Val His Ala Asn Asp Thr Gly Ser Tyr Val Cys Tyr
            100                 105                 110

Tyr Lys Tyr Ile Lys Ala Arg Ile Glu Gly Thr Thr Ala Ala Ser Ser
        115                 120                 125

Tyr Val Phe Val Arg Asp Phe Glu Gln Pro Phe Ile Asn Lys Pro Asp
    130                 135                 140

Thr Leu Leu Val Asn Arg Lys Asp Ala Met Trp Val Pro Cys Leu Val
145                 150                 155                 160

Ser Ile Pro Gly Leu Asn Val Thr Leu Arg Ser Gln Ser Ser Val Leu
                165                 170                 175

Trp Pro Asp Gly Gln Glu Val Val Trp Asp Asp Arg Arg Gly Met Leu
            180                 185                 190

Val Ser Thr Pro Leu Leu His Asp Ala Leu Tyr Leu Gln Cys Glu Thr
        195                 200                 205

Thr Trp Gly Asp Gln Asp Phe Leu Ser Asn Pro Phe Leu Val His Ile
    210                 215                 220
```

```
Thr Gly Asn Glu Leu Tyr Asp Ile Gln Leu Leu Pro Arg Lys Ser Leu
225                 230                 235                 240

Glu Leu Leu Val Gly Glu Lys Leu Val Leu Asn Cys Thr Val Trp Ala
            245                 250                 255

Glu Phe Asn Ser Gly Val Thr Phe Asp Trp Asp Tyr Pro Gly Lys Gln
            260                 265                 270

Ala Glu Arg Gly Lys Trp Val Pro Glu Arg Arg Ser Gln Gln Thr His
            275                 280                 285

Thr Glu Leu Ser Ser Ile Leu Thr Ile His Asn Val Ser Gln His Asp
            290                 295                 300

Leu Gly Ser Tyr Val Cys Lys Ala Asn Asn Gly Ile Gln Arg Phe Arg
305                 310                 315                 320

Glu Ser Thr Glu Val Ile Val His Glu Asn Pro Phe Ile Ser Val Glu
            325                 330                 335

Trp Leu Lys Gly Pro Ile Leu Glu Ala Thr Ala Gly Asp Glu Leu Val
            340                 345                 350

Lys Leu Pro Val Lys Leu Ala Ala Tyr Pro Pro Pro Glu Phe Gln Trp
            355                 360                 365

Tyr Lys Asp Gly Lys Ala Leu Ser Gly Arg His Ser Pro His Ala Leu
            370                 375                 380

Val Leu Lys Glu Val Thr Glu Ala Ser Thr Gly Thr Tyr Thr Leu Ala
385                 390                 395                 400

Leu Trp Asn Ser Ala Ala Gly Leu Arg Arg Asn Ile Ser Leu Glu Leu
            405                 410                 415

Val Val Asn Val Pro Pro Gln Ile His Glu Lys Glu Ala Ser Ser Pro
            420                 425                 430

Ser Ile Tyr Ser Arg His Ser Arg Gln Ala Leu Thr Cys Thr Ala Tyr
            435                 440                 445

Gly Val Pro Leu Pro Leu Ser Ile Gln Trp His Trp Arg Pro Trp Thr
            450                 455                 460

Pro Cys Lys Met Phe Ala Gln Arg Ser Leu Arg Arg Arg Gln Gln Gln
465                 470                 475                 480

Asp Leu Met Pro Gln Cys Arg Asp Trp Arg Ala Val Thr Thr Gln Asp
            485                 490                 495

Ala Val Asn Pro Ile Glu Ser Leu Asp Thr Trp Thr Glu Phe Val Glu
            500                 505                 510

Gly Lys Asn Lys Thr Val Ser Lys Leu Val Ile Gln Asn Ala Asn Val
            515                 520                 525

Ser Ala Met Tyr Lys Cys Val Val Ser Asn Lys Val Gly Gln Asp Glu
            530                 535                 540

Arg Leu Ile Tyr Phe Tyr Val Thr Thr Ile Pro Asp Gly Phe Thr Ile
545                 550                 555                 560

Glu Ser Lys Pro Ser Glu Glu Leu Leu Glu Gly Gln Pro Val Leu Leu
            565                 570                 575

Ser Cys Gln Ala Asp Ser Tyr Lys Tyr Glu His Leu Arg Trp Tyr Arg
            580                 585                 590

Leu Asn Leu Ser Thr Leu His Asp Ala His Gly Asn Pro Leu Leu Leu
            595                 600                 605

Asp Cys Lys Asn Val His Leu Phe Ala Thr Pro Leu Ala Ala Ser Leu
            610                 615                 620

Glu Glu Val Ala Pro Gly Ala Arg His Ala Thr Leu Ser Leu Ser Ile
625                 630                 635                 640
```

```
Pro Arg Val Ala Pro Glu His Glu Gly His Tyr Val Cys Glu Val Gln
            645                 650                 655

Asp Arg Arg Ser His Asp Lys His Cys His Lys Lys Tyr Leu Ser Val
            660                 665                 670

Gln Ala Leu Glu Ala Pro Arg Leu Thr Gln Asn Leu Thr Asp Leu Leu
            675                 680                 685

Val Asn Val Ser Asp Ser Leu Glu Met Gln Cys Leu Ala Gly Ala
            690                 695                 700

His Ala Pro Ser Ile Val Trp Tyr Lys Asp Glu Arg Leu Leu Glu Glu
705                 710                 715                 720

Lys Ser Gly Val Asp Leu Ala Asp Ser Asn Gln Lys Leu Ser Ile Gln
            725                 730                 735

Arg Val Arg Glu Glu Asp Ala Gly Arg Tyr Leu Cys Ser Val Cys Asn
            740                 745                 750

Ala Lys Gly Cys Val Asn Ser Ser Ala Ser Val Ala Val Glu Gly Ser
            755                 760                 765

Glu Asp Lys Gly Ser Met Glu Ile Val Ile Leu Val Gly Thr Gly Val
            770                 775                 780

Ile Ala Val Phe Phe Trp Val Leu Leu Leu Leu Ile Phe Cys Asn Met
785                 790                 795                 800

Arg Arg Pro Ala His Ala Asp Ile Lys Thr Gly Tyr Leu Ser Ile Ile
            805                 810                 815

Met Asp Pro Gly Glu Val Pro Leu Glu Glu Gln Cys Glu Tyr Leu Ser
            820                 825                 830

Tyr Asp Ala Ser Gln Trp Glu Phe Pro Arg Glu Arg Leu His Leu Gly
            835                 840                 845

Arg Val Leu Gly Tyr Gly Ala Phe Gly Lys Val Val Glu Ala Ser Ala
            850                 855                 860

Phe Gly Ile His Lys Gly Ser Ser Cys Asp Thr Val Ala Val Lys Met
865                 870                 875                 880

Leu Lys Glu Gly Ala Thr Ala Ser Glu His Arg Ala Leu Met Ser Glu
            885                 890                 895

Leu Lys Ile Leu Ile His Ile Gly Asn His Leu Asn Val Val Asn Leu
            900                 905                 910

Leu Gly Ala Cys Thr Lys Pro Gln Gly Pro Leu Met Val Ile Val Glu
            915                 920                 925

Phe Cys Lys Tyr Gly Asn Leu Ser Asn Phe Leu Arg Ala Lys Arg Asp
            930                 935                 940

Ala Phe Ser Pro Cys Ala Glu Lys Ser Pro Glu Gln Arg Gly Arg Phe
945                 950                 955                 960

Arg Ala Met Val Glu Leu Ala Arg Leu Asp Arg Arg Pro Gly Ser
            965                 970                 975

Ser Asp Arg Val Leu Phe Ala Arg Phe Ser Lys Thr Glu Gly Gly Ala
            980                 985                 990

Arg Arg Ala Ser Pro Asp Gln Glu Ala Glu Asp Leu Trp Leu Ser Pro
            995                 1000                1005

Leu Thr Met Glu Asp Leu Val Cys Tyr Ser Phe Gln Val Ala Arg
            1010                1015                1020

Gly Met Glu Phe Leu Ala Ser Arg Lys Cys Ile His Arg Asp Leu
            1025                1030                1035

Ala Ala Arg Asn Ile Leu Leu Ser Glu Ser Asp Val Val Lys Ile
            1040                1045                1050

Cys Asp Phe Gly Leu Ala Arg Asp Ile Tyr Lys Asp Pro Asp Tyr
```

```
            1055                1060                1065

Val  Arg  Lys  Gly  Ser  Ala  Arg  Leu  Pro  Leu  Lys  Trp  Met  Ala  Pro
            1070                1075                1080

Glu  Ser  Ile  Phe  Asp  Lys  Val  Tyr  Thr  Thr  Gln  Ser  Asp  Val  Trp
            1085                1090                1095

Ser  Phe  Gly  Val  Leu  Leu  Trp  Glu  Ile  Phe  Ser  Leu  Gly  Ala  Ser
            1100                1105                1110

Pro  Tyr  Pro  Gly  Val  Gln  Ile  Asn  Glu  Glu  Phe  Cys  Gln  Arg  Leu
            1115                1120                1125

Arg  Asp  Gly  Thr  Arg  Met  Arg  Ala  Pro  Glu  Leu  Ala  Thr  Pro  Ala
            1130                1135                1140

Ile  Arg  Arg  Ile  Met  Leu  Asn  Cys  Trp  Ser  Gly  Asp  Pro  Lys  Ala
            1145                1150                1155

Arg  Pro  Ala  Phe  Ser  Glu  Leu  Val  Glu  Ile  Leu  Gly  Asp  Leu  Leu
            1160                1165                1170

Gln  Gly  Arg  Gly  Leu  Gln  Glu  Glu  Glu  Val  Cys  Met  Ala  Pro
            1175                1180                1185

Arg  Ser  Ser  Gln  Ser  Ser  Glu  Glu  Gly  Ser  Phe  Ser  Gln  Val  Ser
            1190                1195                1200

Thr  Met  Ala  Leu  His  Ile  Ala  Gln  Ala  Asp  Ala  Glu  Asp  Ser  Pro
            1205                1210                1215

Pro  Ser  Leu  Gln  Arg  His  Ser  Leu  Ala  Ala  Arg  Tyr  Tyr  Asn  Trp
            1220                1225                1230

Val  Ser  Phe  Pro  Gly  Cys  Leu  Ala  Arg  Gly  Ala  Glu  Thr  Arg  Gly
            1235                1240                1245

Ser  Ser  Arg  Met  Lys  Thr  Phe  Glu  Glu  Phe  Pro  Met  Thr  Pro  Thr
            1250                1255                1260

Thr  Tyr  Lys  Gly  Ser  Val  Asp  Asn  Gln  Thr  Asp  Ser  Gly  Met  Val
            1265                1270                1275

Leu  Ala  Ser  Glu  Glu  Phe  Glu  Gln  Ile  Glu  Ser  Arg  His  Arg  Gln
            1280                1285                1290

Glu  Ser  Gly  Phe  Ser  Cys  Lys  Gly  Pro  Gly  Gln  Asn  Val  Ala  Val
            1295                1300                1305

Thr  Arg  Ala  His  Pro  Asp  Ser  Gln  Gly  Arg  Arg  Arg  Arg  Pro  Glu
            1310                1315                1320

Arg  Gly  Ala  Arg  Gly  Gly  Gln  Val  Phe  Tyr  Asn  Ser  Glu  Tyr  Gly
            1325                1330                1335

Glu  Leu  Ser  Glu  Pro  Ser  Glu  Asp  His  Cys  Ser  Pro  Ser  Ala
            1340                1345                1350

Arg  Val  Thr  Phe  Phe  Thr  Asp  Asn  Ser  Tyr
            1355                1360

<210> SEQ ID NO 42
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (1)..(10)
<223> OTHER INFORMATION: Cyclic peptide

<400> SEQUENCE: 42

Cys  Gly  Tyr  Trp  Leu  Thr  Ile  Trp  Gly  Cys
1                 5                  10
```

```
<210> SEQ ID NO 43
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (1)..(13)

<400> SEQUENCE: 43

Cys Ala Ser Glu Leu Gly Lys Ser Thr Asn Thr Phe Cys
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (1)..(8)

<400> SEQUENCE: 44

Cys Asn Glu Glu Ser Leu Ile Cys
1               5

<210> SEQ ID NO 45
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: DISULFID
<222> LOCATION: (1)..(11)

<400> SEQUENCE: 45

Cys Ile Ser Val Pro Leu Thr Ser Val Pro Cys
1               5                   10

<210> SEQ ID NO 46
<211> LENGTH: 132
<212> TYPE: PRT
<213> ORGANISM: Artificial Sequence
<220> FEATURE:
<223> OTHER INFORMATION: Synthetic peptide

<400> SEQUENCE: 46

Met Lys Leu Pro Val Arg Leu Leu Val Leu Met Phe Trp Ile Pro Ala
1               5                   10                  15

Ser Ser Ser Asp Phe Val Met Thr Gln Thr Pro Leu Ser Leu Pro Val
                20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110
```

Ser Gln Ser Thr His Val Pro Arg Thr Phe Gly Gly Thr Lys Leu
            115                 120                 125
Glu Ile Lys Arg
    130

<210> SEQ ID NO 47
<211> LENGTH: 137
<212> TYPE: PRT
<213> ORGANISM: Artificial Sequence
<220> FEATURE:
<223> OTHER INFORMATION: Synthetic peptide

<400> SEQUENCE: 47

Met Gly Trp Ser Gly Val Phe Leu Phe Leu Leu Ser Gly Ser Thr Gly
1               5                   10                  15
Val His Ser Glu Ile Gln Leu Gln Gln Ser Gly Pro Asp Leu Val Lys
            20                  25                  30
Pro Gly Ala Ser Val Lys Val Ser Cys Arg Ala Ser Gly Tyr Ser Phe
        35                  40                  45
Thr Gly Tyr Asn Met Tyr Trp Val Lys Gln Ser His Gly Lys Ser Leu
    50                  55                  60
Glu Trp Ile Gly Tyr Ile Asp Pro Tyr Asn Gly Asp Thr Thr Tyr Asn
65                  70                  75                  80
Gln Lys Phe Lys Gly Lys Ala Thr Leu Thr Val Asp Lys Ser Ser Ser
                85                  90                  95
Thr Ala Phe Met His Leu Asn Ser Leu Thr Ser Glu Asp Ser Ala Val
            100                 105                 110
Tyr Tyr Cys Ala Arg Thr Ser Tyr Gly Gly Met Asp Tyr Trp Gly
        115                 120                 125
Gln Gly Thr Ser Val Thr Val Ser Ser
    130                 135

<210> SEQ ID NO 48
<211> LENGTH: 16
<212> TYPE: PRT
<213> ORGANISM: Artificial Sequence
<220> FEATURE:
<223> OTHER INFORMATION: Synthetic peptide

<400> SEQUENCE: 48

Arg Ser Ser Gln Ser Leu Val His Ser Asn Gly Asn Thr Tyr Leu His
1               5                   10                  15

<210> SEQ ID NO 49
<211> LENGTH: 7
<212> TYPE: PRT
<213> ORGANISM: Artificial Sequence
<220> FEATURE:
<223> OTHER INFORMATION: Synthetic peptide

<400> SEQUENCE: 49

Lys Val Ser Asn Arg Phe Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic peptide

<400> SEQUENCE: 50

```
Ser Gln Ser Thr His Val Pro Arg Thr
1               5

<210> SEQ ID NO 51
<211> LENGTH: 10
<212> TYPE: PRT
<213> ORGANISM: Artificial Sequence
<220> FEATURE:
<223> OTHER INFORMATION: Synthetic peptide

<400> SEQUENCE: 51

Gly Tyr Ser Phe Thr Gly Tyr Asn Met Tyr
1               5                   10

<210> SEQ ID NO 52
<211> LENGTH: 17
<212> TYPE: PRT
<213> ORGANISM: Artificial Sequence
<220> FEATURE:
<223> OTHER INFORMATION: Synthetic peptide

<400> SEQUENCE: 52

Tyr Ile Asp Pro Tyr Asn Gly Asp Thr Thr Tyr Asn Gln Lys Phe Lys
1               5                   10                  15

Gly

<210> SEQ ID NO 53
<211> LENGTH: 9
<212> TYPE: PRT
<213> ORGANISM: Artificial Sequence
<220> FEATURE:
<223> OTHER INFORMATION: Synthetic peptide

<400> SEQUENCE: 53

Thr Ser Tyr Tyr Gly Gly Met Asp Tyr
1               5
```

THERAPEUTIC COMPOSITIONS FOR THE TREATMENT OF DRY EYE DISEASE

CROSS-REFERENCE TO RELATED APPLICATIONS

This application claims the benefit of priority U.S. Provisional Application Nos. 61/308,091, 61/329,845 and 61/331,278, which were filed on Feb. 25, 2010, Apr. 30, 2010 and May 4, 2010, respectively. The disclosure of each of the priority applications is incorporated herein by reference in their entireties.

FEDERALLY SPONSORED RESEARCH OR DEVELOPMENT

This invention was made with Government support under Grant No EY-12963 awarded by the National Institute of Health. The Government has certain rights in the invention.

FIELD OF THE INVENTION

This invention relates generally to the field of ophthalmology.

BACKGROUND OF THE INVENTION

Dry Eye Disease (DED) is a relatively common condition characterized by inadequate tear film protection of the cornea. Dry eye symptoms have traditionally been managed with eyelid hygiene, topical antibiotics (erythromycin or bacitracin ointments), oral tetracyclines (tetracycline, doxycycline, or minocycline), anti-inflammatory compounds (cyclosporine) and corticosteroids which are often time consuming, frustrating, and frequently ineffective or variably effective treatments.

Tens of millions of people (mostly women) are affected worldwide by dry eye. 10 million people in US are affected with severe dry eyes with more than 3.2 million women and 1.6 million men above the age of 50 years being affected by dry eye in the US. DED is a potentially disabling disease adversely impacting the vision-related quality of life. It leads to ocular discomfort, a degradation in visual performance (reading speed, contrast sensitivity) and a loss of productivity. Current therapeutic options are limited and costly. Topical cyclosporine-A (Restasis®) is the only approved treatment for DED in US. Despite the high incidence of DED, there is currently no consistently effective treatment for this condition and it still remains a therapeutic challenge. As such, there is a need for new therapeutic modalities to treat DED.

SUMMARY OF THE INVENTION

The present invention discloses a novel method for the treatment of dry eye disease in humans comprising local application of an anti-lymphangiogenic agent onto the ocular surface. The present invention is based on novel evidence for the selective growth of lymphatic vessels in DED cornea. Additionally, significant increase in both caliber and extent of lymphatics in DED corneas is accompanied by over expression of lymphangiogenic receptor VEGFR-3, further correlating DED with lymphangiogenesis.

An anti-lymphangiogenic agent of the invention is selected from the group consisting of: a nucleic acid molecule, an aptamer, an antisense molecule, an RNAi molecule, a protein, a peptide, a cyclic peptide, an antibody or antibody fragment, a polysaccharide, and a small molecule.

In one preferred embodiment of the invention, the anti-lymphangiogenic agent is an inhibitor of VEGF-C or VEGF-D mediated signal transduction by VEGFR-2 or VEGFR-3. Preferably, the amount of the anti-lymphangiogenic agent employed is effective to inhibit the binding of VEGF-C and/or VEGF-D ligand to VEGFR-3 or the stimulatory effect of VEGF-C and/or VEGF-D on VEGFR-3.

In one aspect of the invention, the inhibitor of VEGF-C or VEGF-D mediated signal transduction by VEGFR-2 or VEGFR-3 is a molecule such as but not restricted to an antibody, a small molecule or a peptide that prevents binding of VEGF-C or VEGF-D to the receptors VEGFR-2 or VEGFR-3.

In another aspect of the invention, the inhibitor of VEGF-C or VEGF-D mediated signal transduction is a VEGFR-2 or VEGFR-3 soluble receptor. Soluble receptors of VEGFR-2 or VEGFR-3 can be administered directly. Alternatively, increase in the secretion of VEGFR-2 or VEGFR-3 is accomplished by inserting the VEGFR-2 or VEGFR-3 soluble receptors genes into the genome of corneal cells. This could be epithelial cells, keratocytes, fibroblasts, endothelial cells, or bone marrow-derived cells. Methods to introduce genes into a genome of a cell are well-known in the art. Genes are introduced in the genome of corneal cells using viral or non-viral vectors. Viral vectors include for example adenoviruses, retroviruses or lentiviruses. Non-viral vectors include, for example, liposomes such as cationic lipids, nanoparticles, lipoplexes and polyplexes (complexes of polymers with DNA).

In some embodiments, the anti-lymphangiogenic agent is a VEGF-C antibody, wherein the antibody comprises a heavy chain variable region set forth in amino acids 1-118 of SEQ ID NO: 34 or a heavy chain comprising the amino acid sequence of SEQ ID NO: 34. In some embodiments, the EGF-C antibody is selected from the group consisting of antibodies 69D09, 103, MM0006-2E65 and 193208.

In alternative embodiments, the anti-lymphangiogenic agent is antibody that competitively inhibits the binding of antibody 69D09 to VEGF-C.

In some embodiments, the anti-lymphangiogenic agent is a VEGF-D antibody selected from the group consisting of antibodies 2F8, 4A5(VD1), 4E10, 5F12, 4H4, 3C10 28AT743.288.48, MM0001-7E79, RM0007-8C35, 78902, 78939 and 90409.

In some embodiments, the anti-lymphangiogenic agent is a human or humanized antibody.

In other embodiments, the anti-lymphangiogenic agent is a soluble VEGFR-3 fragment that binds VEGF-C or VEGF-D.

In still other embodiments, the anti-lymphangiogenic agent is a VEGFR-2 inhibitor.

In one embodiment of the invention, the anti-lymphangiogenic agent is administered in combination with an anti-inflammatory agent such as, but not limited to, a composition inhibiting the activity of an inflammatory cytokine selected from the group comprising IL-1, IL-17, TNF-α and IL-6.

Exemplary functional blockers of IL-1 are described in WO/2009/025763. Exemplary functional blockers of TNF-α include, but are not limited to, recombinant and/or soluble TNF-α receptors, monoclonal antibodies, and small molecule antagonists and/or inverse agonists. One or more commercially-available TNF-α blocking agents are reformulated for topical administration in this embodiment. Exemplary commercial TNF-α blocking agents used for reformulation include, but are not limited to, etanerept/Ernbrel, infliximab/Remicade, and adalimumab/Humira.

In one embodiment of the invention, the anti-lymphangiogenic agent is administered in combination with an antibiotic.

Exemplary antibiotic compositions used for combination-therapy with antagonists of IL-mediated inflammation include but are not limited to, amikacin, gentamicin, kanamycin, neomycin, netilmicin, streptomycin, tobramycin, teicoplanin, vancomycin, azithromycin, clarithromycin, clarithromycin, dirithromycin, erythromycin, roxithromycin, troleandomycin, amoxicillin, ampicillin, azlocillin, carbenicillin, clozacillin, dicloxacillin, flucozacillin, meziocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, oflazacin, trovafloxacin, mafenide, sulfacetamide, sulfamethizole, sulfasalazine, sulfisoxazole, trimethoprim, cotrimoxazole, demeclocycline, soxycycline, minocycline, oxytetracycline, or tetracycline.

The composition of the invention is locally applied to the ocular tissue, alternatively the composition of the invention is applied to the eyelids, the ocular surface, the meibomian glands or the lacrimal glands.

The composition can be in the form of a solid, a paste, an ointment, a gel, a liquid, an aerosol, a mist, a polymer, a film, an emulsion, or a suspension.

Optionally, the composition further contains a compound selected from the group consisting of a physiological acceptable salt, poloxamer analogs with carbopol, carbopol/hydroxypropyl methyl cellulose (RP MC), carbopol-methyl cellulose, carboxymethylcellulose (CMC), hyaluronic acid, cyclodextrin, and petroleum.

Dry eye disease may be attributable to a number of factors, and treatment of subjects who have developed dry eye disease due to a variety of specific factors is contemplated. In some variations, the DED to be treated is DED caused by any condition other than an alloimmune response. Alloimmune responses may result, for example, in some corneal transplant patients. More specifically, in some variations, the DED to be treated is an autoimmune DED or a DED associated with Sjogren's syndrome. In some variations, the DED is due to excessively fast tear evaporation (evaporative dry eyes) or inadequate tear production. In some variations, the dry eye disease is attributable to one or more causes selected from: aging, contact lens usage and medication usage. In some variations, the dry eye disease is a complication of LASIK refractive surgery. In other variations, the DED arises in a subject who has not had eye surgery of any kind, e.g., treatment of subjects in whom the DED is caused by LASIK surgery, corneal transplant surgery, or other ocular surgeries.

DETAILED DESCRIPTION

Dry Eye

Figure 1:
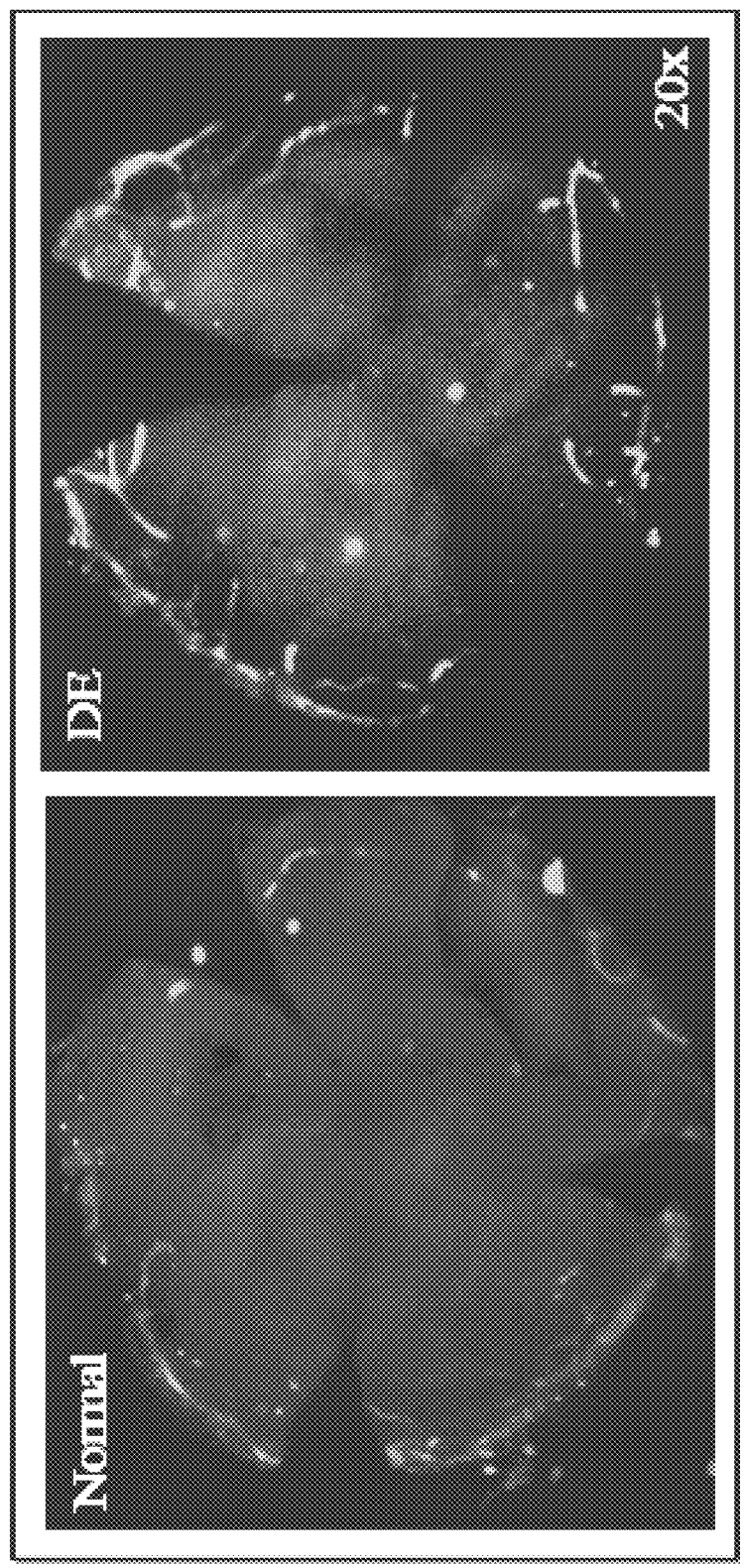
FIG. 1: Representative whole mount corneal immunofluorescence micrographs showing lymphatics (CD31$^{lo}$/LYVE-1$^{hi}$) in normal and dry eye (DE) at day 14 (20× magnification).

Keratoconjunctivitis sicca (KCS), also called keratitis sicca, sicca syndrome, xerophthalmia, dry eye syndrome (DES), or simply dry eyes, is an eye disease caused by decreased tear production or increased tear film evaporation commonly found in humans and some animals. Typical symptoms of keratoconjunctivitis are dryness, burning and a sandygritty eye irritation that gets worse as the day goes on.

Keratoconjunctivitis sicca is characterized by inadequate tear film protection of the cornea because of either inadequate tear production or abnormal tear film constitution, which results in excessively fast evaporation or premature destruction of the tear film. The tear film is constituted by 3 layers: (1) a lipid layer, produced by the Meibomian glands; (2) an aqueous layer, produced by the main and accessory lacrimal glands; and (3) a hydrophilic mucin layer, produced by the conjunctival goblet cells. Any abnormality of 1 of the 3 layers produces an unstable tear film and symptoms of keratitis sicca.

Sjogren's syndrome and autoimmune diseases associated with Sjogren's syndrome are also conditions associated with aqueous tear deficiency. Drugs such as isotretinoin, sedatives, diuretics, tricyclic antidepressants, antihypertensives, oral contraceptives, antihistamines, nasal decongestants, beta-blockers, phenothiazines, atropine, and pain relieving opiates such as morphine can cause or worsen this condition. Infiltration of the lacrimal glands by sarcoidosis or tumors, or postradiation fibrosis of the lacrimal glands can also cause this condition.

Keratoconjunctivitis sicca can also be caused by abnormal tear composition resulting in rapid evaporation or premature destruction of the tears. When caused by rapid evaporation, it is termed evaporative dry eyes. In this, although the tear gland produces a sufficient amount of tears, the rate of evaporation of the tears is too rapid. There is a loss of water from the tears that results in tears that are too "salty" or hypertonic. As a result, the entire conjunctiva and cornea cannot be kept covered with a complete layer of tears during certain activities or in certain environments.

Aging is one of the most common causes of dry eyes. About half of all people who wear contact lenses complain of dry eyes. There are two potential connections between contact lens usage and dry eye. Traditionally, it has been believed that soft contact lenses, which float on the tear film that covers the cornea, absorb the tears in the eyes. However, it is also now known that contact lens usage damages corneal nerve sensitivity, which may lead to decreased lacrimal gland tear production and dry eye. The effect of contact lenses on corneal nerve sensitivity is well established for hard contact lenses as well as soft and rigid gas permeable contact lenses. The connection between this loss in nerve sensitivity and tear production is the subject of current research. Dry eyes also occur or get worse after LASIK and other refractive surgeries. The corneal nerves stimulate tear secretion. Dry eyes caused by these procedures usually resolves after several months. Persons who are thinking about refractive surgery should consider this.

A variety of approaches can be taken to treat dry eyes. These can be summarized as: avoidance of exacerbating factors, tear stimulation and supplementation, increasing tear retention, eyelid cleansing and treatment of eye inflammation. Application of artificial tears every few hours can provide temporary relief. Inflammation occurring in response to tears film hypertonicity can be suppressed by mild topical steroids or with topical immunosuppressants such as cyclosporine. Consumption of dark-fleshed fish containing dietary omega-3 fatty acids is associated with a decreased incidence of dry eyes syndrome in women. Early experimental work on omega-3 has shown promising results when used in a topical application (Rashid S et al (2008). Arch Ophthalmol 126 (2): 219-225).

DED is increasingly recognized as an immune-mediated disorder. Desiccating stress in DED initiates an immune-based inflammation response that is sustained by the ongoing interplay between the ocular surface and various pathogenic immune cells, primarily the CD4+ cells in the conjunctivia and the CD11b+ monocytic cells in the corneal. Desiccating stress induces secretion of inflammatory cytokines, especially IL-1, TNF-α and IL-6 by ocular tissues, which facilitates the activation and migration of resident antigen presenting cells (APCs) toward the regional draining lymph nodes (LNs). In the LNs, these APCs stimulate naive T-cells, leading to the expansion of IL-17 secreting Th17 cells and interferon (IFN)-y-secreting Th1 cells. Once these effectors are generated in the LNs, they migrate to the ocular surface and secrete effector cytokines.

VEGF

VEGF (Vascular Endothelial Growth Factor) is a sub-family of growth factors, specifically the platelet-derived growth factor family of cystine-knot growth factors. They are important signaling proteins involved in both vasculogenesis (the de novo formation of the embryonic circulatory system) and angiogenesis (the growth of blood vessels from pre-existing vasculature). Members of the platelet-derived growth factor family include the Placenta growth factor (PlGF), VEGF-A (also known as VEGF), VEGF-B, VEGF-C, VEGF-D and VEGF-E.

VEGF-A, VEGF-C and VEGF-D exert their effects by variously binding to and activating structurally related membrane receptor tyrosine kinases; VEGF receptor-1 (VEGFR-1 or Flt-I), VEGFR-2 (flk-1 or KDR), and VEGFR-3 (Flt-4). Members of the VEGF family may also interact with the structurally distinct receptor neuropilin-1. Binding of a VEGF to these receptors initiates a signaling cascade, resulting in effects on gene expression and cell survival, proliferation, and migration.

VEGF-A binds to VEGFR-1 (Flt-1) and to VEGFR-2 (KDR/Flk-1). VEGFR-2 appears to mediate almost all of the known cellular responses to VEGF-A. The function of VEGFR-1 is less well-defined, although it is thought to modulate VEGFR-2 signaling. VEGF-A is believed to play a central role in the development of new blood vessels (angiogenesis) and the survival of immature blood vessels (vascular maintenance).

VEGF-C and VEGF-D are ligands for VEGFR-2 and VEGFR-3 and are involved in the mediation of lymphangiogenesis.

Lymphangiogenesis

Lymphangiogenesis refers to formation of lymphatic vessels, particularly from pre-existing lymphatic vessels, but as used herein, the term applies to formation of lymph vessels under any condition. It also applies to the enlargement of lymphatic vessels, commonly known as lymphatic hyperplasia. Lymphangiogenesis plays an important physiological role in homeostasis, metabolism and immunity. Lymphatic vessel formation has also been implicated in a number of pathological conditions including neoplasm metastasis, oedema, rheumatoid arthritis, psoriasis and impaired wound healing.

The normal human cornea is avascular, thus suppressing the afferent lymphatic and efferent vascular arms or the immune cycle. Inflammation however negates this immune and angiogenic privileged state of the cornea and giving the corneal and ocular surface the potential to mount an immune response. Our results show that corneal lymphatics play an important role in mediating the corneal inflammation in dry eyes. Inhibition of corneal lymphangiogenesis decreases ocular surface inflammation in a well characterized mouse model of DED.

Lymphangiogenesis is regulated to a large extent by VEGF-C and VEGF-D. Lymphangiogenesis appears to be regulated by signaling mediated by VEGFR-3, particularly upon specifically binding its ligands, VEGF-C and VEGF-D. VEGF-C and VEGF-D are two of six members of a family of angiogenic regulators. Other members are VEGF-A (also known as VEGF), VEGF-B, VEGF-E and placental growth factor (PIGF).

During embryogenesis, lymphatic endothelial cell sprouting, proliferation and survival is promoted by VEGF-C. Lymphatic vessels fail to develop in mice in which VEGF-C is absent (Vegfc knockout mice), and such mice develop severe edema. Indeed, absence of VEGF-C is embryonic lethal. Lymphatic vessel hypoplasia and lymphedema is exhibited in the skin of mice hemizygous for Vegfc (i.e. mice possessing one functional allele).

Lymphangiogenesis is also partly regulated by VEGF-D, similar to VEGF-C. However, lymphangiogenesis during embryonic development is not dependent upon VEGF-D, as demonstrated by Vegfd knockout mice. The lymphatic system in Vegfd knockout mice is relatively normal and Vegfd knockout mice are viable and fertile. The absolute abundance of lymphatic vessels in the lung is, however, reduced by approximately 30% compared to wild-type mice.

Lymphatic vessels express VEGFR-3, the receptor for VEGF-C and VEGF-D, and both VEGF-C and VEGF-D signal predominantly through VEGFR-3. It is also becoming apparent that lymphatic vessels variously express VEGFR-2. VEGF-C and VEGF-D are synthesized as prepro-polypeptides and are proteolytically processed by proprotein convertases. In humans, mature proteolytically processed forms of VEGF-C and VEGF-D bind to VEGFR-2 and VEGFR-3. In mice, mature VEGF-D binding is restricted to VEGFR-3.

VEGF-C and VEGF-D exist as homodimers, and it has been suggested that they may exist as VEGF-C-VEGF-D heterodimers. In addition to lymphatic vessels, VEGFR-3 is also expressed on blood vessel endothelial cells during development, thereby accounting for the severe vasculogenic and angiogenic defects observed during early embryogenesis in models comprising inactive VEGFR-3 signaling. The lymphatic system possesses almost exclusive expression of VEGFR-3 in healthy tissues in adulthood, because VEGFR-3 expression in blood vessels declines following birth and during adolescence. Thus, only lymphangiogenesis is inhibited in adults by inhibition of the VEGF-C-VEGF-D-VEGFR-3 signaling axis.

Lymphatic vessels express neuropilin-2 (NRP-2), which can bind VEGF-C or VEGF-D. In lymphangiogenesis, NRP-2 is thought to act as a co-receptor to increase the binding affinity of VEGF-C or VEGF-D to VEGFR-3. NRP-2 is required for lymphangiogenesis. Proliferation of lymphatic vessel endothelial cells was reduced and lymphatic vessels and capillaries failed to develop in Nrp2 knockout mice in which NRP-2 is absent. Similarly, NRP-1 is capable of binding VEGF-C and VEGF-D.

Defective lymphatic capillaries are the underlying cause of Milroy disease and other rare hereditary forms of lymphedema in humans. Tyrosine kinase-inactivating point mutations of the VEGFR-3 gene have been identified as a major cause of Milroy disease, and VEGF-C and VEGF-D therapy has shown promising efficacy in preclinical animal models. However, previous work has only demonstrated lymphatic capillary reconstitution, whereas effects on the collecting lymphatic vessels that are more commonly damaged in lymphedema have not been addressed.

Lymphatic vessel growth in adult tissues can be induced by Angiopoietin-1 (ANG-1) through its binding to the tunica interna endothelial cell kinase receptor 2 (TIE-2 or TEK). Lymphatic vessel sprouting that was induced by ANG-1 was inhibited by an inhibitor of VEGFR-3. Furthermore, VEGFR-3 was up-regulated by ANG-1 binding to TIE-2. TIE-2 expressed on lymphatic vascular endothelial cells may also be agonized by ANG-2 and ANG-3.

VEGF-C and VEGF-D may act as ligands for integrins. Specifically, VEGF-C and VEGF-D have been shown to act as ligands for integrin $\alpha 9\beta 1$. Cell adherence and cell migration were promoted by each of VEGF-C and VEGF-D in cells expressing integrin $\alpha 9\beta 1$. The effect could be blocked by an anti-integrin $\alpha 9\beta 1$ antibody or siRNA directed to integrin $\alpha 9\beta 1$.

Thus, in lymphangiogenesis, VEGFR-3 appears to be central. VEGFR-3 specifically binds and is activated by ligands VEGF-C and VEGF-D. VEGF-C and VEGF-D are synthesized as prepro-polypeptides and are activated by proteolytic processing by proprotein convertases. VEGF-C and VEGF-D also bind specifically to NRP-2, which is thought to be a co-receptor for VEGFR-3. Both lymphangiogenesis and VEGFR-3 are up-regulated when ANG-1 specifically binds to TIE-2. It is thought that binding of VEGF-C or VEGF-D to integrins, particularly integrin $\alpha 9\beta 1$, also performs a role in lymphangiogenesis.

Lymphangiogenesis is mediated primarily by the interaction of growth factors VEGF-C and VEGF-D on VEGFR-2 and VEGFR-3, and in particular VEGFR-3. VEGF-A also contributes, albeit indirectly, to lymphangiogenesis by recruiting VEGF-C and VEGF-D secreting macrophages. Inhibition of VEGF-C and VEGF-D signaling pathways would thus constitute a new approach to the treatment of DED. The invention is however not restricted to the inhibition of VEGF-C and VEGF-D signaling pathways and according to the present invention, other anti-lymphangiogenic agents can be used to reduce the signs and symptoms of DED.

Anti-Lymphangiogenic Agents

Persons skilled in the art will appreciate from the foregoing that inhibition of lymphangiogenesis can occur at a variety of biological points comprising any one or more of the interactions described. For example, inhibition may occur by targeting VEGF-D, VEGF-C or VEGFR-3.

An "anti-lymphangiogenic agent" is any substance that partially or fully blocks, neutralizes, reduces, inhibits or antagonizes a biological activity of a molecular component of signaling mediated by VEGFR-3 or lymphangiogenesis. Alternatively, an anti-lymphangiogenic agent is any substance that partially or fully blocks, neutralizes, reduces, inhibits or antagonizes a VEGF-C or VEGF-D biological activity. Thus, "inhibition" is the corresponding state elicited by an inhibitor. A molecular component of signaling mediated by VEGFR-3 or lymphangiogenesis includes VEGFR-3, VEGFR-2, VEGF-C, VEGF-D, proprotein convertases, neuropilin-1 (NRP-1), neuropilin-2 (NRP-2), angiopoietin-1 (ANG-1), tunica interna endothelial cell kinase receptor (TIE-2) or integrin $\alpha 9\beta 1$.

It is envisaged that practice of the invention extends to any inhibitor known now or in the future.

Suitable classes of inhibitor molecules that target VEGF-C or VEGF-D or signaling mediated by VEGFR-3, or lymphangiogenesis include antibodies, polypeptides, peptides, peptide mimetics, nucleic acid molecules, and small molecules. Such classes of inhibitor molecules are suitable also for inhibiting binding of ligands, for example VEGF-C or VEGF-D, to integrins, particularly integrin α9β1.

Suitable VEGF-C, VEGF-D, VEGFR-3-mediated signaling or lymphangiogenesis antibody inhibitors include antagonist and neutralizing antibodies or antibody fragments.

Polypeptide, peptide, or peptide mimetic VEGF-C or VEGF-D inhibitors, VEGFR-3-mediated signaling inhibitors or lymphangiogenesis inhibitors include fragments or amino acid sequence variants of native polypeptide or peptide components of VEGF-C, VEGF-D, VEGFR-3-mediated signaling or lymphangiogenesis.

Nucleic acid molecule inhibitors of VEGF-C or VEGF-D activity, VEGFR-3-mediated signaling or lymphangiogenesis include antisense molecules, nucleic acids in triple-helix formation, small interfering RNA (siRNA), and ribozymes.

Small molecule inhibitors of VEGF-C or VEGF-D, VEGFR-3-mediated signaling or lymphangiogenesis include organic and inorganic molecules.

Inhibitors of VEGF-C or VEGF-D activity, VEGFR-3-mediated signaling or lymphangiogenesis according to the present invention may exert their effects by interacting with any one or more of VEGFR-3, VEGFR-2, VEGF-C, VEGF-D, proprotein convertases, NRP-1, NRP-2, ANG-1, TIE-2 or integrins, particularly integrin α9β1, in their DNA, RNA or polypeptide forms.

Inhibition of VEGF-C or VEGF-D activity, VEGFR-3-mediated signaling or lymphangiogenesis according to the present invention may occur via inhibition of ligand availability for receptor binding, inhibition of receptor availability for ligand binding, inhibition of receptor tyrosine kinase activity, or inhibition of co-receptor interaction.

As used herein, "availability" refers to the potential or actual amount of a molecule that performs some function in VEGF-C or VEGF-D activity, VEGFR-3-mediated signaling or lymphangiogenesis and is present in a biological system. Availability may be relative or absolute. For example, if all copies of a gene encoding a polypeptide involved in lymphangiogenesis were rendered non-functional by genetic mutation and no functioning polypeptide was synthesized, then there would be no availability of the polypeptide in an absolute sense. Alternatively, if the same gene was present with one functioning copy and 50% of the polypeptide was synthesized, there would be reduced or inhibited availability in a relative sense. Similarly, other mechanisms may be envisaged where availability is affected. Receptors may be transcribed or translated to a lesser degree when compared with a control, or the receptor may be targeted by an antibody that binds specifically to the ligand binding site, thereby reducing or inhibiting receptor availability for ligand binding. Analogously, if ligand synthesis is targeted by an antisense inhibitor, or if an antibody inhibitor or soluble receptor inhibitor specifically binds to the ligand, then there will be reduction or inhibition of ligand availability for receptor binding.

The term "specific binding" or "specifically binds" or "specific for" refers to binding where a molecule binds to a particular polypeptide or epitope on a particular polypeptide without substantially binding to any other polypeptide or polypeptide epitope. Such binding is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. As used herein, specific binding is used in relation to the interaction between the molecular components of VEGF-C or VEGF-D activity, VEGFR-3-mediated signaling or lymphangiogenesis. Specific binding is also used in relation to the interaction between the molecular components of VEGF-C or VEGF-D activity, VEGFR-3-mediated signaling or lymphangiogenesis and agents that partially or fully block, neutralize, reduce or antagonize a biological activity of a molecule that facilitates VEGFR-3-mediated signaling or lymphangiogenesis. Specific binding also applies to the interaction between the molecular components of VEGF-C or VEGF-D activity and agents that partially or fully block, neutralize, reduce or antagonize VEGF-C or VEGF-D biological activity.

In particular, specific binding refers to a molecule having a $K_d$ at least 2-fold less for the particular polypeptide or epitope on a particular polypeptide than it does for a non-specific target. Preferably, specific binding refers to a molecule having a Kd at least 4-fold, 6-fold, 8-fold or 10-foldless for the particular polypeptide or epitope on a particular polypeptide than it does for a non-specific target. Alternatively, specific binding can be expressed as a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or less.

The person skilled in the art will appreciate that there exist many mechanisms for inhibiting VEGF-C or VEGF-D activity, VEGFR-3-mediated signaling or lymphangiogenesis. The principal aim is to reduce receptor signaling. Some examples will be described below, but such a list is not intended to be limiting.

Antibody Inhibitors

The term "antibody" is used in the broadest sense and specifically covers, for example, polyclonal antibodies, monoclonal antibodies (including antagonist and neutralizing antibodies), antibody compositions with polyepitopic specificity, single chain antibodies, and fragments of antibodies, provided that they exhibit the desired biological or immunological activity.

An "antibody inhibitor" will specifically bind to a particular polypeptide or epitope on a particular polypeptide without substantially binding to any other polypeptide or polypeptide epitope. Such binding will partially or fully block, neutralize, reduce or antagonize VEGF-C or VEGF-D activity or a biological activity of a molecule that facilitates VEGFR-3-mediated signaling or lymphangiogenesis. Such target molecules include VEGFR-3, VEGFR-2, VEGF-C and VEGF-D, for example.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or non-proteinaceous solutes. Generally, the antibody will be purified (1) to greater than 95% by weight of antibody as determined by the Lowry method, and most preferably more than 99% by weight, (2) to a degree sufficient to obtain at least 15 residues of N terminal or internal amino acid sequence by use of a spinning cup sequenator, or (3) to homogeneity by SDS PAGE under reducing or non-reducing conditions using Coomassie blue or, preferably, silver stain. An isolated antibody includes the antibody in situ within recombinant cells since at least one component of the antibody's natural environment will not be present. Ordinarily, however, isolated antibody will be prepared by at least one purification step.

Where antibody fragments are used, the smallest inhibitory fragment that specifically binds to the binding domain of the target protein is preferred.

Polyclonal Antibodies

Polyclonal antibodies are preferably raised in animals by multiple subcutaneous (s.c.) or intraperitoneal (i.p.) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups.

In one protocol for generating polyclonal antibodies, animals are immunized against the antigen, immunogenic conjugate, or derivative, by combining the antigen, conjugate or derivative with 3 volumes of Freund's complete adjuvant and injecting the solution intradermally at multiple sites. One month later, the animals are boosted with ⅕ to 1/10 the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

Monoclonal Antibodies

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method.

Monoclonal antibodies may be made using the hybridoma method in which a mouse or other appropriate host animal, such as a hamster, is immunized to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell.

The hybridoma cells thus prepared are seeded and grown in a suitable culture medium, which preferably contains one or more substances that inhibit the growth or survival of the unfused, parental myeloma cells (also referred to as fusion partner).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

Once hybridoma cells that produce antibodies of the desired specificity, affinity, and/or activity are identified, the clones may be subcloned by limiting dilution procedures and grown by standard methods. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxyapatite chromatography, gel electrophoresis, or dialysis.

DNA encoding the monoclonal antibodies is readily isolated and sequenced using conventional procedures. The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells.

Monoclonal antibodies or antibody fragments can be isolated from antibody phage libraries. High affinity (nM range) human antibodies can be generated by chain shuffling, as well as combinatorial infection and in vivo recombination as a strategy for constructing very large phage libraries. Thus, these techniques are viable alternatives to traditional monoclonal antibody hybridoma techniques for isolation of monoclonal antibodies.

The DNA that encodes the antibody may be modified to produce chimeric or fusion antibody polypeptides. The monoclonal antibodies used herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

Human and Humanized Antibodies

The anti-VEGF-C, anti-VEGF-D, anti-VEGFR-3-mediated signaling or anti-lymphangiogenesis antibodies used in the invention may comprise humanized antibodies or human antibodies. Generally, a "humanized antibody" is an antibody of non-human origin that has been modified using recombinant DNA techniques to circumvent the problem of a human's immune system reacting to an antibody as a foreign antigen. The standard procedure of producing monoclonal antibodies produces mouse antibodies. Although murine antibodies are very similar to human ones, there are differences. Consequently, the human immune system recognizes mouse antibodies as foreign, rapidly removing them from circulation and causing systemic inflammatory effects. "Humanized" forms of non-human (e.g., rodent) antibodies are chimeric antibodies that contain a reduced percentage of sequence derived from the non-human antibody. Various forms of humanized anti-VEGF-C, anti-VEGF-D, anti-VEGFR-3-mediated signaling or anti-lymphangiogenesis antibodies are contemplated. Humanized antibodies may be intact antibodies, such as intact $IgG_1$ antibodies, antibody chains or fragments thereof (such as Fv, Fab, Fab', F(ab')$_2$, or other antigen-binding subsequences of antibodies). Humanized antibodies include human antibodies (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human antibody are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human antibody and all or substantially all of the FR regions are those of a human antibody consensus sequence. The humanized antibody optimally also will comprise at least a portion of an antibody constant region (Fc), typically that of a human antibody.

Various humanization strategies have been described in the prior art and it is envisaged that practice of the invention extends to the use of both known humanization strategies and any new strategies to be developed in the future. Examples of known humanization strategies include those described by Studnicka (U.S. Pat. No. 5,869,619) and Padlan (1991, Molec. Immunol., 28, 489-498), Winter (U.S. Pat. No. 5,225, 539) and Jones et al (1986, Nature, 321, 522-525), Queen et al. (U.S. Pat. No. 5,693,761) and Foote (U.S. Pat. No. 6,881, 557).

As an alternative to humanization, human antibodies can be generated. For example, it is now possible to produce transgenic animals (e.g., mice) that are capable, upon immunization, of producing a full repertoire of human antibodies in the absence of endogenous immunoglobulin production.

Alternatively, phage display technology can be used to produce human antibodies and antibody fragments in vitro, from immunoglobulin variable (V) domain gene repertoires from unimmunized donors. Phage display can be performed in a variety of formats. Several sources of V-gene segments can be used for phage display.

Antibody Fragments

"Antibody fragments" comprise a portion of an antibody, preferably the antigen binding or variable region of the intact antibody. Examples of antibody fragments include Fab, Fab', F(ab')$_2$, and Fv fragments; diabodies; linear antibodies; single chain antibody molecules; and multispecific antibodies formed from antibody fragments. Antibody fragments of particular interest are fragments that retain antigen-binding properties of the whole antibody, and are useful as inhibitors for practicing the invention.

Papain digestion of antibodies produces two identical antigen binding fragments, called "Fab" fragments, and a residual "Fc" fragment, a designation reflecting the ability to crystallize readily. Each Fab fragment is monovalent with respect to antigen binding, i.e., it has a single antigen binding site. Pepsin treatment of an antibody yields a single large F(ab')$_2$ fragment which roughly corresponds to two disulfide linked Fab fragments having divalent antigen binding activity and is still capable of cross linking antigen. Fab' fragments differ from Fab fragments by having additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Fv" is the minimum antibody fragment which contains a complete antigen recognition binding site. This fragment consists of a dimer of one heavy and one light chain variable region domain in tight, non covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single chain Fv" abbreviated as "scFv" are antibody fragments that comprise the VH and VL antibody domains connected into a single polypeptide chain. Preferably, the scFv polypeptide further comprises a polypeptide linker between the VH and VL domains which enables the scFv to form the desired structure for antigen binding.

In certain circumstances there are advantages of using antibody fragments, rather than whole antibodies. The smaller size of the fragments allows for rapid clearance from the circulation.

Various techniques have been developed for the production of antibody fragments. Traditionally, these fragments were derived via proteolytic digestion of intact antibodies. However, these fragments can now be produced directly by recombinant host cells. Fab, Fv and ScFv antibody fragments can all be expressed in and secreted from E. coli, thus allowing the facile production of large amounts of these fragments. Antibody fragments can be isolated from the antibody phage libraries. Alternatively, Fab'-SH fragments can be directly recovered from E. coli and chemically coupled to form F(ab')$_2$ fragments. According to another approach, F(ab')$_2$ fragments can be isolated directly from recombinant host cell culture. Fab and F(ab')$_2$ fragment with increased in vivo half-life comprising a salvage receptor binding epitope residues also may be used.

Other techniques for the production of antibody fragments will be apparent to the skilled practitioner. The antibody of choice is a single chain Fv fragment (scFv). Fv and scFv are the only species with intact combining sites that are devoid of constant regions; thus, they are suitable for reduced nonspecific binding during in vivo use. The antibody fragment may also be a "linear antibody", which may be monospecific or bispecific. The inhibitor also maybe a polypeptide or protein comprising an antibody or antibody fragment linked to another entity to form a fusion protein.

Bispecific Antibodies

Bispecific antibodies are antibodies that have binding specificities for at least two different epitopes. Bispecific antibodies can be prepared as full length antibodies or antibody fragments (e.g., F(ab')$_2$ bispecific antibodies).

Methods for making bispecific antibodies are known in the art. Traditional production of full length bispecific antibodies is based on the co-expression of two immunoglobulin heavy chain-light chain pairs, where the two chains have different specificities.

According to a different approach, antibody variable domains with the desired binding specificity (antibody-antigen combining sites) are fused to immunoglobulin constant domain sequences.

Bispecific antibodies include cross-linked or "heteroconjugate" antibodies. Heteroconjugate antibodies are composed of two covalently joined antibodies. It is contemplated that the antibodies may be prepared in vitro using known methods in synthetic protein chemistry, including those involving crosslinking agents. For example, one of the antibodies in the heteroconjugate can be coupled to avidin, the other to biotin. Heteroconjugate antibodies may be made using any convenient cross-linking methods. Suitable cross-linking agents and cross-linking techniques are well known in the art.

Techniques for generating bispecific antibodies from antibody fragments have also been described in the literature. For example, bispecific antibodies can be prepared using chemical linkage.

Recent progress has facilitated the direct recovery of Fab'-SH fragments from E. coli, which can be chemically coupled to form bispecific antibodies. Various techniques for making and isolating bispecific antibody fragments directly from recombinant cell culture have also been described.

The term "diabodies" refers to small antibody fragments prepared by constructing scFv fragments with short linkers (about 5 to 10 residues) between the VH and VL domains such that inter chain but not intra chain pairing of the V domains is achieved, resulting in a bivalent fragment, i.e., fragment having two antigen binding sites. Bispecific diabodies are heterodimers of two "crossover" scFv fragments in which the VH and VL domains of the two antibodies are present on different polypeptide chains.

According to an alternative "diabody" technology for making bispecific antibody fragments, the fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported.

Antibodies with more than two valencies are contemplated for use in the invention. For example, trispecific antibodies can be prepared.

Multivalent Antibodies

A multivalent antibody may be internalized (and/or catabolized) faster than a bivalent antibody by a cell expressing an antigen to which the antibodies bind. Antibodies that may be used in the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. A preferred dimerization domain comprises an Fc region or a hinge region. In this scenario, the antibody will comprise an Fc region and three or more antigen binding sites amino-terminal to the Fc region. A preferred multivalent antibody comprises three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-$(X_1)_n$-VD2-$(X_2)_n$-Fc, wherein VD1 is a first variable domain, VD2 is a second variable domain, Fc is one polypeptide chain of an Fc region, $X_1$ and $X_2$ represent an amino acid or polypeptide, and n is 0 or 1. For instance, the polypeptide chain(s) may comprise: $V_H$-$C_H$1-flexible linker-$V_H$-$C_H$1-Fc region chain; or $V_H$-$C_H$1-$V_H$-$C_H$1-Fc region chain. A multivalent antibody preferably further comprises at least two (and preferably four) light chain variable domain polypeptides. A multivalent antibody may, for instance, comprise from about two to about eight light chain variable domain polypeptides. The light chain variable domain polypeptides contemplated here comprise a light chain variable domain and, optionally, further comprise a CL domain.

Peptide and Peptide Mimetic Inhibitors

In another embodiment, the inhibitor of VEGF-D activity, VEGFR-3-mediated signaling or lymphangiogenesis is a peptide or peptide mimetic. The peptide or peptide mimetic may reduce receptor availability for native ligand binding.

As used herein, "peptide mimetic" and "peptidomimetic" are used interchangeably.

A peptide inhibitor is a peptide that binds specifically to a component of VEGF-C or VEGF-D activity, VEGFR-3-mediated signaling or lymphangiogenesis and inhibits or neutralizes the function of that component in the process of VEGF-C or VEGF-D activity, VEGFR-3-mediated signaling or lymphangiogenesis. Peptide inhibitors may be chemically synthesized using known peptide synthesis methodology or may be prepared and purified using recombinant technology. The preferred length of peptide inhibitors of VEGF-C or VEGF-D activity, VEGFR-3-mediated signaling or lymphangiogenesis is from about 6, 7, 8, 9 or 10 amino acid residues to about 100 amino acid residues. It is contemplated that longer peptides may prove useful. Peptide inhibitors may be identified without undue experimentation using well known techniques. In this regard, it is noted that techniques for screening peptide libraries for peptides that are capable of specifically binding to a polypeptide target are well known in the art.

For any of the foregoing peptides, one preferred variation involves peptides that have been modified to comprise an intramolecular bond between two non-adjacent amino acid residues of the primary sequence, thereby forming a cyclic peptide. For example, in one variation, the peptide comprises a pair of cysteine residues, such as amino- and carboxy-terminal cysteines, and the intramolecular bond comprises a disulfide bond between the cysteines. However, organic chemists and peptide chemists are capable of synthesizing intramolecular bonds between a wide variety of amino acids using conventional techniques.

Nucleic Acid Molecules

Antisense Molecules

In yet another embodiment, the inhibitor of VEGF-C or VEGF-D activity, VEGFR-3-mediated signaling or lymphangiogenesis is an antisense molecule that reduces transcription and/or translation of a component of VEGF-C or VEGF-D activity, VEGFR-3-mediated signaling or lymphangiogenesis, thereby reducing VEGF-C or VEGF-D activity, VEGFR-3-mediated signaling or lymphangiogenesis.

The antisense molecule comprises RNA or DNA prepared using antisense technology, where, for example, an antisense RNA or DNA molecule acts to block directly the translation of mRNA by hybridizing to targeted mRNA and preventing protein translation. Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to reduce or block expression of a component of VEGF-C or VEGF-D activity, VEGFR-3-mediated signaling or lymphangiogenesis, and thus VEGF-C or VEGF-D activity, VEGFR-3-mediated signaling or lymphangiogenesis. Such oligonucleotides can also be delivered to cells such that the antisense RNA or DNA may be expressed in vivo to inhibit production of components of VEGF-C or VEGF-D activity, VEGFR-3-mediated signaling or lymphangiogenesis.

Inhibitors of VEGF-C or VEGF-D activity or signaling mediated by VEGFR-3, or lymphangiogenesis include antisense or sense oligonucleotides comprising a single-stranded nucleic acid sequence (either RNA or DNA) capable of binding to target mRNA (sense) or DNA (antisense) sequences. Such a fragment generally comprises about 10 to 40 nucleotides in length, preferably at least about 14 nucleotides, preferably from about 14 to 30 nucleotides.

Antisense or sense oligonucleotides further comprise oligonucleotides having modified sugar-phosphodiester backbones that are resistant to endogenous nucleases, or are covalently linked to other moieties that increases affinity of the oligonucleotide for a target nucleic acid sequence, or intercalating agents to modify binding specificities of the antisense or sense oligonucleotide for the target nucleotide sequence.

Small Interfering RNA (siRNA)

In one embodiment, it is envisaged that siRNA will inhibit VEGF-C or VEGF-D activity, VEGFR-3-mediated signaling or lymphangiogenesis. "siRNA" or "RNAi" are double-stranded RNA molecules, typically about 21 nucleotides in length, that are homologous to a gene or polynucleotide that encodes the target gene and interfere with the target gene's expression.

Nucleic Acid Molecules in Triple-Helix Formation

In another embodiment, the inhibitor of VEGF-C or VEGF-D activity, VEGFR-3-mediated signaling or lymphangiogenesis comprises nucleic acid molecules in triple-helix formation. Nucleic acid molecules in triple-helix formation used to inhibit transcription should be single-stranded and composed of deoxynucleotides. A DNA oligonucleotide is designed to be complementary to a region of the gene involved in transcription. The base composition of these oligonucleotides is designed such that it promotes triple-helix formation via Hoogsteen base-pairing rules, which generally require sizeable stretches of purines or pyrimidines on one strand of a duplex.

Ribozymes

In a related embodiment, the inhibitor of VEGF-C or VEGF-D activity, VEGFR-3-mediated signaling or lymphangiogenesis is a ribozyme that reduces transcription of a component of VEGF-C or VEGF-D activity or signaling mediated by VEGFR-3, or a lymphangiogenic component.

A "ribozyme" is an enzymatic RNA molecule capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques.

Small Molecule Inhibitors

In a further embodiment, the inhibitor of VEGF-C or VEGF-D activity, VEGFR-3-mediated signaling or lymphangiogenesis is a small molecule.

A "small molecule" is defined herein to have a molecular weight below about 2000 daltons, and preferably below about 500 Daltons. Potential inhibitors of VEGF-C or VEGF-D activity, VEGFR-3-mediated signaling or lymphangiogenesis include small molecules that bind to the active site, the receptor binding site, or growth factor or other relevant binding site of components of VEGF-C or VEGF-D activity or VEGFR-3-mediated signaling, or lymphangiogenesis, thereby blocking the normal biological activity of VEGF-C or VEGF-D, VEGFR-3-mediated signaling or lymphangiogenesis. Examples of small molecules include, but are not limited to, synthetic non-peptidyl organic or inorganic compounds.

Small molecule inhibitors of VEGF-C or VEGF-D activity, VEGFR-3-mediated signaling or lymphangiogenesis may be identified without undue experimentation using known techniques and chemically synthesized using known methodology. In this regard, it is noted that techniques for screening organic molecule libraries for molecules that are capable of binding to a polypeptide target are known in the art.

Inhibition of Receptor Availability for Ligand Binding

Antibody Inhibitors

In one embodiment, the inhibitor of VEGF-C or VEGF-D activity, VEGFR-3-mediated signaling or lymphangiogenesis is an antibody. In a preferred embodiment, the inhibitor of VEGF-C or VEGF-D activity, VEGFR-3-mediated signaling or lymphangiogenesis is an anti-VEGFR-3 antibody that reduces VEGFR-3 availability for ligand binding.

Suitable antibodies for use in the methods of the invention and means for their production are disclosed in WO2000/021560 and WO1995/021868 and include a polyclonal or a monoclonal antibody that binds specifically to VEGFR-3 and blocks its signaling, a fragment of such an antibody, a chimeric antibody, a humanized antibody, and a bispecific antibody that binds specifically to VEGFR-3 and blocks its signaling and also binds to another antigen.

In a preferred embodiment, the antibody inhibitor is a humanized antibody. In another embodiment, the antibody inhibitor of VEGF-C or VEGF-D activity, VEGFR-3-mediated signaling or lymphangiogenesis comprises a Fab, Fab', or F(ab')$_2$ fragment, or a single chain Fv (scFv) fragment.

Persons skilled in the art will appreciate that in particular embodiments, the monoclonal antibody may comprise antibody 9D9F9, disclosed in WO2000/021560 or 2E11D11 disclosed in WO2003/006104. Alternatively monoclonal antibodies that specifically bind to VEGFR-3 and may be used according to the invention include antibodies MM0003-7G63, RM0003-5F63, C28G5, KLT9, ZMD.251, mF4-31C1 and hF4-3C5. A particularly preferred monoclonal antibody is hF4-3C5, a fully-humanized antagonist antibody to human VEGFR-3.

In an alternative embodiment, the inhibitor may comprise a bispecific antibody, particularly a diabody, that binds specifically to and neutralizes each of VEGFR-3 and a second target. One example of such a diabody is that derived from antibodies hF4-3C5 and IMC-1121, which binds specifically to and neutralizes each of VEGFR-3 and VEGFR-2.

An inhibitor of VEGF-C or VEGF-D activity, VEGFR-3-mediated signaling or lymphangiogenesis according to the present invention also includes in one embodiment an antibody, as described above, that inhibits or neutralizes the receptor tyrosine kinase activity of VEGFR-3.

Peptide and Peptide Mimetic Inhibitors

The person skilled in the art will appreciate that particular inhibitors of VEFD-C or VEGF-D activity, VEGFR-3-mediated signaling or lymphangiogenesis that can be employed in a particular embodiment of the present invention are disclosed in WO2000/021560, WO2001/052875, and WO2002/057299, which are incorporated herein by reference. In one embodiment, the inhibitor of VEGF-C or VEGF-D activity, VEGFR-3-mediated signaling or lymphangiogenesis comprises a peptide. Such a peptide to be used as an inhibitor of VEFC-C or VEGF-D activity, VEGFR-3-mediated signaling or lymphangiogenesis can be generated by random peptide synthesis, by recombinant means from random oligonucleotides, or a peptide may be selected from a phage display library, according to the disclosure of WO2002/057299 and WO2000/021560 and methods standard in the art. Such a peptide can be identified with the aid of the VEGFR-3 extracellular domain.

In a particular embodiment, the peptide inhibitor of VEGF-C or VEGF-D activity, VEGFR-3-mediated signaling or lymphangiogenesis comprises the amino acid sequence GYWX$_1$X$_2$X$_3$W (SEQ ID NO: 32), wherein X$_1$, X$_2$, and X$_3$ comprise amino acids and wherein the peptide binds VEGFR-3, according to WO2002/057299. In a related embodiment, the peptide inhibitor comprises the amino acid sequence GYWX$_1$X$_2$X$_3$WX$_4$ (SEQ ID NO: 33), wherein X$_4$ comprises an amino acid. In another embodiment, either of the preceding peptides may further comprise an amino- and carboxy-terminus cysteine residue. In a particular embodiment, the peptide comprises a cyclic peptide. In an alternative embodiment, the peptide comprises a peptide dimer that binds to VEGFR-3, and in a preferred form, the peptides comprising the dimer are the same, according to WO2002/057299.

In one embodiment, the peptidomimetic inhibitor is a monomeric monocyclic peptide inhibitor or dimeric bicyclic peptide inhibitor. Preferably, such peptidomimetic inhibitors are based on the peptide sequence of exposed loops of growth factor proteins, for example, loops 1, 2, and 3 of VEGF-D. In a preferred embodiment, the peptidomimetic inhibitor comprises any one of: CASELGKSTNTFC (SEQ ID NO: 42); CNEESLIC (SEQ ID NO: 43); or CISVPLTSVPC (SEQ ID NO: 44).

In one embodiment, the peptide mimetic inhibitor is prepared by the methods disclosed in WO2001/052875 and WO2002/057299. Peptides that may be used as inhibitors of VEGF-D activity, VEGFR-3-mediated signaling or lymphangiogenesis are disclosed in WO2000/021560. Such peptides include a polypeptide comprising a fragment or analog of a vertebrate VEGF-C polypeptide, wherein the polypeptide and fragment or analog are capable of binding to VEGFR-3, but do not activate signaling, and a polypeptide comprising a fragment or analog of a vertebrate VEGF-C or VEGF-D polypeptide, wherein the polypeptide and fragment or analog are capable of binding to VEGFR-3, but do not activate signaling.

The person skilled in the art will appreciate that inhibitors of VEGF-D activity, VEGFR-3-mediated signaling or lymphangiogenesis inhibitors according to WO2002/057299 include peptides comprising the sequence YIGYWLTIWGY$_2$, wherein Y, and Y$_2$ are amino acids. In one variation, the peptide is made cyclic by a bond between Y and Y$_2$. In a specific preferred embodiment, the peptide comprises the sequence CGYWLTIWGC (SEQ ID NO: 42). Other peptide inhibitors comprise any of the following amino acid sequences: SGYWWDTWF (SEQ ID NO: 1), SCYWRDTWF (SEQ ID NO: 2), KVGWSSPDW (SEQ ID NO: 3), FVGWTKVLG (SEQ ID NO: 4), YSSSMRWRH (SEQ ID NO: 5), RWRGNAYPG (SEQ ID NO: 6), SAVFRGRWL (SEQ ID NO: 7), WFSASLRFR (SEQ ID NO: 8), WQLGRNWI (SEQ ID NO: 9), VEVQITQE (SEQ ID NO: 10), AGKASSLW (SEQ ID NO: 11), RALDSALA (SEQ ID NO: 12), YGFEAAW (SEQ ID NO: 13), YGFLWGM (SEQ ID NO: 14), SRWRILG (SEQ ID NO: 15), HKWQKRQ (SEQ ID NO: 16), MDPWGGW (SEQ ID NO: 17), RKVWDIR (SEQ ID NO: 18), VWDHGV (SEQ ID NO: 19), CWQLGRNWIC (SEQ ID NO: 20), CVEVQITQEC (SEQ ID NO: 21), CAGKASSLWC (SEQ ID NO: 22), CRALDSALAC (SEQ ID NO: 23), CYGFEAAWC (SEQ ID NO: 24), CYGFLWGMC (SEQ ID NO: 25), CSRWRILGC (SEQ ID NO: 26), CHKWQKRQC (SEQ ID NO: 27), CMDPWGGWC (SEQ ID NO: 28), CRKVWDIRC (SEQ ID NO: 29), CVWDHGVC (SEQ ID NO: 30), CGQMCTVWCSSGC (SEQ ID NO: 31), or conservative substitutions-variants thereof. Preferred peptides comprise these exact amino acid sequences, or sequences in which only one or only two conserved substitutions have been introduced. In another preferred variation, the peptides comprise amino- and carboxy-terminal cysteines, which permit formation of cyclic molecules and dimers and multimers. In yet another variation, peptide inhibitors include the amino acid sequence GYWXIX$_2$X$_3$W (SEQ ID NO: 32), wherein X, X$_2$, and X$_3$ comprise amino acids, the amino acid sequence GYWX, XZX$_3$WX$_4$ (SEQ ID NO: 33), wherein X$_4$ comprises an amino acid. In still another variation, these peptides further comprise amino- and carboxy-terminal cysteine residues.

Nucleic Acid Inhibitors

In a preferred embodiment, the invention envisages use of a VEGFR-3 antisense RNA, as disclosed in WO2000/021560, to inhibit the translation of VEGFR-3-encoding mRNA to eliminate or downregulate levels of VEGFR-3. Similarly, siRNA or nucleic acids in triple helix formation could be used to reduce VEGFR-3 availability for ligand binding.

Small Molecule Inhibitors

In a preferred embodiment, the small molecule is a small molecule inhibitor of receptor tyrosine kinase activity. In a more preferred embodiment, the small molecule comprises PTK787/ZK22854, AZP2171, ZK991, KRN633, MAZ51, sorafenib, sunitinib (SU11248), axitinib (AG013736), vandetanib (ZD6474), or 3-(indole-3-yl)-4-(3,4,5-trimethoxyphenyl)-1H-pyrrole-2,5-dione.

Inhibition of Ligand Availability for Receptor Binding

Antibody Inhibitors

According to one embodiment, inhibition of VEGF-C or VEGF-D activity, VEGFR-3-mediated signaling or lymphangiogenesis can be achieved using antibodies that specifically bind and neutralize ligands for VEGFR-3, that is, VEGF-C and/or VEGF-D. Antibodies similar to anti-VEGFR-3 antibodies described above are contemplated. Suitable antibodies and their means for production are disclosed in WO2000/021560. The person skilled in the art will appreciate that antibodies that bind specifically to VEGF-D and may be used according to the invention include monoclonal antibodies 2F8, 4A5 (also known as VD1), 4E10, 5F12, 4H4 and 3C10 disclosed in WO2000/037025. A particularly preferred antibody is 4A5, and in particular, a humanized version thereof. In another embodiment, the chimeric or humanized antibody comprises SEQ ID NO: 46 and SEQ ID NO: 47, or the antibody comprises any one of SEQ ID NOs: 48 to 50 and any one of SEQ ID NOs: 51 to 53, as disclosed in WO2005/087177. Alternatively monoclonal antibodies that may be used according to the invention include 28AT743.288.48, MM0007-7E79, RM0007-8C35, 78902, 78923, 78939, and 90409.

Similarly, monoclonal antibodies that bind VEGF-C may be employed. The anti-VEGF-C antibodies will specifically bind to human VEGF-C or a biologically active fragment thereof, e.g. the mature fully-processed form. Such binding will partially or fully block, neutralize, reduce or antagonize VEGF-C activity. Suitable examples of such antibodies include antibodies 103, MM0006-2E65 and 193208. Further examples of such antibodies are found in U.S. Pat. No. 7,208,582 and U.S. Pat. No. 7,109,308.

One example of an anti-VEGF-C antibody is a monoclonal antibody that competitively inhibits the binding to VEGF-C of monoclonal anti-VEGF-C antibody 69D09 produced by hybridoma ATCC PTA-4095 or having the heavy and light chain amino acid sequences as follows:

```
                                                      SEQ ID NO: 34
EVRLLESGGG   LVQPGGSLRL   SCAASGFTFR   PRAMAWVRQA   PGKGLEWVSS
         10           20           30           40           50

ISAQGASAYY   ADSVKGRFTI   SRDNSKNTLY   LQMNSLRAED   TAVYYCARDL
         60           70           80           90          100

SVSGFGPWGR   GTMVTVSSAS   TKGPSVFPLA   PSSKSTSGGT   AALGCLVKDY
        110          120          130          140          150

FPEPVTVSWN   SGALTSGVHT   FPAVLQSSGL   YSLSSVVTVP   SSSLGTQTYI
        160          170          180          190          200

CNVNHKPSNT   KVDKRVEPKS   CDKTHTCPPC   PAPELLGGPS   VFLFPPKPKD
        210          220          230          240          250

TLMISRTPEV   TCVVVDVSHE   DPEVKFNWYV   DGVEVHNAKT   KPREEQYNST
        260          270          280          290          300

YRVVSVLTVL   HQDWLNGKEY   KCKVSNKALP   APIEKTISKA   KGQPREPQVY
        310          320          330          340          350

TLPPSREEMT   KNQVSLTCLV   KGFYPSDIAV   EWESNGQPEN   NYKTTPPVLD
        360          370          380          390          400

SDGSFFLYSK   LTVDKSRWQQ   GNVFSCSVMH   EALHNHYTQK   SLSLSPGK
        410          420          430          440        448
Sequence of anti-VEGF-C antibody heavy chain SEQ ID NO: 35
SYELTQPPSS   SGTPGQRVTI   SCSGSSSNIG   RHTVSWYQQV   PGTAPKLLIY
         10           20           30           40           50

SDDHRPSGVP   DRFSASKSGT   SASLTITGLQ   SEDEADYYCA   AWDDSLNGPW
         60           70           80           90          100

VFGGGTKLTV   LGQPKAAPSV   TLFPPSSEEL   QANKATLVCL   ISDFYPGAVT
        110          120          130          140          150

VAWKADSSPV   KAGVETTTPS   KQSNNKYAAS   SYLSLTPEQW   KSHRSYSCQV
        160          170          180          190          200

THEGSTVEKT   VAPTECS
        210        b 217
Sequence of anti-VEGF-C antibody light chain
```

Another example of an anti-VEGF-C antibody is a monoclonal antibody that binds to the same epitope as the monoclonal anti-VEGF-C antibody 69D09 produced by hybridoma ATCC PTA-4095 or a monoclonal antibody having the heavy and light chain amino acid sequences shown above. In one embodiment, the anti-VEGF-C antibody is a fully-human anti-VEGF-C monoclonal antibody, including but not limited to 69D09 antibody or fragment thereof. The anti-VEGF-C antibody may be a humanized antibody.

Preferably, the anti-VEGF-C antibody is a human antibody produced by deposited hybridoma ATC PTA-4095 (also referred to herein as "VGX-100") or having the heavy and light chain amino acid sequences shown above.

Alternatively, antibodies may bind proprotein convertases, enzymes responsible for processing VEGF-C and VEGF-D from their prepro-forms to their activated forms, and reduce, inhibit or neutralize such activity thereby limiting the amount of proteolytically processed ligand available for binding to VEGFR-3. Again, antibodies corresponding with anti-VEGFR-3 antibodies described above are envisaged. Such antibodies are disclosed in WO05/112971 and include neutralizing antibodies to inhibit the biological action of proprotein convertases.

Peptide Inhibitors

Inhibitors of VEGF-C or VEGF-D activity, VEGFR-3-mediated signaling or lymphangiogenesis as used in the present invention include inhibitors of proprotein convertases. As noted, one class of inhibitor of proprotein convertases comprises antibodies. Another class of inhibitor of proprotein convertases includes peptide inhibitors.

Peptide inhibitors of proprotein convertases are disclosed in WO05/112971 and include prosegments of proprotein convertases, inhibitory variants of anti-trypsin and peptidyl haloalkylketone inhibitors.

Representative inhibitory prosegments of proprotein convertases include the inhibitory prosegments of PC5A (also known as PC6A), PC5B (also known as PC6B), PACE4, PC1 (also known as PC3), PC2, PC4, PC7 and Furin. A representative inhibitory variant of anti-trypsin is α-1 antitrypsin Portland, an engineered variant of naturally occurring antitrypsin that inhibits multiple proprotein convertases. Representative peptidyl halomethyl ketone inhibitors include decanoyl-Arg-Val-Lys-Arg-chloromethylketone (Dec-RVKR-CMK), decanoyl-Phe-Ala-Lys-Arg-chloromethylketone (Dec-FAKR-CMK), decanoyl-Arg-Glu-Ile-Arg-chloromethylketone (Dec-REIR-CMK), and decanoyl-Arg-Glu-Lys-Arg-chloromethylketone (Dec-REKR-CMK). These inhibitors of proprotein convertases, such as Dec-RVKR-CMK or the inhibitory prosegments of proprotein convertases, can be used to block the activation of VEGF-C and VEGF-D and thereby inhibit VEGF-C or VEGF-D activity, VEGFR-3-mediated signaling or lymphangiogenesis induced by partially processed or fully processed VEGF-C or VEGF-D.

Soluble Receptors

According to another embodiment, VEGF-C or VEGF-D activity, VEGFR-3-mediated signaling or lymphangiogenesis can be inhibited using soluble receptors that bind VEGFR-3 ligands. Soluble receptors capable of binding VEGF-C and VEGF-D, thereby inhibiting VEGF-C or VEGF-D activity or signaling via VEGFR-3, are disclosed in WO2000/023565, WO2000/021560 and WO2002/060950. Such inhibitors of VEGF-D activity, VEGFR-3-mediated signaling or lymphangiogenesis inhibitors include soluble VEGFR-2, VEGFR-3, NRP-1, and NRP-2.

Nucleic Acid Inhibitors

In another embodiment of the invention, antisense oligonucleotides are used as inhibitors of proprotein convertases. The antisense oligonucleotides preferably inhibit expression of proprotein convertases by inhibiting transcription or translation of proprotein convertases. In a further embodiment, the antagonizing agent is small interfering RNAs (siRNA, also known as RNAi, RNA interference nucleic acids). Also contemplated are methods of inhibiting the target gene expression or target protein function utilizing ribozymes and triplex-forming nucleic acid molecules.

Similarly, in a related embodiment, antisense, siRNA and ribozyme inhibitors directed to VEGF-C and/or VEGF-D are included as inhibitors of VEGF-C or VEGF-D activity, VEGFR-3-mediated signaling or lymphangiogenesis exerting their effects by reducing transcription and/or translation of VEGF-C and VEGF-D.

Peptide and Peptide Mimetic Inhibitors

According to one embodiment, the inhibitor to be used in the invention comprises a peptide that reduces the availability of ligand to bind to VEGFR-3. Such a peptide can be generated by random peptide synthesis, by recombinant means from random oligonucleotides, or a peptide may be selected from a phage display library by methods standard in the art. In a particular embodiment, the peptide will be derived from VEGFR-3 or VEGFR-2 and will bind specifically to VEGF-C or VEGF-D such that the ligand available for binding to native VEGFR-3 is reduced. Such a peptide may be identified with the aid of the VEGF-C or VEGF-D.

Small Molecule Inhibitors

In one embodiment, the small molecule inhibitor is a small molecule inhibitor of a proprotein convertase. In a particular embodiment, the proprotein convertase is furin and the small molecule comprises B3 (CCG8294, naphthofluorescein disodium) or a derivative of 2,5-dideoxystreptamine.

Antibody Inhibitors Affecting Ligand-Receptor Complex

In one embodiment, the invention includes use of bispecific antibodies, as described above, as inhibitors of VEGF-C or VEGF-D activity, VEGFR-3-mediated signaling or lymphangiogenesis, specifically inhibiting ligand-receptor complexes.

Suitable antibodies and their means for production are disclosed in WO2000/021560 and include a bispecific antibody that binds specifically to an epitope or epitopes derived from a VEGFR-3-(VEGFR-3 ligand) complex (receptor-ligand complex) and blocks VEGFR-3 signaling.

Inhibition of Co-Receptor Interaction

Antibody Inhibitors Affecting Co-Receptors of VEGFR-3

In a further embodiment, inhibitors of VEGF-C or VEGF-D activity, VEGFR-3-mediated signaling or lymphangiogenesis include antibodies, as described above, that bind specifically to and reduce, inhibit or neutralize co-receptor binding to VEGFR-3. Such antibodies may be directed to a co-receptor, a ligand-co-receptor binary complex, a co-receptor-receptor binary complex, or a ligand-co-receptor-receptor ternary complex. Co-receptors include NRP-1 and NRP-2. The person skilled in the art will understand that monoclonal antibodies that specifically bind NRP-1 or NRP-2 and may be used according to the invention include antibodies 1B3, 3G6-2C5, AD5-17F6, 446915, 446921, 130603, 130604, 96009, 3B8, 54, 257103, 257107, A-12, and C-9. Alternatively, a bispecific antibody which specifically binds to NRP-2 receptor and a VEGF-C polypeptide, as disclosed in WO2003/029814, may be used according to the invention.

Peptide Inhibitors Affecting Co-Receptors of VEGFR-3

In another embodiment, a peptide inhibitor comprising a peptide dimer may target one or more receptors and/or co-receptors. Co-receptors include NRP-1 and NRP-2. As disclosed in WO2002/057299, in a particular embodiment, the peptide dimer comprises one peptide that binds VEGFR-3 and a second peptide that binds to any one of VEGFR-1, VEGFR-2, NRP-1, or NRP-2.

Small Molecule and Nucleic Acid Inhibitors Affecting Co-Receptors of VEGFR-3

According to the present invention, it is also envisaged that small molecules, antisense molecules, siRNA and ribozymes, as described above, can be utilized as inhibitors of VEGF-D activity, VEGFR-3-mediated signaling or lymphangiogenesis by targeting co-receptors that interact with VEGFR-3. Such co-receptors include NRP-1 and NRP-2.

Inhibition of Downstream Signaling

Alternatively, an inhibitor of VEGF-C or VEGF-D activity, VEGFR-3-mediated signaling or lymphangiogenesis according to any of the foregoing descriptions may disrupt downstream intracellular VEGFR-3 signaling, as disclosed in WO2000/021560.

Pharmaceutically Acceptable Carriers

Suitable ophthalmic carriers are known to those skilled in the art and all such conventional carriers may be employed in the present invention. Exemplary compounds incorporated to facilitate and expedite transdermal delivery of topical compositions into ocular or adnexal tissues include, but are not limited to, alcohol (ethanol, propanol, and nonanol), fatty alcohol (lauryl alcohol), fatty acid (valeric acid, caproic acid and capric acid), fatty acid ester (isopropyl myristate and isopropyl n-hexanoate), alkyl ester (ethyl acetate and butyl acetate), polyol (propylene glycol, propanedione and hexanetriol), sulfoxide (dimethylsulfoxide and decylmethylsulfoxide), amide (urea, dimethylacetamide and pyrrolidone derivatives), surfactant (sodium lauryl sulfate, cetyltrimethylammonium bromide, polaxamers, spans, tweens, bile salts and lecithin), terpene (d-limonene, alphaterpeneol, 1,8-cineole and menthone), and alkanone (N-heptane and N-nonane). Moreover, topically-administered compositions comprise surface adhesion molecule modulating agents including, but not limited to, a cadherin antagonist, a selectin antagonist, and an integrin antagonist. Thus, a particular carrier may take the form of a sterile, ophthalmic ointment, cream, gel, solution, or dispersion. Also including as suitable ophthalmic carriers are slow release polymers, e.g., "Ocusert" polymers, "Hydron" polymers, etc.

Stabilizers may also be used such as, for example, chelating agents, e.g., EDTA. Antioxidants may also be used, e.g., sodium bisulfite, sodium thiosulfite, 8-hydroxy quinoline or ascorbic acid. Sterility typically will be maintained by conventional ophthalmic preservatives, e.g., chlorbutanol, benzalkonium chloride, cetylpyridium chloride, phenyl mercuric salts, thimerosal, etc., for aqueous formulations, and used in amounts which are nontoxic and which generally vary from about 0.001 to about 0.1% by weight of the aqueous solution. Conventional preservatives for ointments include methyl and propyl parabens. Typical ointment bases include white petrolatum and mineral oil or liquid petrolatum. However, preserved aqueous carriers are preferred. Solutions may be manually delivered to the eye in suitable dosage form, e.g., eye drops, or delivered by suitable microdrop or spray apparatus typically affording a metered dose of medicament. Examples of suitable ophthalmic carriers include sterile, substantially isotonic, aqueous solutions containing minor amounts, i.e., less than about 5% by weight hydroxypropylmethylcellulose, polyvinyl alcohol, carboxymethylcellulose, hydroxyethylcelullose, glycerine and EDTA. The solutions are preferably maintained at substantially neutral pH and isotonic with appropriate amounts of conventional buffers, e.g., phosphate, borate, acetate, tris.

All publications and patents mentioned herein are hereby incorporated by reference in their entirety as if each individual publication or patent was specifically and individually indicated to be incorporated by reference. In case of conflict, the present application, including any definitions herein, will control.

EXAMPLES

Materials and Methods

Experimental Dry Eye Murine Model

Eight to ten week-old female C57BLI6 mice (Charles River Laboratory, Wilmington, Mass.) were used in accordance with the standards in the ARVO Statement for the Use of Animals in Ophthalmic and Vision Research. The research protocol was approved by the Schepens Eye Research Institute Animal Care and Use Committee. Dry eye was induced in murine eyes using a Controlled Environment Chamber (CEC) which exposes the mice to high-flow desiccated air. To achieve maximum ocular surface dryness, the conditions in CEC were supplemented with topical application of 1% atropine sulfate (Falcon Pharma, Fort Worth, Tex.) twice for the first 48 hours and subcutaneous injections of 0.1 ml of 5 mg/ml of scopolamine hydrobromide (Sigma-Aldrich, St. Louis, Mo.) three times a day, for the entire duration of the experiment.

RNA Isolation and Molecular Analysis Using Real Time Polymerase Chain Reaction

Five mice (10 eyes) were included in each group. Two corneas were pooled together to equal as one sample and stored at −80'C in Trizol (Invitrogen, Carlsbad, Calif.; catalog No. 15596026) until future use. Total RNA was isolated from these corneas using the RNeasy microkit (Qiagen, Valencia, Calif.; catalog No. 74004). Equal amounts of RNA were used to synthesize cDNA using SuperScript™ III Reverse Trancriptase (Invitrogen, Carlsbad, Calif.; catalog No. 18080) according to the manufacturer's recommendations. Real-Time PCR was performed using FAM-MGB dye labeled predesigned primers (Applied Biosystem, Foster City, Calif.) for GAPDH (assay ID.Mm999999 15_gl), VEGF-A (Mm00437304_ml), VEGF-C (Mrn00437313_ml), VEGF-D (Mm00438965_ml), VEGFR-2 (Mm00440099_ml), VEGFR-3 (Mm00433337_ml). 2.5 µl of cDNA was loaded in each well and assays were performed in duplicate. The GAPDH gene was used as the endogenous reference for each reaction. The results were normalized by the cycle threshold (CT) of GAPDH and the relative mRNA level in the normal mice was used as the normalized control.

Immunohistochemistry

The following primary antibodies were used for immunohistochemical staining: rat anti-mouse CD11b-FITC for monocytes/macrophages (BD Pharmingen, San Diego, Calif., 1:100), goat anti-mouse CD31 FITC as pan-endothelial marker (Santa Cruz Biotechnology, Santa Cruz, Calif., 1:100) and purified rabbit anti-mouse LYVE-1 as iymphatic endothelial marker (Abeam, MA, USA, 1:400). Respective isotypes were used as negative controls. Rhodamine conjugated goat anti-rabbit (BD Pharmingen, San Diego, Calif., 1:100) was the secondary antibody used.

Freshly excised corneas were washed in PBS, fixed in acetone for 15 minutes and then double stained with CD31 and LYVE-1 as described previously. To analyze infiltration of CD11b$^+$/LYVE-1 cells, corneas from three mice from each group were taken and cells were counted in 5-6 areas in the periphery (0.5 µm area from the limbus) of each cornea in a masked fashion, using epifluorescence microscope (model E800; Nikon, Melville, N.Y.) at 40× magnification. The mean number of cells was obtained by averaging the total number of cells in all the areas studied and the result was expressed as the number of positive cells per mm$^2$.

Morphometry of Lymphangiogenesis in the Cornea

Morphology of lymphatics was analyzed using an automated image analysis program written with Matlab (The Mathworks, Inc., Natick, Mass.). Lymphatics were isolated from digitized images with this program using standard computer vision techniques for image segmentation, including background isolation and subtraction, edge detection, and k-means clustering. This segmentation process generated binary images in which lymphatic vessels are represented by 1s and all other image content is represented by 0s. The resultant isolated lymphatic vessels were analyzed morphologically using two metrices, Lymphatic Area (LA) and Lymphatic Caliber (LC). LA represents the total surface area of the lymphatic vessels when projected into the plane of the image. LC is a summary measure of the diameters of the lymphatic vessels present. LC was measured using a computational technique that generates the largest diameter circle centered at each pixel inside a lymphatic vessel. The mean value across all pixels within lymphatic vessels was taken as an estimate of the mean LC for a given image.

Flow Cytometry

Draining LNs from DED (day 10) and normal mice were collected. Single cell suspension of LN cells was stained with the anti-CD11b-FITC and anti-Iab (MHC-II)-PE. Stained LN cells were then analyzed on an EPICS XL flow cytometer (Beckman Coulter). All the antibodies with their matched isotype controls were purchased from eBioscience.

Studies Involving Inhibition of Corneal Neo-Lymphangiogenesis Using an Anti-VEGF-C Antibody (Example 5 Onwards)

Anti-VEGF-C antibodies (VGX-100; Vegenics Limited, Australia) were administered intraperitonealy daily from day 1 to day 10 to DED mice. Mice were assessed clinically using corneal fluorescent staining. Tissues from cornea, conjunctiva and draining lymph nodes were examined for cellular and molecular pathological changes. In vivo blockade of VEGF-C suppresses corneallymphangiogenesis and ameliorates clinical signs of DED.

Statistical Analysis

A two-tailed Student's t-test was performed and P-values less than 0.05 were deemed statistically significant. Results are presented as the mean±SEM of at least three experiments.

Example 1

Demonstration and Quantification of Lymphatics in Dry Eye Corneas

Figure 2:
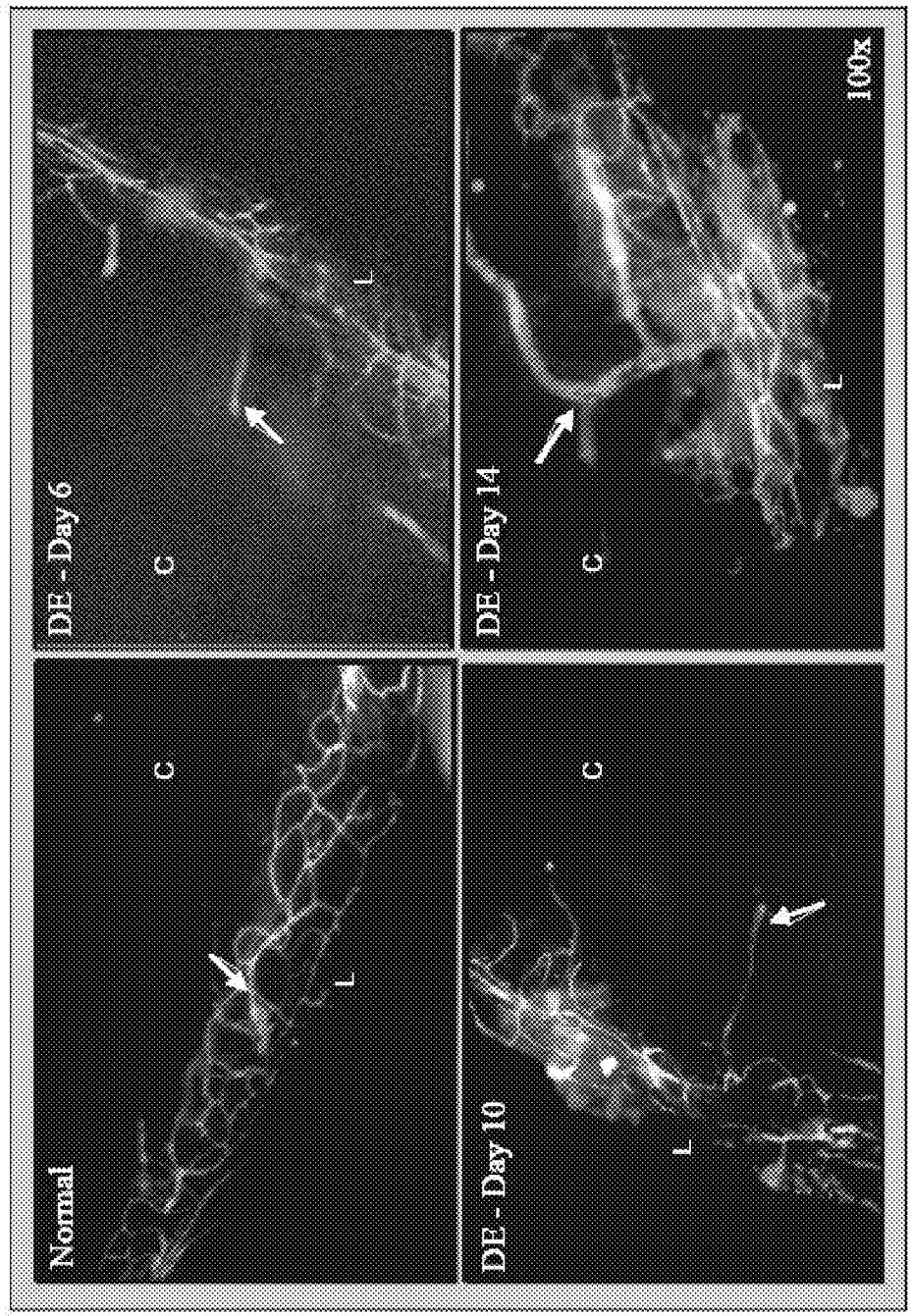
FIG. 2: Representative whole mount corneal immunofluorescence micrographs showing lymphatics (CD31$^{lo}$/LYVE-1$^{hi}$) in normal and dry eye (DE) at days 6, 10 and 14 (100× magnification).
Figure 3A:
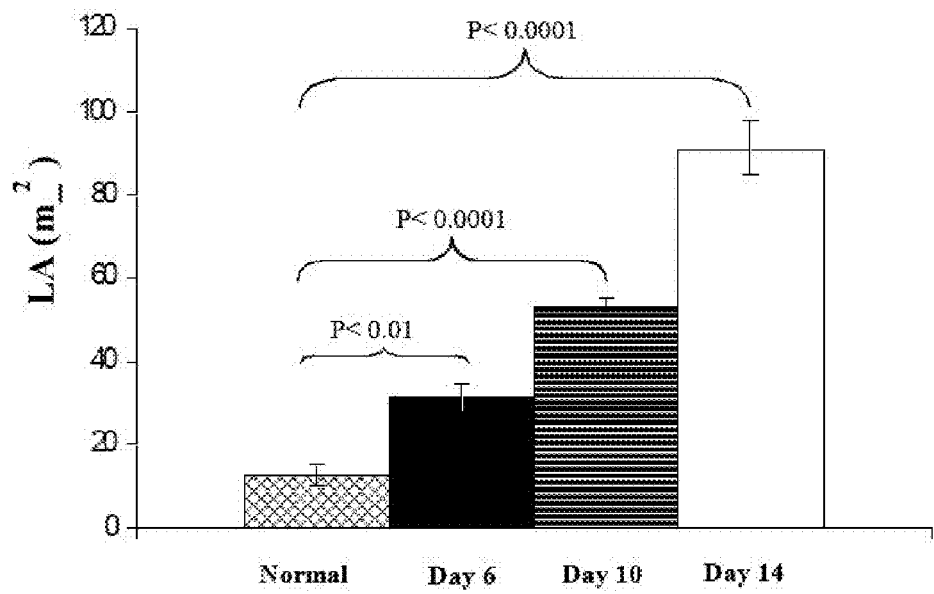
FIG. 3: Quantification of lymphatics in dry eye (DE) corneas. Morphometric analysis of corneal lymphangiogenesis in normal and DE days 6, 10 and 14 (100× magnification). Morphometric evaluation showed significant increase in lymphatic area (LA) in dry eye compared to normal corneas (FIG. 3a). Significant increase in lymphatic caliber (LC) in dry eye compared to normal corneas was noticed only at day 14 (FIG. 3b). Data from a representative experiment of three performed is shown as mean±S.E.M and each group consists of four to five mice.
Figure 3B:
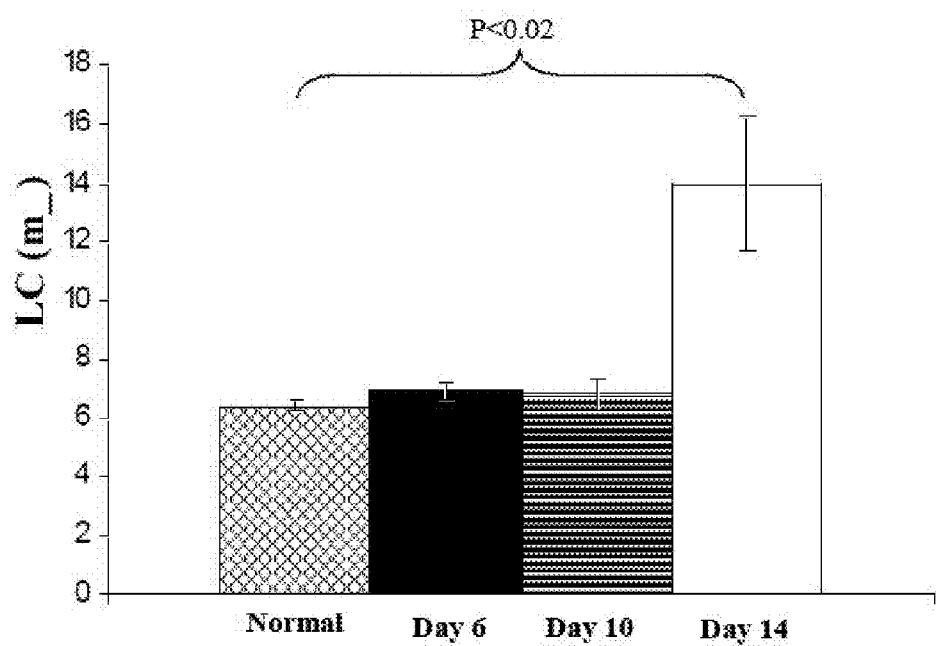

To determine whether DED induces growth of lymphatics into the cornea, and whether lymphatic growth is paralleled by growth of blood vessels, corneal whole mounts were double stained for CD31 (pan-endothelial marker) and LYVE-1 (lymphatic vascular endothelial marker) at days 0, 6, 10 and 14 and quantified for lymphangiogenesis. Blood vessels were identified as $CD31^{hi}/LYVE-1^-$ and lymph vessels were identified as $CD31^{lo}/LYVE-1^{hi}$. A significant increase in lymphatic area LA is seen in DED mice (FIG. 1 b). Morphometric analysis revealed small buds of lymphatic vessels arising from the limbal vascular arcade at an early time point (day 6), which increased in caliber (LC) and area (LA), and advanced towards the center of the cornea with DED progression (FIGS. 1 and 2). A significant increase in LA (FIG. 3a) was seen as early as day 6 (P<0.01) which continued until day 14 (P<0.0001). However, LC (FIG. 3b) was significantly increased from the normal only by day 14 (P<0.02). Remarkably, these lymphatics were not accompanied by growth of blood vessels at any given time point.

Example 2

Expression Levels of Different VEGF's and VEGFR's in Dry Eye Corneas

Figure 4:
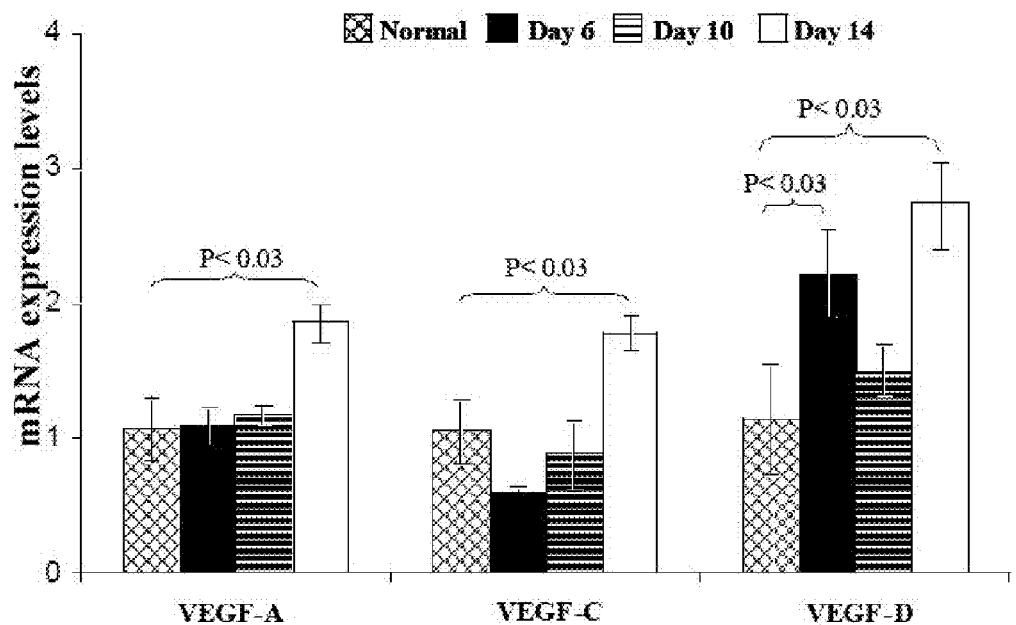
FIG. 4: Analysis of lymphangiogenic-specific growth factors. Real-time PCR analysis showing transcript levels of VEGF-A, VEGF-C and VEGF-D in the dry eye corneas at different time points. A significant increase in VEGF-D was seen at day 6 whereas VEGF-A and VEGF-C increased significantly only by day 14. Data from a representative experiment of three performed is shown as mean±S.E.M and each group consists of four to five mice.
Figure 5:
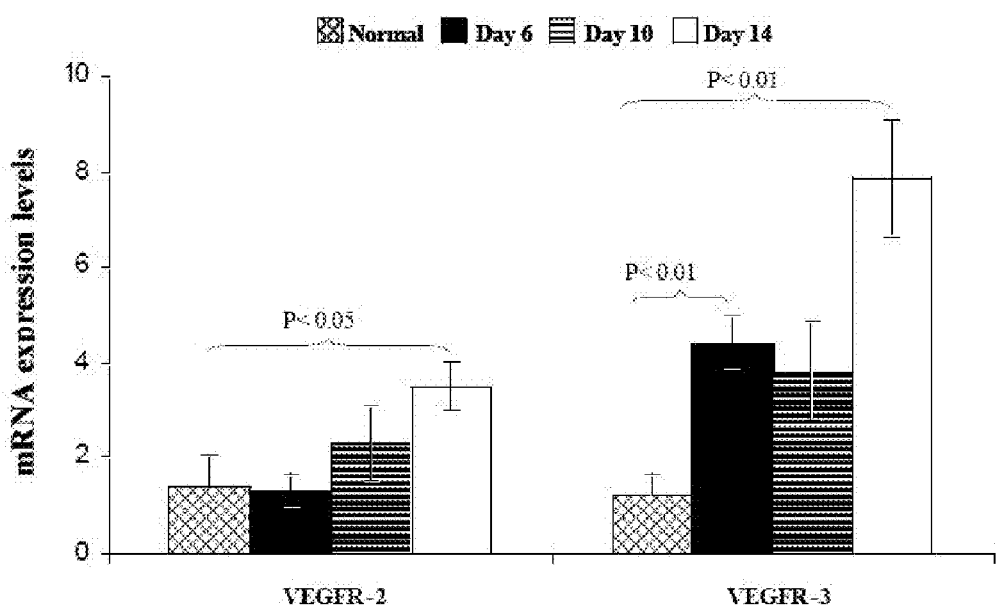
FIG. 5: Analysis of lymphangiogenic-specific growth factor receptors. Real-time PCR analysis showing transcript levels of VEGFR-2 and VEGFR-3 in the dry eye corneas at different time points. Significant increase in VEGFR-3 was seen earliest at day 6 but VEGFR-2 increased significantly later in disease at day 14. Data from a representative experiment of three performed is shown as mean±S.E.M and each group consists of four to five mice.

The development of lymphatic vessels is regulated by factors common to both hemangiogenesis and lymphangiogenesis. VEGF-C and VEGF-D are the classic lymphangiogenic factors and act by binding to their receptors VEGFR-2 and VEGFR-3, which are expressed on lymphatic endothelial cells. To determine the molecular mechanisms of lymphangiogenesis in DED, expression of different vascular endothelial growth factors and their receptors were quantified at indicated time points in the cornea using real time PCR. Amongst the VEGF species (FIG. 4), lymphangiogenic specific VEGF-D was not only the earliest to increase at day 6 (~2 folds; P<0.03) but also showed the maximum increase in expression at day 14 (~3 folds; P<0.03). Significant increased transcript expression of VEGF-A and VEGF-C was seen only by day 14 (P<0.03 for both). Similarly levels of lymphangiogenic specific VEGFR-3 were first to show a significant increase at day 6 (~4 folds; P<0.01) and continued to rise until day 14 (~8 folds; P<0.01). Though an overall trend toward increased expression was noticed with VEGFR-2 (primarily specific for blood vessel growth), significant increase (P<0.05) was appreciated only by day 14 (FIG. 5).

Example 3

Enumeration of CD11b/LYVE-1 Positive Cells in Dry Eye Corneas

Figure 6:
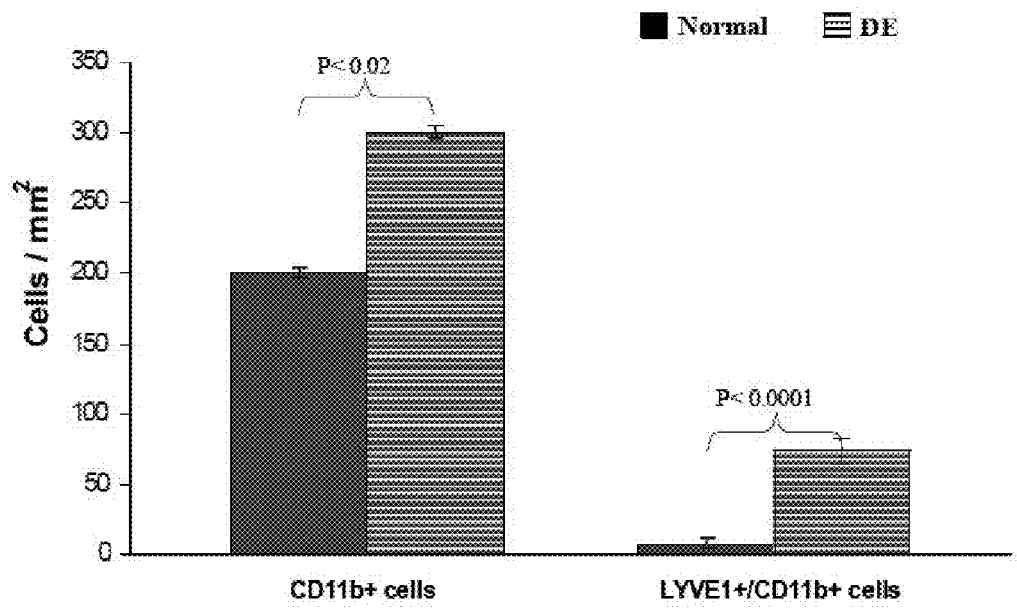
FIG. 6: Enuneration of corneal CD11b$^+$/LYVE-1$^+$ cells. A significant increase in the number of both CD11b$^+$ and double stained CD11$^{hi}$/LYVE-1$^+$ cells in the dry eye corneas as compared to normal. Data from a representative experiment of three performed is shown as mean±S.E.M and each group consists of four to five mice.

The normal cornea has a resident population of bone marrow-derived $CD11b^+$ monocyticmacrophage-lineage cells and the development of DED increases the number of $CD11b^+$ cells in the cornea. The role of macrophages in inflammatory lymphangiogenesis is well established. These $CD11b^+$ macrophages may also express various lymphatic endothelial markers, such as LYVE-1. To see what proportion of these $CD11b^+$ cells had lymphangiogenic potential, whole mount corneal tissues were double stained with CD11b and LYVE-1 at day 14. There was a significant increase in the number of both CD11b+(P<0.02) and $CD11b^+/LYVE-1^+$ (P<0.0001) cells in dry eye as compared to normal corneas (FIG. 6). In DED, about 25% of the $CD11b^+$ cells were positive for LYVE-1 where as only 4% of the $CD11b^+$ cells were positive for LYVE-1 in the normal corneas.

Example 4

Role of APC Homing

Figure 7:
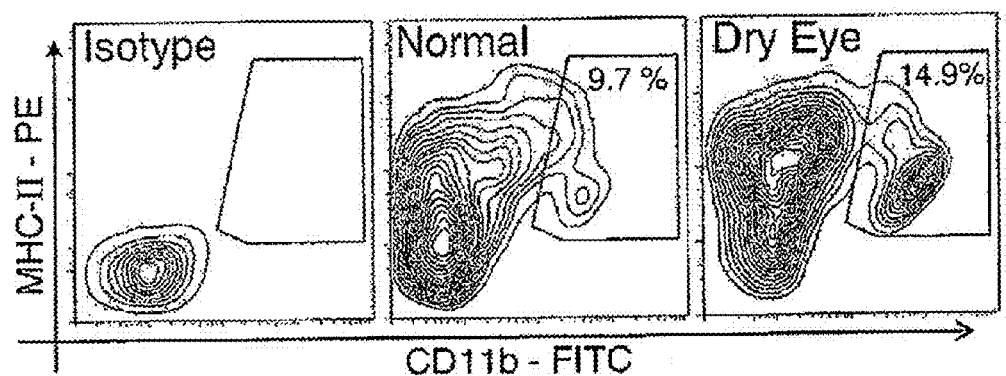
FIG. 7: Increased homing of mature MTIC-II+CD11b+ APC in the draining LN of DED mice. Flow cytometric analysis of draining lymph nodes showing significant increase in the frequencies of mature MHC-II$^+$ CD11b$^+$ APC in DED mice compared with normal mice. Data from a representative experiment of two performed is shown and each group consists of three mice.

It was next investigated whether corneal lymphangiogenesis in DED is associated with the increased homing of APC in the draining LN. Using flow cytometry, the frequencies of mature APC (MHC-II+CD11b+) in the draining LN of normal and DED mice were analysed (FIG. 7). Data showed a significant increase in the frequency of $MHC-II+CD11b^+$ APC in the LN cells of DED mice compared to those in the LN of normal mice (Range: 14.9-19.5% vs. 10-13.5%, p<0.05).

Example 5

Effect of In Vivo Blockade of Pro-Lymphangiogenesic VEGF-C on Dry Eye Disease

Dry eye was induced in murine eyes as described in the materials and methods.

Figure 8:
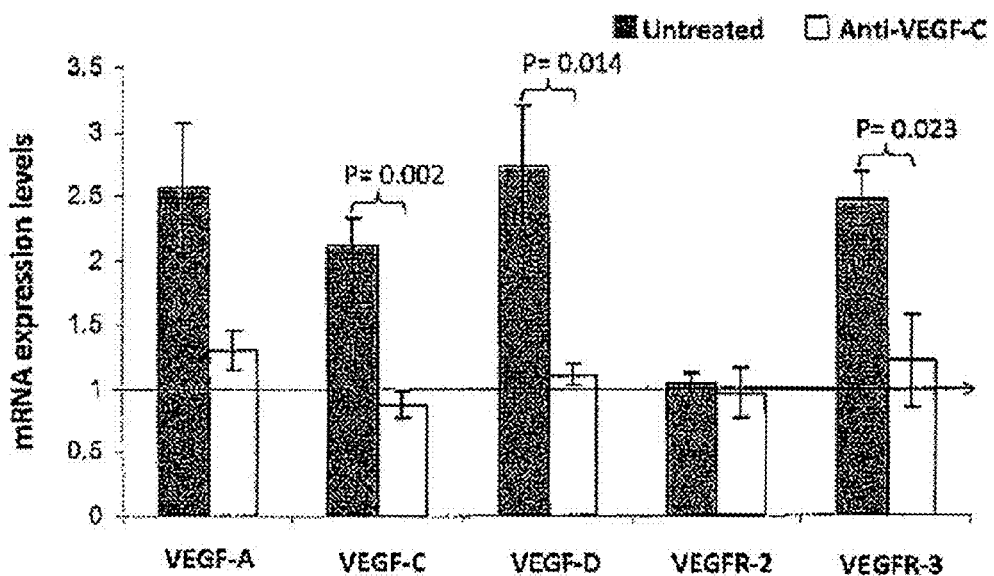
FIG. 8: Analysis of lymphangiogenic-specific growth factors and their receptors. Real-time PCR analysis showing transcript levels of VEGF-A, VEGF-C, VEGF-D, VEGFR-2 and VEGFR-3 in the dry eye corneas.
Figure 9:
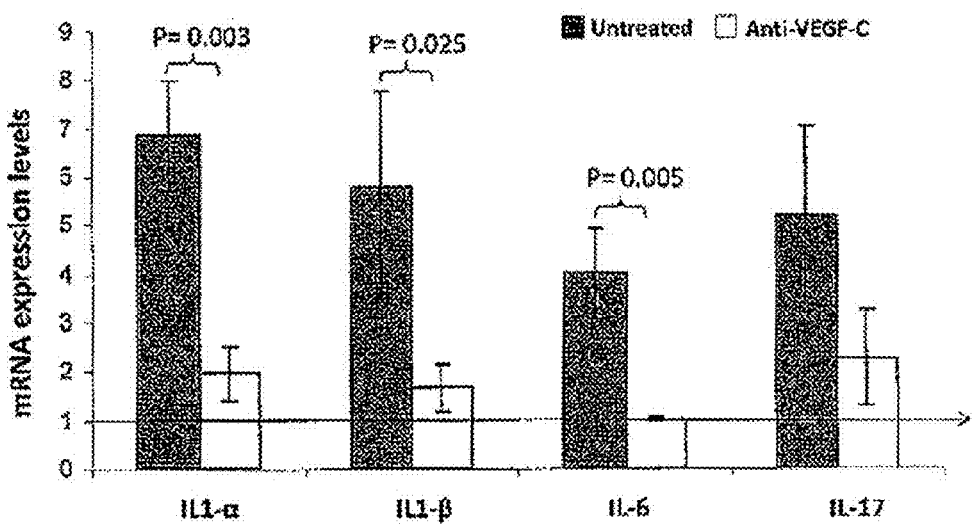
FIG. 9: Analysis of proinflammatory cytokines in conjunctiva. Real-time PCR analysis showing expression of cytokines IL-1α, IL-1β, IL-6, IL-17. The levels of all four cytokines in the conjunctiva showed significantly decreased expression in anti-VEGF-C treated DED mice as compared to those of untreated DED mice
Figure 10:
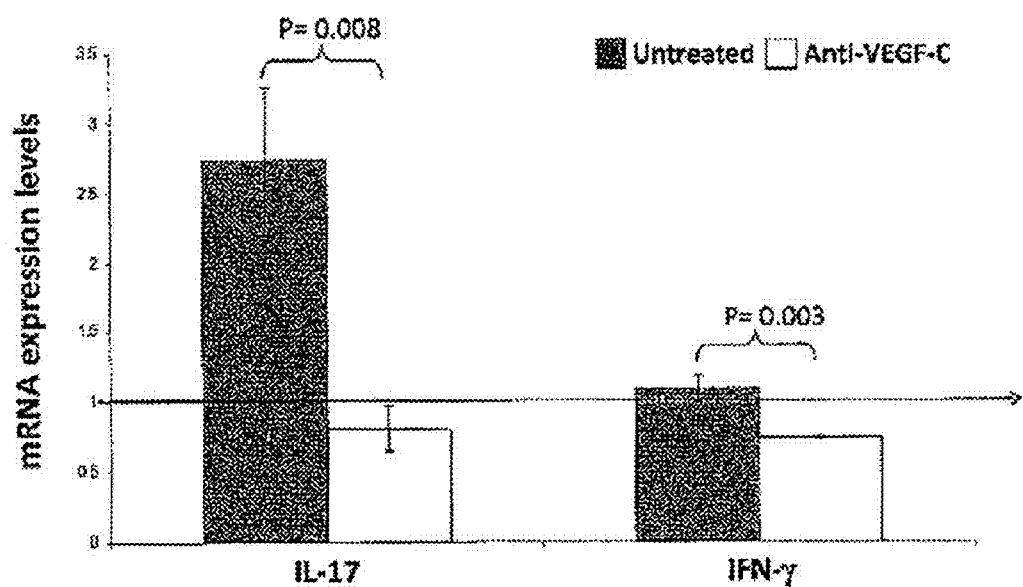
FIG. 10: Analysis of inflammatory cytokines in draining lymph nodes. Real-time PCR analysis for IL-17 (Th17 cells) and IFN-γ (Th1 cells). Draining lymph nodes of anti-VEGF-C treated DED mice showed significantly decreased induction of T-cell mediated autoimmune response compared untreated DED mice.

Real time PCR was performed to quantify expression of different VEGF growth factors (VEGF-A, VEGF-C, VEGF-D) and their receptors (VEGFR-2, VEGFR-3) in the cornea at days 6, 10 and 14 (FIG. 8) and to determine the levels of proinflammatory cytokines. IL-1α, IL-1β, IL-6, IL-17 in the conjunctiva showed significantly decreased expression in anti-VEGF-C treated DED mice as compared to those of untreated DED mice (FIG. 9). Draining lymph nodes of anti-VEGF-C treated DED mice showed significantly decreased induction of T-cell mediated autoimmune response compared untreated DED mice as determined by Real-time PCR analysis for IL-17 (Th17 cells) and IFN-γ (Th1 cells) (FIG. 10).

Figure 11:
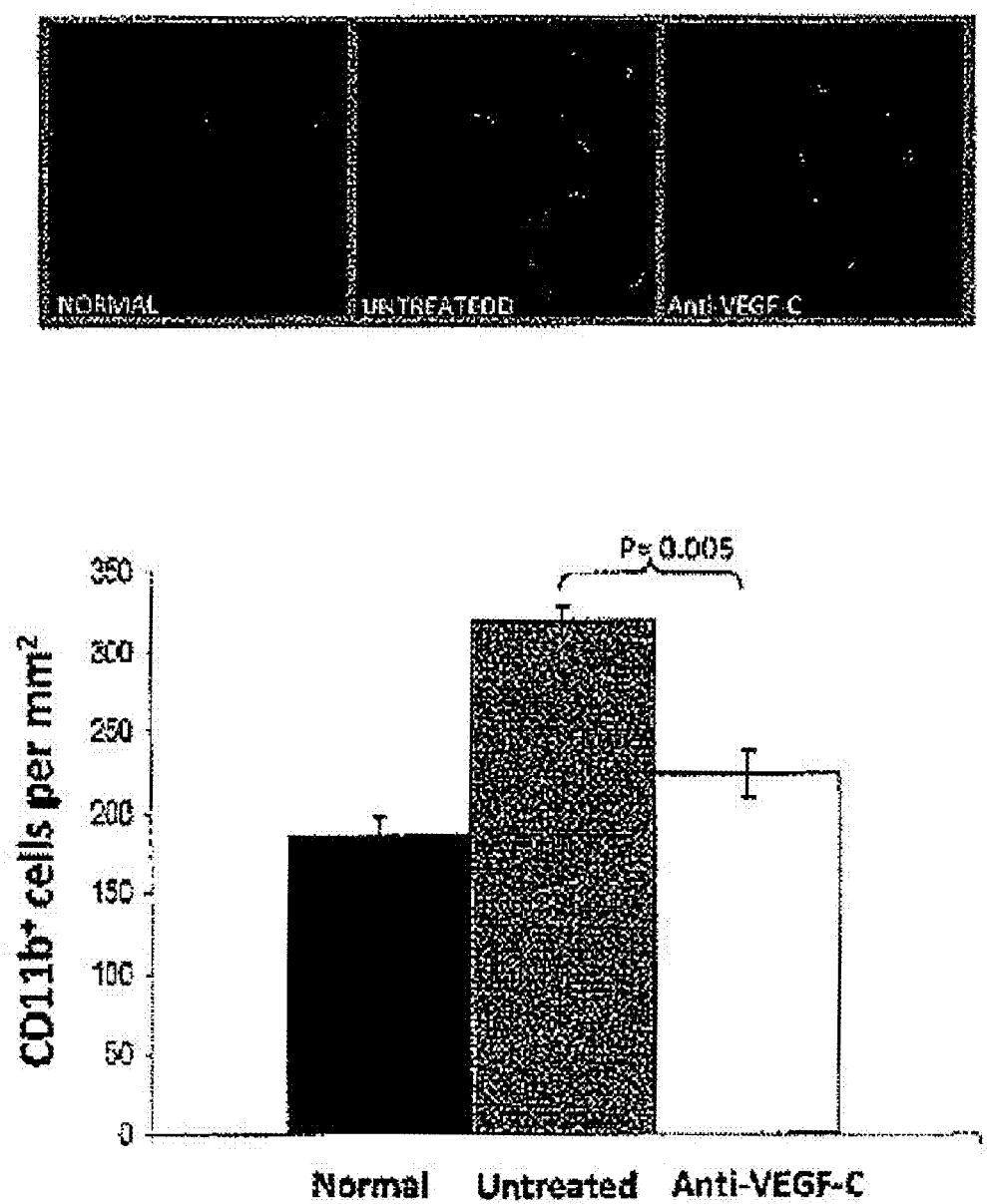
FIG. 11: Enumeration of CD11b$^+$ cells in DED corneas. Treatment with anti-VEGF-C antibodies significantly decreased infiltration of CD11b$^+$ cells (30%) in the DED corneas (day 14).

Enumeration of $CD11b^+/LYVE-1^+$ monocytic cells was done in the DED corneas at day 14 as described previously (FIG. 11). Treatment with anti-VEGF-C antibodies significantly decreased infiltration of $CD11b^+$ cells (30%) in the DED corneas.

Figure 12:
FIG. 12: Epifluorescent microscopic image of corneal wholemounts immunostained with CD31 and LYVE-1.
Figure 13:
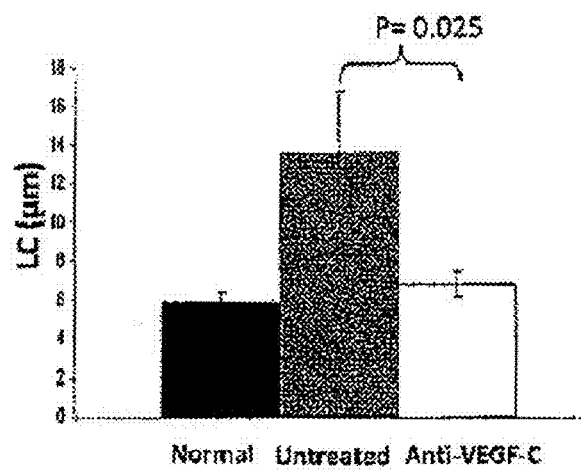
FIG. 13: Quantification of number of infiltrating CD11b+ cells per mm2 of cornea.
Figure 13:
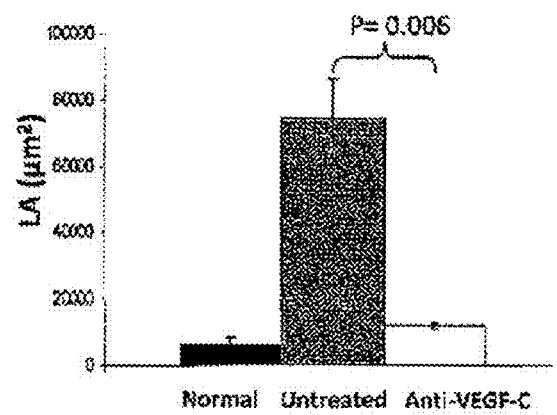

To determine whether DED induces growth of lymphatics into the cornea, and whether lymphatic growth is paralleled by growth of blood vessels, corneal whole mounts were double stained for CD31 (pan-endothelial marker) and LYVE-1 (lymphatic vascular endothelial marker) at days 0, 6, 10 and 14 and quantified for lymphangiogenesis as described previously. Lymphatics were seen growing toward the center of DED corneas (FIG. 12). Morphometric analysis showed significant increase in both lymphatic area (P<0.0001) and lymphatic caliber (P<0.02) at day 14 of disease (FIG. 13). These lymphatics were not accompanied by any new blood vessels. Lymphangiogenic specific VEGF-D and VEGFR-3 were the earliest to increase at day 6 followed by increase in VEGF-C, VEGF-A and VEGFR-2. Increased recruitment of $CD11b^+/LYVE-1^+$ monocytic cells to the cornea was also seen with disease.

These results demonstrate that low-grade inflammation associated with dry eye is an inducer of lymphangiogenesis without accompanied hemangiogenesis.

Clinical Relevance: Demonstration of selective lymphatic growth into dry eye corneas provides an important mechanistic link to adaptive (T cell-meditated) immunity by delineating how corneal antigen trafficking can occur to the lymphoid tissues.

Dry eye disease (DED) once thought to be solely due to deficiency of tears, is increasingly being recognized as an immune-mediated disorder) DED affects many millions of people with a wide spectrum of seminal features ranging from mild ocular discomfort to sight-threatening corneal complications such as persistent epithelial defects and sterile stromal ulceration) In the United States alone, more than 3.2 million women and 1.6 million men above the age of 50 years are affected by this potentially disabling disease adversely impacting the vision-related quality of life.

Clinically significant DED is associated with ocular surface inflammation, although the precise immunopathogenesis is not known. There is strong evidence regarding T cell involvement in the pathogenesis of DED in both animal models and humans. Recently, we illustrated T cell activation in the regional lymph nodes of dry eye mice, coincident with acquisition of specific chemokine markers which help in the homing of T cells to the inflamed ocular surface. Further we demonstrated induction of autoimmunity in the draining lymph nodes of dry eye mice due to impaired Treg function and generation of pathogenic Th17 cells. These Th17 cells were found to be resistant to Treg mediated suppression, leading to unrestrained generation of pathogenic T cells and sustained ocular surface inflammation. Accordingly, much of the work to date has focused on understanding immunological phenomena occurring in the lymphoid compartment and the effector responses thereby generated, leaving unanswered the question as to how naive T cells in the draining lymph nodes get primed to the ocular surface antigen(s) that drive immunity in DED.

The draining lymph nodes are critical sites for induction of immunity and their role in generation of alloimmunity has been well established in corneal transplantation. The enhanced survival rate of corneal transplants in mice with excised cervical lymph nodes implicates the importance of functional flow of antigen presenting cells (APCs) from the ocular surface to the to the draining lymphoid tissue as a necessary component of alloimmunity and graft rejection. However, little is known about the pathway that allows trafficking of corneal APCs to the draining lymph nodes where they prime naive T cells to corneal antigens and generate autoimmune responses in dry eye.

Emphasis is now being given to the importance of pathological angiogenesis (hem- and lymphangiogenesis) in various corneal diseases such as different forms of keratitis, chemical burns, graft vs host disease etc., but to date there is no data regarding corneal angiogenesis in DED. A plausible reason could be that most of the above mentioned conditions except DED are accompanied by in-growth of clinically visible blood vessels into the cornea. Traditionally it has been thought that lymphatics and blood vessels which serve as afferent and efferent arms of the immune response respectively are always coexistent in pathological states. The present work provides the first evidence for selective lymphangiogenesis occurring in DED cornea using a murine model. Herein, we attempt to determine the growth of lymphatic vessels into the cornea with the progression of DED, discuss the pathophysiologic implications of corneal lymphangiogenesis in dry eye and the potential of antilymphangiogenic therapy for ameliorating DED.

Discussion

Lymphangiogenesis in the postnatal period is primarily a response to inflammation and is seen in various pathological states as diverse as tumor metastasis, wound healing and transplantation. Lymphatics play an important role in generating immuno-inflammatory responses by directing the antigen bearing immunocytes (e.g. dendritic cells) from the periphery to the draining lymph nodes where T cells are primed and expanded. The normal human cornea is avascular, thus suppressing the afferent lymphatic and efferent vascular arms of the immune cycle. Inflammation however negates this "immune" and "angiogenic" privileged state of the cornea and gives it the potential to mount an immune response.

Angiogenesis in the cornea is now extensively being studied in various pathological models such as transplantation. Whereas corneal blood vessels have long been thought to be an important risk factor for immune rejection in corneal transplantation, it is only recently after unveiling of new lymphatic specific markers, that the significance of lymphangiogenesis in corneal alloimmunity has been characterized. Despite recognizing the role of inflammatory angiogenesis in the eye, little has hitherto been studied regarding angiogenic mechanisms in DED. Desiccating stress in DED initiates an immune-based inflammatory response that is sustained by the ongoing interplay between the ocular surface and various pathogenic immune cells, primarily the $CD4^+$ T cells in the conjunctiva and $CD11b+$monocytic cells in the cornea. Desiccating stress induces secretion of inflammatory cytokines, especially interleukin (IL)-1, tumor necrosis factor-a, and IL-6 by ocular surface tissues, which facilitate the activation and migration of resident APCs toward the regional draining LN. Our data on frequencies of mature APC in the LN also suggest increased trafficking of mature APC in the LN of DED mice (FIG. 7). In the LN, these APCs stimulate naive T cells, leading to the expansion of IL-17 secreting Th17 cells and interferon (IFN)-y-secreting Th1 cells. Once these effectors are generated in the LN, they migrate to the ocular surface and secrete effector cytokines. Recent work has provided evidence for the induction of T cell mediated autoimmune responses in the regional lymph nodes of DED mice. But what has remained unanswered is how corneal APCs can traffic to the draining lymphoid compartment in order to initiate the immune cycle in DED.

Interestingly, to date there has been no published data on this important facet of immunity in DED. The data presented herein clearly demonstrates the development of lymphatic vessels in the setting of the dry eye state. These lymphatic vessels increase both in caliber and area while advancing toward the corneal center with progression of dry eye. Remarkably, these lymphatic vessels are not accompanied by growth of blood vessels. Various spatio-temporal studies examining relation between new blood and lymphatic vessels have led to the belief that a preexisting blood vascular bed is necessary to guide lymphangiogenesis. The current study refutes the general perception of wound healing models in skin where growth of lymphatic vessels follows that of blood vessels by several days. This is also in contrast to other robust models of corneal inflammation where there is either parallel outgrowth of blood and lymphatic vessels or the blood vessels are precedent over the lymphatics. This provides the first evidence of selective 'natural' (non pharmacologically induced) lymphangiogeneis in a disease model that is dissociated from hemangiogenesis.

Lymphangiogenesis is mediated primarily by the interaction of growth factors VEGF-C and VEGF-D on VEGFR-2 and VEGFR-3. VEGF-A also contributes, albeit indirectly, to lymphangiogenesis by recruiting VEGF-C and VEGF-D secreting macrophages. In the present study, dry eye induction led to the up-regulation of all the VEGF growth factors and their receptors. Though the rise in levels of VEGF-A, VEGF-C and VEGFR-2 occurred at later time points (day 14), it is noteworthy, that VEGF-D and VEGFR-3 (which are both largely specific to lymphangiogenesis) increased as early as day 6 of disease. The functional relevance of the early rise of VEGF-D is highlighted in a recent study where VEGF-D, via its action on VEGFR-3, was shown to be a critical modifier of VEGF-C driven early sprouting and migration of lymphatic endothelial cells. Macrophages also seem to play a crucial role in lymphangiogenesis. Under normal physiological conditions, all ocular tissues except the central cornea are rich in bone marrow derived $LYVE-1^+$ macrophages which may serve as precursor cells for de novo formation of lymphatics. In the present study, we noticed significantly increased number of $CD11b^+/LYVE-1^+$ cells in the peripheral corneas after exposure to desiccating stress, suggesting that either these cells infiltrate into or multiply from pre-existing CD113'7 LYVE-1+ cells in the cornea, and contribute to lymphangiogenesis. Alternatively, there is a possibility of upregulation of LYVE-1 in the previous CD11b+/LYVE-1− cells.

In summary, presented herein is novel evidence for the selective growth of lymphatic (but not blood) vessels in dry eye disease providing new insights into the pathophysiology of the disease. The findings suggest that these newly formed corneal lymphatics may serve as potential conduits for migration of corneal APCs to lymphoid tissues where they generate autoreactive Th17 and Th1 cells in DED. This study not only provides a link between ocular surface inflammation and the generation of T cell mediated immunity in the lymphoid compartment, but also offers an example of how lymphangiogenesis and hemangiogenesis can be 'naturally' dissociated in a pathological state. The severing of the 'eye-lymphatic axis' in other immune-mediated conditions, such as transplant rejection, has been shown to hold promise as a strategy of suppressing alloimmunity without inhibiting needed innate host defense mechanisms. Similarly, a strategy targeting prolymphangiogenic factors such as VEGF-C or VEGF-D may prove effective in ameliorating dry eye disease.

Example 7

Blockade of Prolymphangiogenic VEGF-C Suppresses Dry Eye Disease

Effect of in vivo blockade of pro-lymphangiogenic VEGF-C on Dry Eye Disease Rationale Dry eye disease (DED) is an immune-mediated disorder whose precise pathogenesis remains largely unknown. While it has been clearly established that in DED generation of pathogenic CD4+ T cells (Th1/Th17) primarily occur in the draining lymph nodes, the mechanisms of trafficking of corneal antigen presenting cells (APC) to lymphoid tissues where they activate and expand pathogenic CD4+ T cell subsets, were still not well understood prior to the invention described herein. The present invention provides evidence for the selective growth of lymphatic (but not blood) vessels in DED cornea. Data shows a significant increase in both caliber and extent of lymphatics in DED corneas which was also confirmed using real-time PCR by showing a highly significant over-expression of lymphangiogenic receptor VEGFR-3 (in contrast to a non-statistically significant increase in hemangiogenic receptor VEGFR-2 expression). This study not only provides a link between ocular surface inflammation and the generation of T-cell mediated immunity in the lymphoid compartment, but also offers an example of how lymphangiogenesis and hemangiogenesis can be 'naturally' dissociated in a pathological state. Data suggests that these corneal lymphatics may serve as conduits for migration of corneal APCs to lymphoid tissues where they activate autoreactive T cells in DED.

Immunopathogenesis of DED: The pathogenesis is not fully understood. Ocular surface inflammation sustained by ongoing activation and infiltration of pathogenic immune cells. Strong evidence of T cell involvement. Recent work draining lymphoid tissue primary site for activation and generation of auto reactive effector T cells in DED (Chauhan et al; Role ofcTh17 cells in the immunopathogenesis of dry eye disease. Mucosal Immunol. 2009; 2 (4):375-376).

Expression levels of VEGF's and VEGFR's in DE corneas using RT PCR has demonstrated an increased transcript expression of VEGF-C, VEGF-D, and VEGFR-3. Thus, targeting pro-lymphangiogenic VEGF-C/D has therapeutic implications in DED.

Corneal lymphatics play an important role in mediating the corneal inflammation in dry eyes. Experiments: To validate this, inhibition of corneal neolymphangiogenesis was performed in a well characterized mouse model of DED described above. To see if inhibition of corneal neolymphangiogenesis could decrease ocular surface inflammation, anti-VEGF-C antibodies were administered i.p. daily from day −1 to day 10 to DED mice and assessed clinically using corneal fluorescein staining.

Methods (as described previously): Induction of Dry Eye Disease. Experimental Dry Eye Murine Model. Assessment of Corneal Surface: Corneal Fluorescein Staining. Immunohistochemistry: Monocyte/macrophage marker—CD11b; Pan-endothelial marker—CD31; Lymphatic endothelial marker—LYVE-1; Blood vessels: $CD31^{hi}$/LYVE-1; Lymph vessels: $CD31^{lo}$/LYVE-$1^{hi}$. Morphometry of Lymphangiogenesis: Automated image analysis program written using Mat lab. Lymphatic Area (LA)—total surface area of the lymphatic vessels when projected into the plane of the image. Lymphatic Caliber (LC)—measure of the diameters of the lymphatic vessels.

Anti-VEGF-C antibody and treatment regimen. Experimental design: Three groups: Normal, DE group treated with IP normal Saline (Untreated) and DE group treated with anti-VEGF-C antibody (VGX-100; a gift from Vegenics, Australia). Daily IP application of anti-VEGF-C antibody/Normal saline from day −1 to day 13. Dose: 400 pg (20 mg/kg) in 100 µl of Normal Saline.

Figure 14:
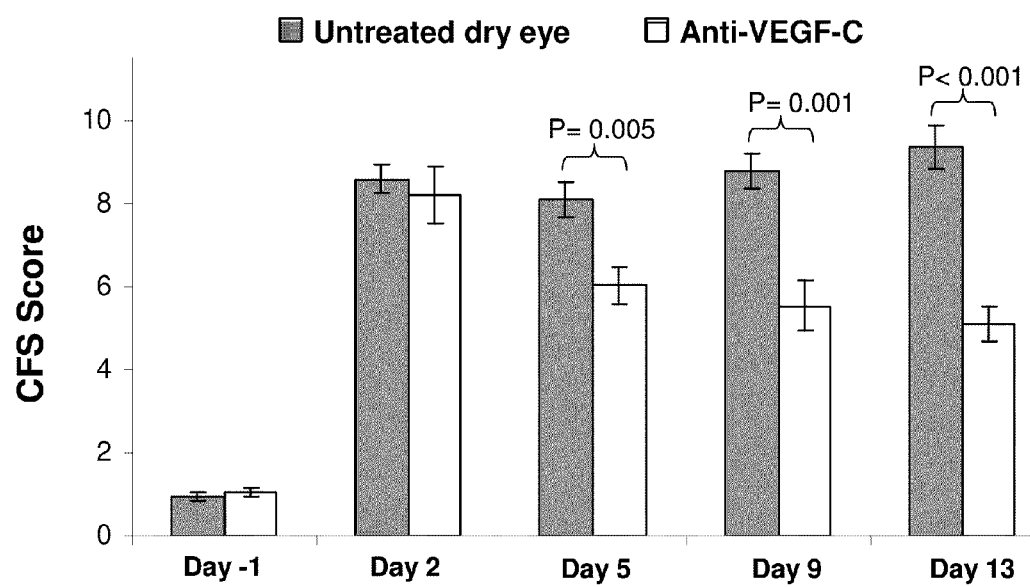
FIG. 14: In vivo blockade of VEGF-C ameliorates clinical signs of DED. Corneal fluorescein staining (CFS) score is used as readout for the clinical signs of dry eye inflammation, in anti-VEGF-C Ab-treated and untreated mice. CFS scores were significantly decreased in the group treated with anti-VEGF-C antibody at days 5, 9 and 13 vs the untreated group. Data shown as mean±S.E.M and each group consisted of 3-4 mice.

The results are presented in FIG. 14. Results: The data clearly shows a significant decrease in disease severity in anti-VEGF-C-treated group compared to the untreated group. In conclusion, suppression of lymphatic growth with VEGF-C blockade led to significant improvement in DED reflected by decrease in: corneal epitheliopathy; corneal infiltration of CD11b+ cells; expression of pro-lymphangiogenic growth factors and receptors (VEGF-C, -D, R3) in DE corneas; and mRNA expression levels of proinflammatory cytokines in the conjunctiva.

Those skilled in the art will recognize, or be able to ascertain using no more than routine experimentation, many equivalents to the specific embodiments of the invention described herein. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations. Such equivalents are intended to be encompassed by the following claims.

What is claimed is:

1. A method of treating dry eye disease (DED) in a human comprising:
administering a composition comprising a VEGF-C antibody or antigen binding fragment thereof, and a pharmaceutically acceptable carrier to the eye of the human, wherein the VEGF-C antibody or antigen binding fragment thereof binds human VEGF-C and comprises a heavy chain variable region set forth in amino acids 1-118 of SEQ ID NO: 34 and a light chain variable region set forth in amino acids 1-112 of SEQ ID NO: 35, and wherein the composition is administered in an amount effective to treat dry eye disease.

2. The method of claim 1, wherein the DED is an autoimmune DED or a DED associated with Sjogren's syndrome.

3. The method of claim 1, wherein the DED is DED due to excessively fast tear evaporation (evaporative dry eyes) or inadequate tear production.

4. The method of claim 1, wherein the dry eye disease is attributable to one or more causes selected from the group consisting of aging, contact lens usage and medication usage.

5. The method of claim 1, wherein the dry eye disease is a complication of LASIK refractive surgery.

6. The method of claim 1, wherein the method further comprises administering an antibiotic to the human.

7. The method of claim 6, wherein the antibiotic is selected from the group consisting of amikacin, gentamicin, kanamycin, neomycin, netilmicin, streptomycin, tobramycin, teicoplanin, vancomycin, azithromycin, clarithromycin, clarithromycin, dirithromycin, erythromycin, roxithromycin, troleandomycin, amoxicillin, ampicillin, azlocillin, carbenicillin, clozacillin, dicloxacillin, flucozacillin, meziocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, oflazacin, trovafloxacin, mafenide, sulfacetamide, sulfamethizole, sulfasalazine, sulfisoxazole, trimethoprim, cotrimoxazole, demeclocycline, soxycycline, minocycline, oxytetracycline, and tetracycline.

8. The method of claim 1, wherein the eye comprises a tissue or gland in or around the eye selected from the group consisting of ocular tissue, eyelids of the subject, ocular surface, meibomian gland and or lacrimal gland of the human.

9. The method of claim 1, wherein said composition is administered topically to the eye.

10. The method of claim 1, wherein said composition is in the form of a solid, a paste, an ointment, a gel, a liquid, an aerosol, a mist, a polymer, a film, an emulsion, or a suspension.

11. The method of claim 1, wherein the composition further comprises a compound selected from the group consisting of physiological acceptable salt, poloxamer analogs with carbopol, carbopol/hydroxypropyl methyl cellulose (RP MC), carbopol-methyl cellulose, carboxymethylcellulose (CMC), hyaluronic acid, cyclodextrin, and petroleum.

12. A method of treating dry eye disease (DED) in a human comprising:
   administering a composition comprising a VEGF-C antibody or antigen binding fragment thereof, and a pharmaceutically acceptable carrier to the eye of the human, wherein the VEGF-C antibody or antigen binding fragment thereof binds human VEGF-C and comprises a heavy chain set forth SEQ ID NO: 34 and a light chain variable region set forth in amino acids 1-112 of SEQ ID NO: 35, and wherein the composition is administered in an amount effective to treat dry eye disease.

13. The method of claim 12, wherein the DED is an autoimmune DED or a DED associated with Sjogren's syndrome.

14. The method of claim 12, wherein the DED is DED due to excessively fast tear evaporation (evaporative dry eyes) or inadequate tear production.

15. The method of claim 12, wherein the dry eye disease is attributable to one or more causes selected from the group consisting of aging, contact lens usage and medication usage.

16. The method of claim 12, wherein the dry eye disease is a complication of LASIK refractive surgery.

17. The method of claim 12, wherein the method further comprises administering an antibiotic to the human.

18. The method of claim 17, wherein the antibiotic is selected from the group consisting of amikacin, gentamicin, kanamycin, neomycin, netilmicin, streptomycin, tobramycin, teicoplanin, vancomycin, azithromycin, clarithromycin, clarithromycin, dirithromycin, erythromycin, roxithromycin, troleandomycin, amoxicillin, ampicillin, azlocillin, carbenicillin, clozacillin, dicloxacillin, flucozacillin, meziocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, oflazacin, trovafloxacin, mafenide, sulfacetamide, sulfamethizole, sulfasalazine, sulfisoxazole, trimethoprim, cotrimoxazole, demeclocycline, soxycycline, minocycline, oxytetracycline, and tetracycline.

19. The method of claim 12, wherein the eye comprises a tissue or gland in or around the eye selected from the group consisting of ocular tissue, eyelids of the subject, ocular surface, meibomian gland and or lacrimal gland of the human.

20. The method of claim 12, wherein said composition is administered topically to the eye.

21. The method of claim 12, wherein said composition is in the form of a solid, a paste, an ointment, a gel, a liquid, an aerosol, a mist, a polymer, a film, an emulsion, or a suspension.

22. The method of claim 12, wherein the composition further comprises a compound selected from the group consisting of physiological acceptable salt, poloxamer analogs with carbopol, carbopol/hydroxypropyl methyl cellulose (RPMC), carbopol-methyl cellulose, carboxymethylcellulose (CMC), hyaluronic acid, cyclodextrin, and petroleum.

* * * * *

UNITED STATES PATENT AND TRADEMARK OFFICE
CERTIFICATE OF CORRECTION

Page 1 of 2

PATENT NO. : 9,011,861 B2
APPLICATION NO. : 13/035695
DATED : April 21, 2015
INVENTOR(S) : Reza Dana et al.

It is certified that error appears in the above-identified patent and that said Letters Patent is hereby corrected as shown below:

In the Specification

At Column 1, Line 17-19: "This invention was made with Government support under Grant No EY-12963 awarded by the National Institute of Health. The Government has certain rights in the invention." should read --This invention was made with Government support under Grant No EY012963 awarded by the National Institutes of Health. The Government has certain rights in the invention.--

At Column 3, Line 5-6: "clarithromycin, clarithromycin" should be --clarithromycin,--

At Column 3, Line 8: "flucozacillin" should be --flucloxacillin--

At Column 3, Line 8: "clozacillin," should be --cloxacillin,--

At Column 3, Line 12: "oflazacin," should be --oflaxacin,--

At Column 3, Line 14: "soxycycline," should be --doxycycline--

At Column 3, Line 27: "(RP MC)" should be --(HPMC)--

In the Claims

At Column 94, Line 40-41: "clarithromycin, clarithromycin" should be --clarithromycin,--

At Column 94, Line 43: "clozacillin" should be --cloxacillin--

At Column 94, Line 43: "flucozacillin" should be --flucloxacillin--

At Column 94, Line 46: "oflazacin," should be --oflaxacin,--

Signed and Sealed this
Eleventh Day of August, 2020

Andrei Iancu
*Director of the United States Patent and Trademark Office*

CERTIFICATE OF CORRECTION (continued)
U.S. Pat. No. 9,011,861 B2

At Column 94, Line 49: "soxycycline," should be --doxycycline--

At Column 94, Line 54: "and or" should be --and/or--

At Column 94, Line 66: "(RP MC)" should be --(HPMC)--

At Column 95-96, Line 28-1: "clarithromycin, clarithromycin" should be --clarithromycin,--

At Column 96, Line 3: "clozacillin" should be --cloxacillin--

At Column 96, Line 3: "flucozacillin" should be --flucloxacillin--

At Column 96, Line 6: "oflazacin," should be --oflaxacin,--

At Column 96, Line 9: "soxycycline," should be --doxycycline--

At Column 96, Line 14: "and or" should be --and/or--

At Column 96, Line 24-25: "(RP MC)" should be --(HPMC)--